US011007254B2

(12) United States Patent
Tomlinson et al.

(10) Patent No.: US 11,007,254 B2
(45) Date of Patent: May 18, 2021

(54) COMPOSITIONS AND METHODS FOR TREATING CENTRAL NERVOUS SYSTEM INJURY

(71) Applicants: MUSC Foundation For Research Development, Charleston, SC (US); United States Government as Represented by the Department of Veteran Affairs, Washington, DC (US)

(72) Inventors: Stephen Tomlinson, Charleston, SC (US); DeAnna Adkins, Charleston, SC (US); Ali Alawieh, Charleston, SC (US)

(73) Assignees: MUSC Foundation For Research Development, Charleston, SC (US); United States Government as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 16/342,853

(22) PCT Filed: Oct. 17, 2017

(86) PCT No.: PCT/US2017/056912
§ 371 (c)(1),
(2) Date: Apr. 17, 2019

(87) PCT Pub. No.: WO2018/075474
PCT Pub. Date: Apr. 26, 2018

(65) Prior Publication Data
US 2019/0247478 A1    Aug. 15, 2019

Related U.S. Application Data

(60) Provisional application No. 62/409,196, filed on Oct. 17, 2016.

(51) Int. Cl.
| A61K 38/00 | (2006.01) |
| A61K 38/57 | (2006.01) |
| C07K 16/18 | (2006.01) |
| A61K 38/17 | (2006.01) |
| A61K 38/49 | (2006.01) |
| A61P 25/00 | (2006.01) |
| A61K 39/00 | (2006.01) |

(52) U.S. Cl.
CPC .......... *A61K 38/57* (2013.01); *A61K 38/1709* (2013.01); *A61K 38/1725* (2013.01); *A61K 38/49* (2013.01); *A61P 25/00* (2018.01); *C07K 16/18* (2013.01); *A61K 2039/505* (2013.01); *C07K 2317/622* (2013.01)

(58) Field of Classification Search
None
See application file for complete search history.

(56) References Cited

U.S. PATENT DOCUMENTS

| 4,943,529 A | 7/1990 | Van den Berg et al. |
| 5,328,470 A | 7/1994 | Nabel et al. |
| 5,580,723 A | 12/1996 | Wells et al. |
| 5,679,345 A | 10/1997 | Sanfilippo et al. |
| 6,333,034 B1 | 12/2001 | Gupta-Bansal et al. |
| 6,355,245 B1 | 3/2002 | Evans et al. |
| 7,423,128 B2 | 9/2008 | Gazit-Bornstein et al. |
| 7,439,331 B2 | 10/2008 | Fung et al. |
| 2005/0260198 A1 | 11/2005 | Holers et al. |
| 2006/0052281 A1 | 3/2006 | Zlokovic et al. |
| 2007/0009528 A1 | 1/2007 | Larsen et al. |
| 2008/0029911 A1 | 2/2008 | Jeon et al. |
| 2008/0118506 A1 | 5/2008 | An et al. |
| 2009/0017031 A1 | 1/2009 | Fung |
| 2011/0014614 A1 | 1/2011 | Liew |
| 2016/0083469 A1 | 3/2016 | Rohrer et al. |

FOREIGN PATENT DOCUMENTS

| EP | 0139383 A1 | 5/1985 |
| EP | 0183070 A2 | 6/1986 |
| EP | 0244234 A2 | 11/1987 |
| EP | 0394538 A1 | 10/1990 |
| EP | 0402226 A1 | 12/1990 |
| WO | WO-9100357 A1 | 1/1991 |
| WO | WO-9109967 A1 | 7/1991 |
| WO | WO-9109968 A1 | 7/1991 |
| WO | WO-0206460 A2 | 1/2002 |
| WO | WO-2004075837 A2 | 9/2004 |
| WO | WO-2004106384 A1 | 12/2004 |
| WO | WO-2008154018 A2 | 12/2008 |

(Continued)

OTHER PUBLICATIONS

Claflin et al. The Neurohospitalist, 2015, vol. 5(2) 77-88.*
Alawieh, Ali et al. "Complement in the Homeostatic and Ischemic Brain." Frontiers in immunology, vol. 6, 417, pp. 1-18, 12 Aug. 2015, doi:10.3389/fimmu.2015.00417.
Alawieh, Ali et al. "Modulation of post-stroke degenerative and regenerative processes and subacute protection by site-targeted inhibition of the alternative pathway of complement." Journal of neuroinflammation vol. 12 247. Dec. 30, 2015, doi:10.1186/s12974-015-0464-8.
ATCC Deposit No. ATCC _16045.
ATCC Deposit No. ATCC _24178.
ATCC Deposit No. ATCC _27325.
ATCC Deposit No. ATCC _31449.

(Continued)

*Primary Examiner* — Jeanette M Lieb
(74) *Attorney, Agent, or Firm* — McCarter & English, LLP

(57) ABSTRACT

The present invention describes compositions and method for improving outcomes after injury to the central nervous system wherein complement signaling is activated. In one aspect, the method comprises administering to a subject a therapeutically effective amount of a therapeutic agent comprising a targeted inhibitor molecule comprising a targeting portion and an inhibitor portion, wherein the molecule inhibits complement, and wherein therapeutic agent is administered in combination with rehabilitation therapy or thrombolytic agent.

9 Claims, 32 Drawing Sheets

Specification includes a Sequence Listing.

(56) References Cited

FOREIGN PATENT DOCUMENTS

| | | |
|---|---|---|
| WO | WO-2008154251 A2 | 12/2008 |
| WO | WO-2009029669 A1 | 3/2009 |
| WO | WO-2009056631 A2 | 5/2009 |
| WO | WO-2009110918 A1 | 9/2009 |
| WO | WO-2010015608 A1 | 2/2010 |
| WO | WO-2010136311 A2 | 12/2010 |
| WO | WO-2015187992 A2 | 12/2015 |

OTHER PUBLICATIONS

ATCC Deposit No. ATCC _31537.
ATCC Deposit No. ATCC _36906.
ATCC Deposit No. ATCC _56500.
ATCC Deposit No. ATCC_12424.
ATCC Deposit No. PTA-6230.
Atkinson, Carl et al. "Targeted complement inhibition by C3d recognition ameliorates tissue injury without apparent increase in susceptibility to infection." The Journal of clinical investigation vol. 115,9 (2005): 2444-53. doi:10.1172/JCI25208.
Atkinson, Carl et al. "Targeting pathogenic postischemic self-recognition by natural IgM to protect against post transplantation cardiac reperfusion injury." Circulation vol. 131,13 (2015): 1171-80. doi:10.1161/CIRCULATIONAHA.114.010482.
Atkinson et al. "Complement-Dependent P-Selectin Expression and Injury following Ischemic Stroke", Journal ofImmunology, 177 (2006): 7266-7274.
Ballance et al. Transformation of Aspergillus nidulans by the orotidine-5'-phosphate decarboxylase gene of Neurospora crassa. Biochem. Biophys. Res. Commun. 112:284-289 (1983).
Beach et al. High-frequency transformation of the fission yeast Schizosaccharomyces pombe. Nature 290:140-142 (1981).
Brauer et al. "Functional Activity of Anti-C6 Antibodies Elicited in C6-Deficient Rats Reconstituted by Liver Allografts ", Transplantation 61.4, (1996): S88-S94.
C. Anthony, "The Biochemistry of Methylotrophs", 269 (1982).
Carter et al. Humanization of an anti-p185HER2 antibody for human cancer therapy. PNAS USA 89(10):4285-4289 (1992).
Chen et al. "Gene therapy for brain tumors: Regression of experimental gliomas by adenovirus-mediated gene transfer in vivo", Proc. Natl. Acad. Sci., USA 91, (1994): 3054-3057.
Co et al. "Humanized antibodies for antiviral therapy", Proc. Natl.Acad. Sci. USA 88, (1992): 2869-2873.
Cunningham et al. High-Resolution Epitope Mapping of hGH-Receptor Interactions by Alanine-Scanning Mutagenesis. Science 244:1081-1085 (1989).
Dev, et al. "Electrochemotherapy—a novel method of cancer Treatment", Cancer Treat. Rev. 20, (1994): 105-115.
Elvington, Andrew et al. "Pathogenic natural antibodies propagate cerebral injury following ischemic stroke in mice." Journal of immunology (Baltimore, Md. : 1950) vol. 188,3 (2012): 1460-8. doi:10.4049/jimmunol.1102132.
Fleer, R. et al., "Stable Multicopy Vectors for High-Level Secretion of Recombinant Human Serum Albumin by Kluyveromyces Yeasts," Nature BioTechnology 9, (1991): 968-975.
Hill., "Eculizumab for the Treatment of Paroxysmal Nocturnal Hemoglobinuria", Clin Adv Hematol Oneal 3.11, (2005): 849-50.
Hillmen, et al. "Effect of Eculizumab on Hemolysis and Transfusion Requirements in Patients with Paroxysmal Nocturnal Hemoglobinuria", N Engl J Med 350.6 (2004): 552.
International Preliminary Report on Patentability dated Apr. 23, 2019 for International Application Serial No. PCT/US2017/056912, 8 pages.
International Search Report dated Feb. 21, 2018 for International Application Serial No. PCT/US2017/056912, 6 pages.
Johan A. van den Berg et al., "Kluyveromyces As a Host for Heterologous Expression: Expression and Secretion of Prochymosin" , Bio Technology, vol. 8, pp. 135-139, Feb. 1990.

Johne, et al. "Epitope mapping and binding kinetics of monoclonal antibodies studied by real time biospecific interaction analysis using surface plasmon resonance", Journal of immunological Methods, 160, (1993): 191-198.
Jonsson, et al. "Introducing a biosensor based technology for real-time biospecific interaction analysis", Ann Biol Clin 51, (1993): 19-26.
Jonsson, et al. "Real-Time Biospecific Interaction Analysis Using Surface Plasmon Resonance and a Sensor Chip Technology", Ann Biol Clin 51, (1991): 19-26.
Kabat, et al. "Experimental Immunochemistry, 2nd Edition," 135-240, Springfield, III., C C Thomas (1961), pp. 135-139.
Kaplan., "Eculizumab (Alexion)."Current Opinion in Investigational Drugs 3.7, (2002): 1017-23.
Kelly et al. Transformation of Aspergillus niger by the amdS gene of Aspergillus nidulans. Embo J. 4:475-479 (1985).
Liudmila Kulik et al., "Pathogenic natural antibodies recognizing annexin IV are required to develop intestinal ischemia-reperfusion injury", J Immunol., vol. 182, No. 9, pp. 5363-5373, May 1, 2009 doi: 10.4049/jimmunol.0803980.
Lovencourt et al., "Transformation of Kluyveromyces Jactis by Killer Plasmid DNA" Journal of Bacteriology 154.2, (May 1983): 737-742.
Mandel, M. et al., "Calcium-dependent Bacteriophage DNA Infection," J. Mol. Bioi. 53, (1970): 159-162.
Mary E. Case et al., "Efficient transformation of Neurospora crassa by utilizing hybrid plasmid DNA", Proc. Natl. Acad. Sci. USA, vol. 76, No. 10, pp. 5259-5263, Oct. 1979.
Meri et al., "Structural composition and functional characterization of soluble CD 59: heterogeneity of the oligosaccharide and glycophosphoinositol (GPI) anchor revealed by laserdesorption mass spectrometric analysis," Biochem. J. 316, (1996): 923-935.
Mette Møller-Kristensen et al., "Levels of mannan-binding lectin-associated serine protease-2 in healthy individuals", Journal of Immunological Methods, 282, pp. 159-167, 2003.
Mollnes, et al. "Identification of a Human C5 β-Chain Epitope Exposed in the Native Complement Component but Concealed in the SC5b-9 Complex", Scand J. Immunol. 28, (1988): 307-312.
Moongkamdi. et al. "Immunological and functional properties of two monoclonal antibodies against human CS" Immunobiol 165, (1983): 323.
Moongkamdi. et al. Monoclonal antibodies against the fifth component of human complement, Immunobiol 162, (1982): 397.
Morrison, S.L. et al., "Chimeric human antibody molecules: mouse antigen-binding domains with human constant region domains," Proc. Nat'/ Acad. Sci. USA 81, (Nov. 1984): 6851-55.
Niemann et al. "The Use of Monoclonal Antibodies As Probes of the Three- Dimensional Structure of Human Complement Factor D", The Journal of Immunology, 132.2, (1984): 809-815.
Oglesby, T.J. et al., "Membrane cofactor protein (CD46) protects cells from complement mediated attack by an intrinsic mechanism", J. Exp. Med., 175, (Jun. 1992): 1547-1551.
Pascual, et al. "A monoclonal antibody which blocks the function of factor D of human complement", Journal of Immunological Methods 127, (1990): 263-269.
Pascual, et al. "Inhibition of complement alternative pathway in mice with Fab antibody to recombinant adipsin/factor D", Eur Journal of Immunology, 23, (1993): 1389-1392.
Patel, et al. "A novel therapy for myocardial ischemia-reperfusion",Drugs Today (Bare) 41.3, (2005): 165-70.
Petersen, et al., "An assay for the mannan-binding lectin pathway of complement activation", Journal of Immunological Methods, 257, (2001): 107-16.
Petersen, et al., "Control of the classical and the MBL pathway of complement Activation", Molecular Immunology, 37, (2000): 803-11.
Petersen, et al., "Generation of Antibodies Towards Masp-1 and Masp-2 Using Bacterial Expression Systems", Molecular Immunology, 35: 409.
Petersen, et al., "The mannan-binding lectin pathway of complement activation: biology and disease association", Molecular Immunology, 38, (2001): 133-149.

(56) References Cited

OTHER PUBLICATIONS

Rescher, et al. Annexins—unique membrane binding proteins with diverse functions. J Cell Sci. Jun. 1, 2004;117(Pt 13):2631-9.
Rother, et al. "Discovery and development of the complement inhibitor eculizumab for the treatment of paroxysmal nocturnal hemoglobinuria", Nature Biotechnol 25.11, (2007): 1256-1488.
Routledge, E.G. et al., "A humanized monovalent CD3 antibody which can activate homologous complement," Eur. J. Immunol. 21, (1991): 2717-2725.
Sahu, et al. "Identification of Multiple Sites of Interaction Between Heparin and the Complement System", Molecular Immunology 30.7, (1993): 679-684.
Skjodt, et al., "MBL-associatedserineprotease-3 circulates in high serum concentrations predominantlyincomplexwithFicolin-3andregulatesFicolin-3mediated complement activation", Immunobiology, 215, (2010): 921-31.
Sreekrishna et al. High level expression of heterologous proteins in methylotrophic yeast Pichia pastoris. J. Basic Microbiol. 28:265-278 (1988).
Studier et al. Use of T3 RNA polymerase to direct expression of cloned genes. Methods Enzymol. 185:60-89 (1990).
Supplementary European Search Report dated Jun. 9, 2020 for Application No. EP 17861529.0, (6 pages).
Tan, et al. "Influence of the hinge region on complement activation, C1q binding, and segmental flexibility in chimeric human immunoglobulins", Proc Natl Acad Sci USA 87, (1990): 162-166.
Tanhehco, et al. "The Anti-Factor D Antibody, MAb 166-32, Inhibits the Alternative Pathway ofthe Human Complement System", Transplant Proc 31.5, (1999): 2168-71.
Thiel, et al., A second serine protease associated with mannanbinding lectin that activates complement, Nature, 386, (1997): 506-10.
Thomas, et al. "Inhibition of Complement Activity by Humanized Anti-C5 Antibody and Single-Chain Fv", Mol Immunol. 33.17-18, (1996): 1389-401.
Tilburn, J. et al., "Transformation by integration in Aspergillus nidulans," Gene 26, (1983): 205-221.
Ueda, et al. "Probing Functional Sites on Complement Protein With Monoclonal Antibodies", J Immunoll 38.4, (1987): 1143-9.
UniProtKB/Swiss-Prot. Accession No. Q61475.
UnitProtKB/Swiss-Prot. Accession No. P06909, (Sep. 2, 2008).
UnitProtKB/Swiss-Prot. Accession No. P08173, (Jul. 22, 2008).
UnitProtKB/Swiss-Prot. Accession No. P08603, (Jul. 22, 2008).
UnitProtKB/Swiss-Prot. Accession No. P15529, (Sep. 2, 2008).
UnitProtKB/Swiss-Prot. Accession No. P17927, (Jul. 22, 2008).
Whiss, "Pexelizumab Alexion Per A Whiss", Curr Opin Investig Drugs 3.6, (2002): 870-7.
Whittle et al. "Expression in COS cells of a mouse -human chimaeric B72.3 Antibody", Protein Engineering, (1987): 499-505.
Written Opinion of the International Searching Authority dated Feb. 21, 2018 for International Application Serial No. PCT/US2017/056912, 7 pages.
Yelton et al., "Transformation of Aspergillus nidulans by using a trpC plasmid" Proc. Nat'l Acad. Sci. USA 81, (1984): 1470-1474.
Zernii, et al. "Detection of Annexin IV in Bovine Retinal Rods", Biochemistry (Moscow), 68.1, (2003): 129-60.
Zhu, Haihao et al. "Annexin A2 combined with low-dose tPA improves thrombolytic therapy in a rat model of focal embolic stroke." Journal of cerebral blood flow and metabolism : official journal of the International Society of Cerebral Blood Flow and Metabolism vol. 30, No. 6, pp. 1137-1146., 2010, doi:10.1038/jcbfm.2009.279.

* cited by examiner

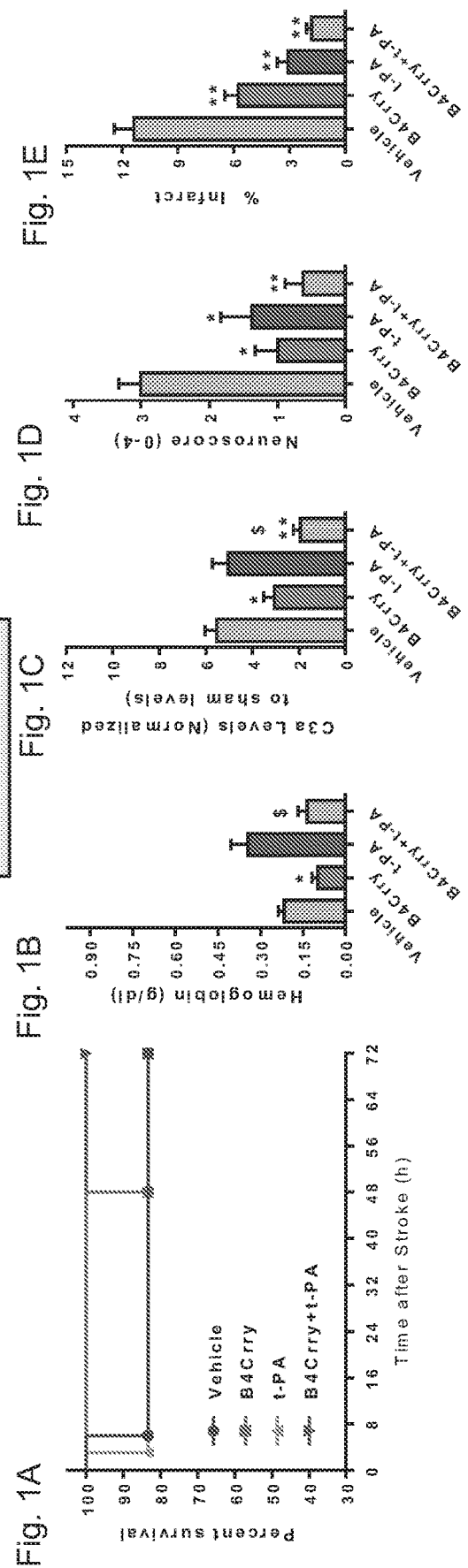

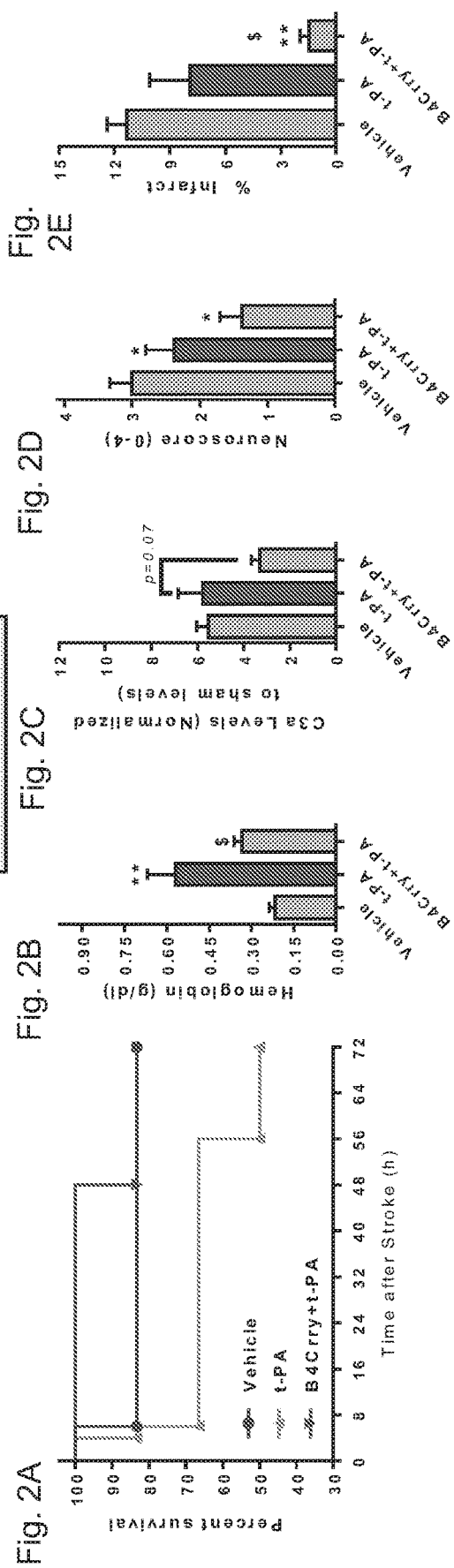

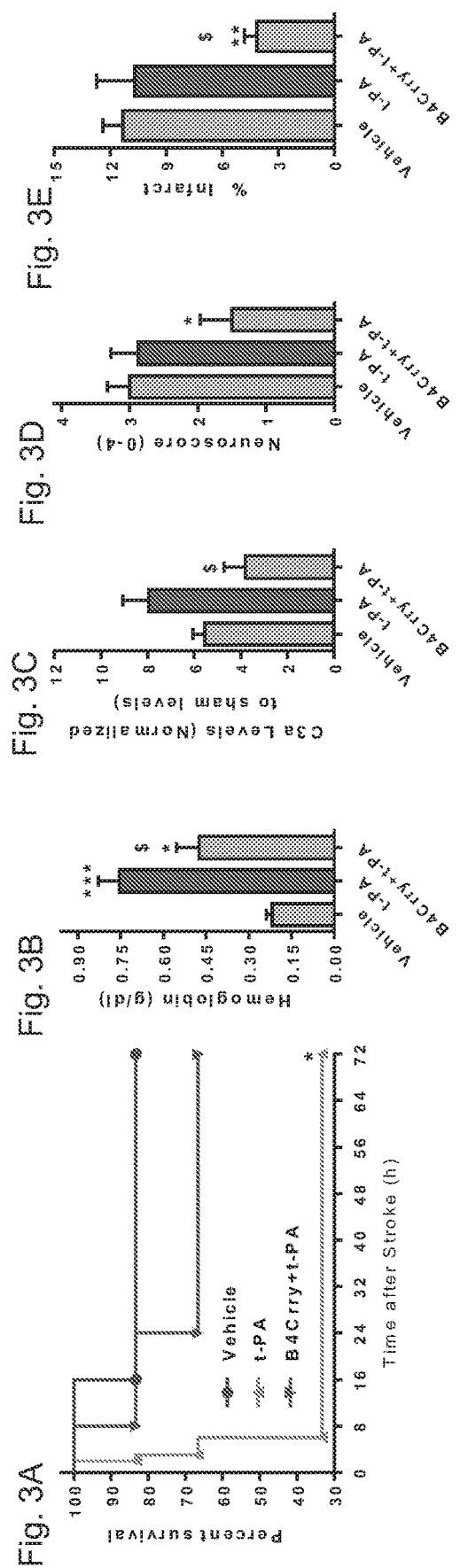

B4Crry nucleic acid sequence (SEQ ID NO: 61)

ATG TCC GTG CCT ACC CAG GTG CTC GGA CTC CTG CTG TGG CTC ACC GAC GCC AGG TGT GTG AAG CTG CAG GAG AGC GGA CCC GAG CTG GTG
AAG CCT GGA GCC TCC GTG AAG ATC AGC TGC AAG GCT TCC GGA TAC ACC TTC ACC GAC TAC ATG AAC TGG GTG AAG CAG AGC CAC GGC AAG
AGC CTG GAG TGG ATC GGC GAC ATC AAC CCT AAC AAC GGC GGC ACC TCC TAC AAC CAG AAG TTC AAG GGC AAG GCT ACA CTG ACC GTG GAC AAG
TCC AGC ACC GCC TAC ATG GAG CTC AGC AGC CTG AGG GAT TCC GCC GTC TAT TAC TGT GCC CGG TAC GAC TAC GCC TGG TAT TTC GAC
GTG TGG GGC CAG GGC ACA ACC GTC TCC AGC GCC GTG TCC AGC CTG AGC CTG GGA GAC CAA GCC TCC ATC TCC TGC AGG TCC ATC GTG CAC AGC AAT GGC AAC ACC
ACA CAG ACA CCT CTG GAG TGG TAT CTG CAG AAG CCT GGC CAG TCC CCC AAG CTG ATC CTG ATC TAC TAC AAG GTG TCC AAC CGG TTC AGC GGC GTC CCT GAC AGG TTC
TCC GGA TCC GGA AGC GGC ACA GAT TTC ACC CTG AAG ATC AGC AGG GTC GAG GAC CTG GAG GGT GGG TCG GGT GGC GGA TCT TGC CCA GCC CCA TCA CAG
CTT CCT TCT GCC AAA CCT CTA AAT CTA ACT GAT GAA TCC ATG TTT CCC ATT GGA ACA TAT TTG TAT GAA TGT CTC CCA GGA TAT ATC AAG AGG
CAG TTC TCT ATC ACC TGC AAA CAA GAC TCA ACC TGG ACG AGT GCT AAG TCT ATA CGA AAA CAA TGT AAA ACT CCT TCA GAT CCT GTA
GGC TTG GTA CAT GTA CAC ACA GGC ATT CAG TTT GGA TCC CGT ATT AAT TAT ACT TGT AAT CAA GGA TAC CGC CTC ATT GGT TCC TCC TCT GCT GTA
TGT GTC ATC ACT GAT CAA AGT GTT GAT TGG GAT ACT GAG GCA CCT ATT TGT GAG TGG ATT CCT TGT GAG ATA CCC CCA GGC ATT CCC AAT GGA GAT
TTC TTC AGT TCA ACC AGA GAA GAC TTT CAT TAT GGA ATG GTG GTT ACC TAC CGC TGC AAC ACT GAT GCG AGA GGG AAG GCG CTC TTT AAC CTG
GTG GGT GAG CCC TCC TTA TGT ACC AAG AAT GCA GTC ATG CTG TCT CAG TGT GTT GAA AAT GGA GTC TGG TGG AGC GGC CCT CCT CCT CAG TCC ATT GAA CTC AAC AAA TGT ACT
CCT CCT CCC TAT GTT GAA AAT GCA GTC ATG CTG TCT CAG TGT GTT GAA AAT GGA GTC TGG TTT TCC TTA AGG GAT ATT GTG GAG TTT AGA TGT CAC CCT GGC TTT
ATC ATG AAA GGA GCC AGC AGT GGA TTC CAG CAT GTG CAG TCA ATG CTG CTA AAC AAA TGG GAG CCA GAG TTA CAA AGC TGC TTC AAG GGA GTG ATA TGT CGT CTC
CCT CAG GAG ATG AGT GGA TTC CAG CAT GTG CAG AAG GGG TTG CAG AAA GAA TAT TAT TAT GGA GAG AAT GTA ACT TTG GAG GAT GGG TAT
ACT CTA GAA GGC AGT TCT CAA AGC CAG TGC CAG TCT GAT GGC AGC TGG AAT CCT CTT CTG GCC AAA TGT GTA TCT CGC TCA ATC ATC GAG GGC
AGG CAT CAC CAC CAT CAC TGA

B4Crry amino acid sequence (SEQ ID NO: 62)

MSVPTQVLGLLLWLTDARCVKLQESGPELVKPGASVKISCKASGYTFTDYYMNWVKQSHGKSLEWIGDINPNNGGTSYNQKFKGKATLTVDKSSSTA
YMELRSLTSEDSAVYYCARYDYAWYFDVWGQGTTVTVSSGGGGSGGGGSGGGGSGGGGSDVLMTQTPLSLPVSLGDQASISCRSSQSIVHSNGNTYLEWYLQ
KPGQSPKLLIYKVSNRFSGVPDRFSGSGSGTDFTLKISRVEAEDLGVYYCFQGSHVPYTFGGGTKLEIKRGGGGSGGGGSGGGGSCPAPSQLPSAKPINLTDESM
FPIGTYLLYECLPGYIKRQFSITCKQDSTWTSAEDKCIRKQCKTPSDPENGLVHVHTGIQFGSRINYTCNQGYRLIGSSSAVCVITDQSVDWDTEAPICEWI
PCEIPPGIPNGDFFSSTREDFHYGMVVTYRCNTDARGKALFNLVGEPSLYCTSNDGEIGVWSGPPPQCIELNKCTPPPYVENAVMLSENRSLFSLRDIVE
FRCHPGFIMKGASSVHCQSLNKWEPELPSCFKGVICRLPQEMSGFQKGLGMKKEYYYGENVTLECEDGYTLEGSSQSQCQSDGSWNPLLAKCVSRSII
EGRHHHHHH

Figure 8

C2Crry amino acid sequence (SEQ ID NO: 63)

ATG AGC GTG CCT ACA CAG GTG CTC GGC CTG CTC CTC TGG CTG ACA GAC GCC CGG TGT GTG AAG CTG CAG GAG TCC GGA ACC GAG CTG GTG AAA CCT GGC GCC AGC GTG AAA CTG AGC TGC AAA GCC GGA TAC ACC TTC ACC TCC TAC ATG CAC TGG GTG AAA CAG AGG CCT GGC CAG GGC CTG GAA TGG ATT GGC AAC ATC AAC CCC AGC AAC GGC GGC ACC AAC TAC AAT GAG AAG TTC AAG AGC AAG GCC ACC CTG ACC GTG GAT AAG TCC TCC ACC GCC TAC GCC ATG CAG CTG ACC GTC TCC TCC CTC GAG GAC GCC GTC TAT TAC TGT GCC AGG CGG GGC ATC AGG CTG AGG CAC TTC GAC TAC TGG GGC CAA GGC ACA ACC GTC ACC GTG AGC TCC GGA GGA GGA GGC AGC GGA GGC TCC GGC GGA GGC GGA AGC GAC ATT CAG ATG ACC CAG AGC CCC AAG TTC ATG TCC ACC TCC GTC GGC AGC GTG AGC GTC ACC TGT AAG GCC CAG GAT GTC GGC ACA GCT GTG GCC TGG TAC CAG CAG AAG CCC GGC CAG TCC CCC AAG CTG CTG ATC TAC TGG GCT TCC ACA AGG CAT ACC GGC GTC CCC GAT AGG TTC ACA GGC TCC GGC TCC GGC ACC GAC TTC ACA CTC ACA ATC AGC AAC GTC CAG TCC GAG GAC CTG GCC GAC TAC TTC TGC CAG CAG TAC TCC AGC TAC CCC CTC ACC TTC GGC GCT GGC ACC AAG CTG GAA CTG AAA CGG GGC GGT GGT GGG TCG GGT GGC GGA TCT TGC CCA GCC CCA TCA CAG CTT CCT TCT GCC AAA CCT ATA AAT GAT GAA TCC ATG TTT CCC ATT GGA ACA TAT TTG TAT CTC CTA TAT TGG GCG AGT CCG AAA CTT AAG AGG CAG TTC TCT ATC ACC TGC AAA CAA CAA GAC TCA ACC GGC AGT GCT GAA GAT AAG TGT AAA CAA ACA TAT AAG AAG CTA GAT CCT GAG AAT GGC TTG GTA CAT GTA CAC ACA GGC ATT CAG TTT GGA TCC CGT ATT AAT TAT ACT TGT AAT GAA GGA TAC CGC TCA TTG GTT CGT TCC TCT GCT GTA TGT ATC ACT GAT CAA AGT GTT GAT ACT GGT GAT ACT TAC TGT GAG GCA CCT ATT CCT TGT GAG ATC CCA GGC AGG TGT GAT CAC CCA ATT GGA TTC ATT AGT GAA CAG AGA GAA GAC TTT CAT TAT GGA ATG GTG GTT ACC TAC CGC TGC AAC ACT GAT GCG AGA GGG AAG GCG CTC TTT AAC CTG GTG GGT GAG CCC TCC TTA TAC TGT TAC AGC AAC GAT GGT GAA ATT GGA GTC TGG AGC GGC CCT CCT CAG GAT GCA TTG AGG GAT ATT GTG GAG TTT AGA TGT AAA TGT ACT CCT CCT GTT GAA AAT GCA GTC ATG TTG TCT GAG AAC AGA AGC TTG TTT CCA GAG TTA CCA AGC TGC TTC AGC AGT GTT GAT CAC CCT GGC TTT ATC ATG AAA GGA GCC AGC AGT GTG CAT TGT CAG TCC CTA AAC AAA AAA GAA TAT TAT GGA GAG CCA GAG AAT GTA ACC TTG GAA TGT ATA TGT CGT CTC CCT CAG GAG ATG AGT GGA TTC CAG AAG GGG TTG GGA ATG AAA AAG GAG TAC TAT GGA GAG CAT CTC AAG GTT ATT GAG CTA GAA GGT TAT ACG TTA GAA GGC ACC AGT GGA CAA AGC TGC GGA AAT GCA GTC AGC GGA CAG AGT GGA AAG CCA AGG AAG AGC CAA ACT CAA GGT TTT GGC GGC TGG TCA GCA CCT TCT CTT TGC CAG CTA ACC TGT ATG AGC AGG TGG TCA TCT ACT CCT CAA GGG ATG GGG AAT GTA ACC AGC AGT CCC TCA GGA AAA GAA ATA GGA AAT ATA AAT CCT TCA GGG ACA ACT AAT TAC AGT GAG AAG TTC AAG TCA AAA GCT ACC CTG ACA GTG GAT AAG TCA AGT TCA ACT GCT TAC ATG CAA CTG AGC TCA CTG ACC TCT GAG GAC AGT GCC GTC TAC TAC TGT GCG AGA CGC GGA ATC CGC CTG AGG CAC TTT GAC TAC TGG GGC CAG GGC ACT ACC GTG ACA GTT TCG AGC GGA GGA GGG GGA AGT GGA GGA GGG GGG TCA GGG GGT GGT GGG AGC GAT ATC CAG ATG ACA CAG TCT CCT TCG TCC CTA TCT GCA TCT GTT GGT GAC CGG GTA ACC ATC ACG TGC CGA GCG TCT CAG GGA ATA AGC AGC GCT CTA GCC TGG TAT CAA CAG AAA CCT GGC AAG GCG CCC AAG TCC CTG ATT TAC GAT GCC TCC AGT CTC GAA AGC GGG GTG CCG TCC CGG TTT AGT GGG AGC GGG AGT GGC ACA GAC TTC ACC CTC ACC ATA TCT TCC CTG CAG CCG GAG GAT TTT GCT ACC TAT TAC TGT CAA CAG TTC AAT AGC TAT CCT CTG ACG TTC GGT CAG GGG ACC AAG GTG GAA ATC AAA CAC CAC CAT CAC CAT CAC TGA TAG

C2Crry amino acid sequence (SEQ ID NO: 64)

MSVPTQVLGLLLLWLTDARCVKLQESGTELVKPGASVKLSCKASGYTFTSYMHWVKQRPGQGLEWIGNINPSNGGTNYNEKFKSKATLTVDKSSSTAYMQLSSLTSEDSAVYYCARRGIRLRHFDYWGQGTTVTVSSGGGGSGGGGSDIQMTQSPKFMSTSVGDRVSITCKASQDVGTAVAWYQQKPGQSPKLLIYWASTRHTGVPDRFTGSGSGTDFTLTISNVQSEDLADYFCQQYSSYPLTFGAGTKLELKRGGGGSGGGGSCPAPSQLPSAKPINLTDESMFPIGTYLYLYECLPGYIKRQFSITCKQDSTWTSAEDKCIRKQCTPPPYVENAVMLSENRSLFSLRDIVEFRCHPGFIMKGASSVHCQSLNKWEPELPSCVVTYRCNTDARGKALFNLVGEPSLYCTSNDGEIGVWSGPPPQCIELNKCTPPPYVENAVMLSENRSLFSLRDIVEFRCHPGFIMKGASSVHCQSLNKWEPELPSCFKGVICRLPQEMSGFQKGLGMKKEYYGENVTLECEDGYTLEGSSQSQCQSDGSWNPLLAKCVSRSIIEGRHHHHHH

Figure 9

SEQUENCE LISTING

<160> NUMBER OF SEQ ID NOS: 64

<210> SEQ ID NO 1
<211> LENGTH: 7
<212> TYPE: PRT
<213> ORGANISM: Artificial Sequence
<220> FEATURE:
<223> OTHER INFORMATION: chemically synthesized

<400> SEQUENCE: 1

Ser Ser Ile Ser Ser Asn Tyr
1               5

<210> SEQ ID NO 2

```
<211> LENGTH: 3
<212> TYPE: PRT
<213> ORGANISM: Artificial Sequence
<220> FEATURE:
<223> OTHER INFORMATION: chemically synthesized

<400> SEQUENCE: 2

Arg Thr Ser
1

<210> SEQ ID NO 3
<211> LENGTH: 18
<212> TYPE: PRT
<213> ORGANISM: Artificial Sequence
<220> FEATURE:
<223> OTHER INFORMATION: chemically synthesized

<400> SEQUENCE: 3

Gln Gln Gly Ser Ser Ile Pro Arg Thr Arg Ser Glu Gly Ala Pro Ser
1               5                   10                  15

Trp Lys

<210> SEQ ID NO 4
<211> LENGTH: 8
<212> TYPE: PRT
<213> ORGANISM: Artificial Sequence
<220> FEATURE:
<223> OTHER INFORMATION: chemically synthesized

<400> SEQUENCE: 4

Gly Tyr Thr Phe Thr Ser Tyr Trp
1               5

<210> SEQ ID NO 5
<211> LENGTH: 8
<212> TYPE: PRT
<213> ORGANISM: Artificial Sequence
<220> FEATURE:
<223> OTHER INFORMATION: chemically synthesized

<400> SEQUENCE: 5

Ile Gly Pro Asn Ser Gly Gly Thr
1               5

<210> SEQ ID NO 6
<211> LENGTH: 22
<212> TYPE: PRT
<213> ORGANISM: Artificial Sequence
<220> FEATURE:
<223> OTHER INFORMATION: chemically synthesized

<400> SEQUENCE: 6

Ala Arg Arg Met Val Lys Gly Cys Tyr Gly Leu Leu Gly Pro Arg Asp
1               5                   10                  15

His Gly His Arg Leu Leu
            20

<210> SEQ ID NO 7
<211> LENGTH: 11
<212> TYPE: PRT
<213> ORGANISM: Artificial Sequence
<220> FEATURE:
<223> OTHER INFORMATION: chemically synthesized

<400> SEQUENCE: 7

Gln Ser Ile Val His Ser Asn Gly Asn Thr Tyr
```

```
1               5                   10
```

<210> SEQ ID NO 8
<211> LENGTH: 3
<212> TYPE: PRT
<213> ORGANISM: Artificial Sequence
<220> FEATURE:
<223> OTHER INFORMATION: chemically synthesized

<400> SEQUENCE: 8

Lys Val Ser
1

<210> SEQ ID NO 9
<211> LENGTH: 9
<212> TYPE: PRT
<213> ORGANISM: Artificial Sequence
<220> FEATURE:
<223> OTHER INFORMATION: chemically synthesized

<400> SEQUENCE: 9

Phe Gln Gly Ser His Val Pro Tyr Thr
1               5

<210> SEQ ID NO 10
<211> LENGTH: 8
<212> TYPE: PRT
<213> ORGANISM: Artificial Sequence
<220> FEATURE:
<223> OTHER INFORMATION: chemically synthesized

<400> SEQUENCE: 10

Gly Tyr Thr Phe Thr Asp Tyr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: chemically synthesized

<400> SEQUENCE: 11

Ile Asn Pro Asn Asn Gly Gly Thr
1               5

<210> SEQ ID NO 12
<211> LENGTH: 11
<212> TYPE: PRT
<213> ORGANISM: Artificial Sequence
<220> FEATURE:
<223> OTHER INFORMATION: chemically synthesized

<400> SEQUENCE: 12

Ala Arg Tyr Asp Tyr Ala Trp Tyr Phe Asp Val
1               5                   10

<210> SEQ ID NO 13
<211> LENGTH: 107
<212> TYPE: PRT
<213> ORGANISM: Artificial Sequence
<220> FEATURE:
<223> OTHER INFORMATION: chemically synthesized

<400> SEQUENCE: 13

Asp Ile Glu Leu Thr Gln Ser Pro Thr Thr Met Ala Ala Ser Pro Gly
1               5                   10                  15

Glu Lys Ile Thr Ile Thr Cys Ser Ala Ser Ser Ile Ser Ser Asn
            20                  25                  30

Tyr Leu His Trp Tyr Gln Gln Lys Pro Gly Phe Ser Pro Lys Leu Leu
        35                  40                  45

Ile Tyr Arg Thr Ser Asn Leu Ala Ser Gly Val Pro Ala Arg Phe Ser
50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Ser Ile Pro
                85                  90                  95

Arg Thr Arg Ser Glu Gly Ala Pro Ser Trp Lys
            100                 105

<210> SEQ ID NO 14
<211> LENGTH: 112
<212> TYPE: PRT
<213> ORGANISM: Artificial Sequence
<220> FEATURE:
<223> OTHER INFORMATION: chemically synthesized

<400> SEQUENCE: 14

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 15
<211> LENGTH: 117
<212> TYPE: PRT
<213> ORGANISM: Artificial Sequence
<220> FEATURE:
<223> OTHER INFORMATION: chemically synthesized

<400> SEQUENCE: 15

Val Lys Leu Gln Glu Ser Gly Ala Glu Leu Val Lys Pro Gly Ala Ser
1               5                   10                  15

Val Lys Leu Ser Cys Lys Ala Ser Gly Tyr Thr Phe Thr Ser Tyr Trp
            20                  25                  30

Met His Trp Val Lys Gln Arg Pro Gly Arg Gly Leu Glu Trp Ile Gly
        35                  40                  45

Arg Ile Gly Pro Asn Ser Gly Gly Thr Lys Tyr Asn Glu Lys Phe Lys
50                  55                  60

Ser Lys Ala Thr Leu Thr Val Asp Lys Pro Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Arg Met Val Lys Gly Cys Tyr Gly Leu Leu Gly Pro Arg Asp His

Gly His Arg Leu Leu
        115

<210> SEQ ID NO 16
<211> LENGTH: 117
<212> TYPE: PRT
<213> ORGANISM: Artificial Sequence
<220> FEATURE:
<223> OTHER INFORMATION: chemically synthesized

<400> SEQUENCE: 16

Val Lys Leu Gln Glu Ser Gly Pro Glu Leu Val Lys Pro Gly Ala Ser
1               5                   10                  15

Val Lys Ile Ser Cys Lys Ala Ser Gly Tyr Thr Phe Thr Asp Tyr Tyr
            20                  25                  30

Met Asn Trp Val Lys Gln Ser His Gly Lys Ser Leu Glu Trp Ile Gly
        35                  40                  45

Asp Ile Asn Pro Asn Asn Gly Gly Thr Ser Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Arg Ser Leu Thr Ser Glu Asp Ser Ala Val Tyr Tyr Cys Ala
                85                  90                  95

Arg Tyr Asp Tyr Ala Trp Tyr Phe Asp Val Trp Gly Gln Gly Thr Thr
            100                 105                 110

Val Thr Val Ser Ser
        115

<210> SEQ ID NO 17
<211> LENGTH: 272
<212> TYPE: PRT
<213> ORGANISM: Artificial Sequence
<220> FEATURE:
<223> OTHER INFORMATION: chemically synthesized

<400> SEQUENCE: 17

His His His His His His Val Lys Leu Gln Glu Ser Gly Ala Glu Leu
1               5                   10                  15

Val Lys Pro Gly Ala Ser Val Lys Leu Ser Cys Lys Ala Ser Gly Tyr
            20                  25                  30

Thr Phe Thr Ser Tyr Trp Met His Trp Val Lys Gln Arg Pro Gly Arg
        35                  40                  45

Gly Leu Glu Trp Ile Gly Arg Ile Gly Pro Asn Ser Gly Gly Thr Lys
    50                  55                  60

Tyr Asn Glu Lys Phe Lys Ser Lys Ala Thr Leu Thr Val Asp Lys Pro
65                  70                  75                  80

Ser Ser Thr Ala Tyr Met Gln Leu Ser Ser Leu Thr Ser Glu Asp Ser
                85                  90                  95

Ala Val Tyr Tyr Cys Ala Arg Arg Met Val Lys Gly Cys Tyr Gly Leu
            100                 105                 110

Leu Gly Pro Arg Asp His Gly His Arg Leu Leu Lys Gly Arg Ile Pro
        115                 120                 125

Ala His Trp Arg Pro Leu Leu Val Asp Pro Ser Ser Val Pro Ser Leu
    130                 135                 140

Ala Ser Gly Gly Gly Gly Ser Gly Gly Gly Ser Trp Ile Ser
145                 150                 155                 160

```
Ala Glu Phe Ala Leu Asp Ile Glu Leu Thr Gln Ser Pro Thr Thr Met
                165                 170                 175

Ala Ala Ser Pro Gly Glu Lys Ile Thr Ile Thr Cys Ser Ala Ser Ser
            180                 185                 190

Ser Ile Ser Ser Asn Tyr Leu His Trp Tyr Gln Gln Lys Pro Gly Phe
        195                 200                 205

Ser Pro Lys Leu Leu Ile Tyr Arg Thr Ser Asn Leu Ala Ser Gly Val
    210                 215                 220

Pro Ala Arg Phe Ser Gly Ser Gly Ser Gly Thr Ser Tyr Ser Leu Thr
225                 230                 235                 240

Ile Gly Thr Met Glu Ala Glu Asp Val Ala Thr Tyr Tyr Cys Gln Gln
                245                 250                 255

Gly Ser Ser Ile Pro Arg Thr Arg Ser Glu Gly Ala Pro Ser Trp Lys
            260                 265                 270
```

<210> SEQ ID NO 18
<211> LENGTH: 274
<212> TYPE: PRT
<213> ORGANISM: Artificial Sequence
<220> FEATURE:
<223> OTHER INFORMATION: chemically synthesized

<400> SEQUENCE: 18

```
Met Ser Val Pro Thr Gln Val Leu Gly Leu Leu Leu Leu Trp Leu Thr
1               5                   10                  15

Asp Ala Arg Cys Val Lys Leu Gln Glu Ser Gly Pro Glu Leu Val Lys
                20                  25                  30

Pro Gly Ala Ser Val Lys Ile Ser Cys Lys Ala Ser Gly Tyr Thr Phe
            35                  40                  45

Thr Asp Tyr Tyr Met Asn Trp Val Lys Gln Ser His Gly Lys Ser Leu
        50                  55                  60

Glu Trp Ile Gly Asp Ile Asn Pro Asn Asn Gly Gly Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
                100                 105                 110

Tyr Tyr Cys Ala Arg Tyr Asp Tyr Ala Trp Tyr Phe Asp Val Trp Gly
            115                 120                 125

Gln Gly Thr Thr Val Thr Val Ser Ser Gly Gly Gly Gly Ser Gly Gly
        130                 135                 140

Gly Gly Ser Gly Gly Gly Gly Asp Val Leu Met Thr Gln Thr Pro Leu
145                 150                 155                 160

Ser Leu Pro Val Ser Leu Gly Asp Gln Ala Ser Ile Ser Cys Arg Ser
                165                 170                 175

Ser Gln Ser Ile Val His Ser Asn Gly Asn Thr Tyr Leu Glu Trp Tyr
            180                 185                 190

Leu Gln Lys Pro Gly Gln Ser Pro Lys Leu Leu Ile Tyr Lys Val Ser
        195                 200                 205

Asn Arg Phe Ser Gly Val Pro Asp Arg Phe Ser Gly Ser Gly Ser Gly
    210                 215                 220

Thr Asp Phe Thr Leu Lys Ile Ser Arg Val Glu Ala Glu Asp Leu Gly
225                 230                 235                 240

Val Tyr Tyr Cys Phe Gln Gly Ser His Val Pro Tyr Thr Phe Gly Gly
                245                 250                 255
```

Gly Thr Lys Leu Glu Ile Lys Arg Ile Glu Gly Arg His His His His
        260                 265                 270

His His

<210> SEQ ID NO 19
<211> LENGTH: 321
<212> TYPE: DNA
<213> ORGANISM: Artificial Sequence
<220> FEATURE:
<223> OTHER INFORMATION: chemically synthesized

<400> SEQUENCE: 19
gacattgagc tcacccagtc tccaaccacc atggctgcat ctcccgggga gaagatcact       60
atcacctgca gtgccagctc aagtataagt tccaattact tgcattggta tcagcagaag      120
ccaggattct ccctaaaact cttgatttat aggacatcca atctggcttc tggagtccca      180
gctcgcttca gtggcagtgg gtctgggacc tcttactctc tcacaattgg caccatggag      240
gctgaagatg ttgccactta ctactgccag cagggtagta gtataccacg tacacgttcg      300
gagggggcac aagctggaa a                                                 321

<210> SEQ ID NO 20
<211> LENGTH: 338
<212> TYPE: DNA
<213> ORGANISM: Artificial Sequence
<220> FEATURE:
<223> OTHER INFORMATION: chemically synthesized

<400> SEQUENCE: 20
gatgttttga tgacccaaac tccactctcc ctgcctgtca gtcttggaga tcaagcctcc       60
atctcttgca gatctagtca gagcattgta catagtaatg aaacacccta tttagaatgg      120
tacctgcaga aaccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tattactgct ttcaaggttc acatgttccg      300
tacacgttcg gaggggggac caagctggaa ataaaacg                              338

<210> SEQ ID NO 21
<211> LENGTH: 352
<212> TYPE: DNA
<213> ORGANISM: Artificial Sequence
<220> FEATURE:
<223> OTHER INFORMATION: chemically synthesized

<400> SEQUENCE: 21
gtgaaactgc aggagtcagg ggctgagctt gtgaagcctg ggcttcagt gaagctgtcc        60 tgcaaggctt ctggctacac cttcaccagc tactggatgc actgggtgaa gcagaggcct      120
ggacgaggcc ttgagtggat tggaaggatt ggtcctaata gtggtggtac taagtacaat      180
gagaagttca gagcaaggc cacactgact gtagacaaac cctccagcac agcctacatg       240
cagctcagca gcctgacatc tgaggactct gcggtctatt attgtgcaag aagaatggta      300
aaggggtgct atggactact ggggccaagg gaccacggtc accgtctcct ca              352

<210> SEQ ID NO 22
<211> LENGTH: 351
<212> TYPE: DNA
<213> ORGANISM: Artificial Sequence
<220> FEATURE:
<223> OTHER INFORMATION: chemically synthesized

<400> SEQUENCE: 22

```
gtgaagctgc aggagtctgg acctgagctg gtgaagcctg gggcttcagt gaagatatcc     60
tgtaaggctt ctggatacac gttcactgac tactacatga actgggtgaa gcagagccat    120
ggaaagagcc ttgagtggat tggagatatt aatcctaaca atggtggtac tagctacaac    180
cagaagttca aggcaaggc cacattgact gtagacaagt cctccagcac agcctacatg     240
gagctccgca gcctgacatc tgaggactct gcagtctatt actgtgcaag atatgattac    300
gcttggtact tcgatgtctg gggccaaggg accacggtca ccgtctcctc a             351
```

<210> SEQ ID NO 23
<211> LENGTH: 837
<212> TYPE: DNA
<213> ORGANISM: Artificial Sequence
<220> FEATURE:
<223> OTHER INFORMATION: chemically synthesized

<400> SEQUENCE: 23

```
gccgccacca tgagtgtgcc cactcaggtc ctggggttgc tgctgctgtg gcttacagat     60
gccagatgtg tgaagctgca ggagtctgga cctgagctgg tgaagcctgg ggcttcagtg    120
aagatatcct gtaaggcttc tggatacacg ttcactgact actacatgaa ctgggtgaag    180
cagagccatg gaaagagcct tgagtggatt ggagatatta atcctaacaa tggtggtact    240
agctacaacc agaagttcaa ggcaaggcc acattgactg tagacaagtc ctccagcaca     300
gcctacatgg agctccgcag cctgacatct gaggactctg cagtctatta ctgtgcaaga    360
tatgattacg cttggtactt cgatgtctgg ggccaaggga ccacggtcac cgtctcctca    420
ggcggaggtg ggtcgggtgg cggcggatct ggcggaggtg gggatgtttt gatgacccaa    480
actccactct ccctgcctgt cagtcttgga gatcaagcct ccatctcttg cagatctagt    540
cagagcattg tacatagtaa tggaaacacc tatttagaat ggtacctgca gaaaccaggc    600
cagtctccaa agctcctgat ctacaaagtt tccaaccgat tttctggggt cccagacagg    660
ttcagtggca gtggatcagg gacagatttc acactcaaga tcagcagagt ggaggctgag    720
gatctgggag tttattactg cttttcaaggt tcacatgttc cgtacacgtt cggagggggg    780
accaagctgg aaataaaacg gatcgaaggc cggcatcacc atcatcacca ctgatag       837
```

<210> SEQ ID NO 24
<211> LENGTH: 825
<212> TYPE: DNA
<213> ORGANISM: Artificial Sequence
<220> FEATURE:
<223> OTHER INFORMATION: chemically synthesized

<400> SEQUENCE: 24

```
atgtccgtgc ctacccaggt gctcggactc ctgctgctgt ggctcaccga cgccaggtgt     60
gtgaagctgc aggagagcgg acccgagctg gtgaagcctg agcctccgt gaagatcagc     120
tgcaaggctt ccggatacac cttcaccgac tactatatga ctgggtgaa gcagagccac     180
ggcaagagcc tggagtggat cggcgacatc aaccctaaca acggcggcac ctcctacaac    240
cagaagttca gggcaaggc tacactgacc gtggacaagt cctccagcac cgcctacatg     300
gagctcagga gcctgacctc gaggattcc gccgtctatt actgtgcccg gtacgactac     360
gcctggtatt tcgacgtgtg gggccagggc acaaccgtca cagtctccag cggaggagga    420
ggaagcggcg gcggaggatc cggaggcgga ggcgatgtcc tgatgacaca gacacctctg    480
agcctccccg tgagcctggg agaccaagcc tccatctcct gcaggtcctc ccagtccatc    540
```

```
gtgcacagca atggcaacac ctacctggag tggtatctgc agaagcctgg ccagtccccc    600
aagctgctga tctacaaggt gtccaaccgg ttcagcggcg tccctgacag gttctccgga    660
tccggaagcg gcacagattt caccctgaag atcagcaggg tcgaggccga ggacctggga    720
gtgtactact gcttccaggg ctcccatgtc ccttacacct tcggcggcgg caccaaactg    780
gagatcaagc ggatcgaggg caggcatcac caccatcacc actga                   825
```

```
<210> SEQ ID NO 25
<211> LENGTH: 10
<212> TYPE: PRT
<213> ORGANISM: Artificial Sequence
<220> FEATURE:
<223> OTHER INFORMATION: chemically synthesized

<400> SEQUENCE: 25

Lys Ser Val Ser Thr Ser Gly Tyr Ser Tyr
1               5                   10

<210> SEQ ID NO 26
<211> LENGTH: 3
<212> TYPE: PRT
<213> ORGANISM: Artificial Sequence
<220> FEATURE:
<223> OTHER INFORMATION: chemically synthesized

<400> SEQUENCE: 26

Leu Val Ser
1

<210> SEQ ID NO 27
<211> LENGTH: 16
<212> TYPE: PRT
<213> ORGANISM: Artificial Sequence
<220> FEATURE:
<223> OTHER INFORMATION: chemically synthesized

<400> SEQUENCE: 27

Gln His Ile Arg Glu Leu Thr Arg Ser Glu Gly Gly Pro Ser Trp Lys
1               5                   10                  15

<210> SEQ ID NO 28
<211> LENGTH: 8
<212> TYPE: PRT
<213> ORGANISM: Artificial Sequence
<220> FEATURE:
<223> OTHER INFORMATION: chemically synthesized

<400> SEQUENCE: 28

Gly Tyr Thr Phe Thr Ser Tyr Trp
1               5

<210> SEQ ID NO 29
<211> LENGTH: 8
<212> TYPE: PRT
<213> ORGANISM: Artificial Sequence
<220> FEATURE:
<223> OTHER INFORMATION: chemically synthesized

<400> SEQUENCE: 29

Ile Asn Pro Ser Asn Gly Gly Thr
1               5

<210> SEQ ID NO 30
<211> LENGTH: 12
```

```
<212> TYPE: PRT
<213> ORGANISM: Artificial Sequence
<220> FEATURE:
<223> OTHER INFORMATION: chemically synthesized

<400> SEQUENCE: 30

Ala Arg Arg Gly Ile Arg Leu Arg His Phe Asp Tyr
1               5                   10

<210> SEQ ID NO 31
<211> LENGTH: 6
<212> TYPE: PRT
<213> ORGANISM: Artificial Sequence
<220> FEATURE:
<223> OTHER INFORMATION: chemically synthesized

<400> SEQUENCE: 31

Gln Asp Val Gly Thr Ala
1               5

<210> SEQ ID NO 32
<211> LENGTH: 3
<212> TYPE: PRT
<213> ORGANISM: Artificial Sequence
<220> FEATURE:
<223> OTHER INFORMATION: chemically synthesized

<400> SEQUENCE: 32

Trp Ala Ser
1

<210> SEQ ID NO 33
<211> LENGTH: 9
<212> TYPE: PRT
<213> ORGANISM: Artificial Sequence
<220> FEATURE:
<223> OTHER INFORMATION: chemically synthesized

<400> SEQUENCE: 33

Gln Gln Tyr Ser Ser Tyr Pro Leu Thr
1               5

<210> SEQ ID NO 34
<211> LENGTH: 108
<212> TYPE: PRT
<213> ORGANISM: Artificial Sequence
<220> FEATURE:
<223> OTHER INFORMATION: chemically synthesized

<400> SEQUENCE: 34

Asp Ile Val Met Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

<210> SEQ ID NO 35
<211> LENGTH: 107
<212> TYPE: PRT
<213> ORGANISM: Artificial Sequence
<220> FEATURE:
<223> OTHER INFORMATION: chemically synthesized

<400> SEQUENCE: 35

Asp Ile Gln Met Thr Gln Ser Pro Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Leu
                85                  90                  95

Thr Phe Gly Ala Gly Thr Lys Leu Glu Leu Lys
            100                 105

<210> SEQ ID NO 36
<211> LENGTH: 117
<212> TYPE: PRT
<213> ORGANISM: Artificial Sequence
<220> FEATURE:
<223> OTHER INFORMATION: chemically synthesized

<400> SEQUENCE: 36

Val Lys Leu Gln Glu Ser Gly Thr Glu Leu Val Lys Pro Gly Ala Ser
1               5                   10                  15

Val Lys Leu Ser Cys Lys Ala Ser Gly Tyr Thr Phe Thr Ser Tyr Trp
            20                  25                  30

Met His Trp Val Lys Gln Arg Pro Gly Gln Gly Leu Glu Trp Ile Gly
        35                  40                  45

Asn Ile Asn Pro Ser Asn Gly Gly Thr Asn Tyr Asn Glu Lys Phe Lys
    50                  55                  60

Ser Lys Ala Thr Leu Thr Val Asp Lys Ser Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Arg Gly Ile Arg Leu Arg His Phe Asp Tyr Trp Gly Gln Gly Thr
            100                 105                 110

Thr Val Thr Val Ser
        115

<210> SEQ ID NO 37
<211> LENGTH: 275
<212> TYPE: PRT
<213> ORGANISM: Artificial Sequence
<220> FEATURE:
<223> OTHER INFORMATION: chemically synthesized

<400> SEQUENCE: 37

Val Lys Leu Gln Glu Ser Gly Thr Glu Leu Val Lys Pro Gly Ala Ser
1               5                   10                  15

Val Lys Leu Ser Cys Lys Ala Ser Gly Tyr Thr Phe Thr Ser Tyr Trp
           20                  25                  30

Met His Trp Val Lys Gln Arg Pro Gly Gln Gly Leu Glu Trp Ile Gly
       35                  40                  45

Asn Ile Asn Pro Ser Asn Gly Gly Thr Asn Tyr Asn Glu Lys Phe Lys
    50                  55                  60

Ser Lys Ala Thr Leu Thr Val Asp Lys Ser Ser Ser Thr Ala Tyr Met
65                  70                  75                  80

Gln Leu Ser Ser Leu Thr Ser Glu Asp Ser Ala Val Tyr Tyr Cys Ala
                85                  90                  95

Arg Arg Gly Ile Arg Leu Arg His Phe Asp Tyr Trp Gly Gln Gly Thr
            100                 105                 110

Thr Val Thr Val Ser Ser Arg Ala Asn Ser Ala Asp Ile His His Thr
        115                 120                 125

Gly Gly Arg Ser Ser Met His Leu Glu Gly Pro Ile Arg Pro Ile Val
    130                 135                 140

Ser Arg Ile Ser Gly Gly Gly Gly Ser Gly Gly Gly Gly Ser Trp
145                 150                 155                 160

Ile Ser Ala Glu Phe Ala Leu Asp Ile Val Met Thr Gln Ser Pro Ala
                165                 170                 175

Ser Leu Ala Val Ser Leu Gly Gln Arg Ala Thr Ile Ser Tyr Arg Ala
            180                 185                 190

Ser Lys Ser Val Ser Thr Ser Gly Tyr Ser Tyr Met His Trp Asn Gln
        195                 200                 205

Gln Lys Pro Gly Gln Pro Pro Arg Leu Leu Ile Tyr Leu Val Ser Asn
    210                 215                 220

Leu Glu Ser Gly Val Pro Ala Arg Phe Ser Gly Ser Gly Ser Gly Thr
225                 230                 235                 240

Asp Phe Thr Leu Asn Ile His Pro Val Glu Glu Asp Ala Ala Thr
                245                 250                 255

Tyr Tyr Cys Gln His Ile Arg Glu Leu Thr Arg Ser Glu Gly Gly Pro
            260                 265                 270

Ser Trp Lys
        275

<210> SEQ ID NO 38
<211> LENGTH: 271
<212> TYPE: PRT
<213> ORGANISM: Artificial Sequence
<220> FEATURE:
<223> OTHER INFORMATION: chemically synthesized

<400> SEQUENCE: 38

Met Ser Val Pro Thr Gln Val Leu Gly Leu Leu Leu Leu Trp Leu Thr
1               5                   10                  15

Asp Ala Arg Cys Val Lys Leu Gln Glu Ser Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Leu Thr Val Asp Lys Ser Ser Ser
                85                  90                  95

```
Thr Ala Tyr Met Gln Leu Ser Ser Leu Thr Ser Glu Asp Ser Ala Val
                100                 105                 110

Tyr Tyr Cys Ala Arg Arg Gly Ile Arg Leu Arg His Phe Asp Tyr Trp
        115                 120                 125

Gly Gln Gly Thr Thr Val Thr Val Ser Ser Gly Gly Gly Gly Ser Gly
    130                 135                 140

Gly Gly Gly Ser Gly Gly Gly Ser Asp Ile Gln Met Thr Gln Ser
145                 150                 155                 160

Pro Lys Phe Met Ser Thr Ser Val Gly Asp Arg Val Ser Ile Thr Cys
                165                 170                 175

Lys Ala Ser Gln Asp Val Gly Thr Ala Val Ala Trp Tyr Gln Gln Lys
            180                 185                 190

Pro Gly Gln Ser Pro Lys Leu Leu Ile Tyr Trp Ala Ser Thr Arg His
        195                 200                 205

Thr Gly Val Pro Asp Arg Phe Thr Gly Ser Gly Ser Gly Thr Asp Phe
    210                 215                 220

Thr Leu Thr Ile Ser Asn Val Gln Ser Glu Asp Leu Ala Asp Tyr Phe
225                 230                 235                 240

Cys Gln Gln Tyr Ser Ser Tyr Pro Leu Thr Phe Gly Ala Gly Thr Lys
                245                 250                 255

Leu Glu Leu Lys Arg Ile Glu Gly Arg His His His His His His
            260                 265                 270

<210> SEQ ID NO 39
<211> LENGTH: 324
<212> TYPE: DNA
<213> ORGANISM: Artificial Sequence
<220> FEATURE:
<223> OTHER INFORMATION: chemically synthesized

<400> SEQUENCE: 39
gacattgtga tgacacagtc tcctgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtggg tctgggacag acttcaccct caacatccat   240
cctgtggagg aggaggatgc tgcaacctat tactgtcagc acattaggga gcttacacgt   300
tcggaggggg gaccaagctg gaaa                                          324

<210> SEQ ID NO 40
<211> LENGTH: 322
<212> TYPE: DNA
<213> ORGANISM: Artificial Sequence
<220> FEATURE:
<223> OTHER INFORMATION: chemically synthesized

<400> SEQUENCE: 40
gacatccaga tgacccagtc tcccaaattc atgtccacat cagtaggaga cagggtcagc    60
atcacctgca aggccagtca ggatgtgggt actgctgtag cctggtatca acagaaacca   120
gggcaatctc ctaaactact gatttactgg gcatccaccc ggcacactgg agtccctgat   180
cgcttcacag gcagtggatc tgggacagat ttcactctca ccattagcaa tgtgcagtct   240
gaagacttgg cagattattt ctgtcagcaa tatagcagct atcctctcac gttcggtgct   300
gggaccaagc tggagctgaa ac                                            322

<210> SEQ ID NO 41
```

-continued

<210> SEQ ID NO 41
<211> LENGTH: 351
<212> TYPE: DNA
<213> ORGANISM: Artificial Sequence
<220> FEATURE:
<223> OTHER INFORMATION: chemically synthesized

<400> SEQUENCE: 41

| | | |
|---|---|---|
| gtgaaactgc aggagtctgg gactgaactg gtgaagcctg gggcttcagt gaagctgtcc | 60 |
| tgcaaggctt ctggctacac cttcaccagc tactggatgc actgggtgaa gcagaggcct | 120 |
| ggacaaggcc ttgagtggat tggaaatatt aatcctagca atggtggtac taactacaat | 180 |
| gagaagttca gagcaaggc cacactgact gtagacaaat cctccagcac agcctacatg | 240 |
| cagctcagca gcctgacatc tgaggactct gcggtctatt attgtgcaag aagaggcata | 300 |
| cggttacgac actttgacta ctggggccaa gggaccacgg tcaccgtctc c | 351 |

<210> SEQ ID NO 42
<211> LENGTH: 828
<212> TYPE: DNA
<213> ORGANISM: Artificial Sequence
<220> FEATURE:
<223> OTHER INFORMATION: chemically synthesized

<400> SEQUENCE: 42

| | | |
|---|---|---|
| gccgccacca tgagtgtgcc cactcaggtc ctggggttgc tgctgctgtg gcttacagat | 60 |
| gccagatgtg tgaaactgca ggagtctggg actgaactgg tgaagcctgg ggcttcagtg | 120 |
| aagctgtcct gcaaggcttc tggctacacc ttcaccagct actggatgca ctgggtgaag | 180 |
| cagaggcctg gacaaggcct tgagtggatt ggaaatatta atcctagcaa tggtggtact | 240 |
| aactacaatg agaagttcaa gagcaaggcc acactgactg tagacaaatc ctccagcaca | 300 |
| gcctacatgc agctcagcag cctgacatct gaggactctg cggtctatta ttgtgcaaga | 360 |
| agaggcatac ggttacgaca ctttgactac tggggccaag gaccacggt caccgtctcc | 420 |
| tctggcggag gtgggtcggg tggcggcgga tctggcggag gtgggtcgga catccagatg | 480 |
| acccagtctc ccaaattcat gtccacatca gtaggagaca gggtcagcat cacctgcaag | 540 |
| gccagtcagg atgtgggtac tgctgtagcc tggtatcaac agaaaccagg caatctcct | 600 |
| aaactactga tttactgggc atccaccgg cacactggag tccctgatcg cttcacaggc | 660 |
| agtggatctg gacagattt cactctcacc attagcaatg tgcagtctga agacttggca | 720 |
| gattatttct gtcagcaata tagcagctat cctctcacgt tcggtgctgg gaccaagctg | 780 |
| gagctgaaac ggatcgaagg ccggcatcac catcatcacc actgatag | 828 |

<210> SEQ ID NO 43
<211> LENGTH: 819
<212> TYPE: DNA
<213> ORGANISM: Artificial Sequence
<220> FEATURE:
<223> OTHER INFORMATION: chemically synthesized

<400> SEQUENCE: 43

| | | |
|---|---|---|
| atgagcgtgc ctacacaggt gctcggcctg ctgctcctct ggctgacaga cgcccggtgt | 60 |
| gtgaagctgc aggagtccgg aaccgagctg gtgaaacctg cgccagcgt gaaactgagc | 120 |
| tgcaaagcca gcggatacac cttcacctcc tactggatgc actgggtgaa acagaggcct | 180 |
| ggccagggcc tggaatggat tggcaacatc aaccccagca acggcggcac caactacaat | 240 |
| gagaagttca gagcaaggc cacctgacc gtggataagt cctcctccac cgcctacatg | 300 |
| cagctgtcct ccctcaccct cgaggacagc gccgtctatt actgtgccag gcggggcatc | 360 |

```
aggctgaggc acttcgacta ctggggccaa ggcacaaccg tcaccgtgag ctccggagga    420
ggaggcagcg gaggcggagg ctccggcgga ggcggaagcg acattcagat gacccagagc    480
cccaagttca tgtccacctc cgtcggcgac agggtgagca tcacctgtaa ggccagccag    540
gatgtcggca cagctgtggc ctggtaccag cagaagcccg gccagtcccc caagctgctg    600
atctactggg cttccacaag gcataccggc gtccccgata ggttcacagg ctccggctcc    660
ggcaccgact tcacactcac catcagcaac gtccagtccg aggacctggc cgactacttc    720
tgccagcagt actccagcta ccccctcacc ttcggcgctg gcaccaagct ggaactcaag    780
cggatcgagg gcaggcatca ccaccatcac cactgatag                           819
```

<210> SEQ ID NO 44
<211> LENGTH: 392
<212> TYPE: PRT
<213> ORGANISM: Homo sapiens

<400> SEQUENCE: 44

```
Met Glu Pro Pro Gly Arg Arg Glu Cys Pro Phe Pro Ser Trp Arg Phe
1               5                   10                  15

Pro Gly Leu Leu Leu Ala Ala Met Val Leu Leu Leu Tyr Ser Phe Ser
            20                  25                  30

Asp Ala Cys Glu Glu Pro Pro Thr Phe Glu Ala Met Glu Leu Ile Gly
        35                  40                  45

Lys Pro Lys Pro Tyr Tyr Glu Ile Gly Glu Arg Val Asp Tyr Lys Cys
    50                  55                  60

Lys Lys Gly Tyr Phe Tyr Ile Pro Pro Leu Ala Thr His Thr Ile Cys
65                  70                  75                  80

Asp Arg Asn His Thr Trp Leu Pro Val Ser Asp Ala Cys Tyr Arg
                85                  90                  95

Glu Thr Cys Pro Tyr Ile Arg Asp Pro Leu Asn Gly Gln Ala Val Pro
            100                 105                 110

Ala Asn Gly Thr Tyr Glu Phe Gly Tyr Gln Met His Phe Ile Cys Asn
        115                 120                 125

Glu Gly Tyr Tyr Leu Ile Gly Glu Glu Ile Leu Tyr Cys Glu Leu Lys
    130                 135                 140

Gly Ser Val Ala Ile Trp Ser Gly Lys Pro Pro Ile Cys Glu Lys Val
145                 150                 155                 160

Leu Cys Thr Pro Pro Lys Ile Lys Asn Gly Lys His Thr Phe Ser
            165                 170                 175

Glu Val Glu Val Phe Glu Tyr Leu Asp Ala Val Thr Tyr Ser Cys Asp
            180                 185                 190

Pro Ala Pro Gly Pro Asp Pro Phe Ser Leu Ile Gly Glu Ser Thr Ile
        195                 200                 205

Tyr Cys Gly Asp Asn Ser Val Trp Ser Arg Ala Ala Pro Glu Cys Lys
    210                 215                 220

Val Val Lys Cys Arg Phe Pro Val Val Glu Asn Gly Lys Gln Ile Ser
225                 230                 235                 240

Gly Phe Gly Lys Lys Phe Tyr Tyr Lys Ala Thr Val Met Phe Glu Cys
                245                 250                 255

Asp Lys Gly Phe Tyr Leu Asp Gly Ser Asp Thr Ile Val Cys Asp Ser
            260                 265                 270

Asn Ser Thr Trp Asp Pro Pro Val Pro Lys Cys Leu Lys Val Leu Pro
        275                 280                 285
```

Pro Ser Ser Thr Lys Pro Pro Ala Leu Ser His Ser Val Ser Thr Ser
        290                 295                 300

Ser Thr Thr Lys Ser Pro Ala Ser Ser Ala Ser Gly Pro Arg Pro Thr
305                 310                 315                 320

Tyr Lys Pro Pro Val Ser Asn Tyr Pro Gly Tyr Pro Lys Pro Glu Glu
                325                 330                 335

Gly Ile Leu Asp Ser Leu Asp Val Trp Val Ile Ala Val Ile Val Ile
            340                 345                 350

Ala Ile Val Val Gly Val Ala Val Ile Cys Val Val Pro Tyr Arg Tyr
                355                 360                 365

Leu Gln Arg Arg Lys Lys Gly Thr Tyr Leu Thr Asp Glu Thr His
    370                 375                 380

Arg Glu Val Lys Phe Thr Ser Leu
385                 390

<210> SEQ ID NO 45
<211> LENGTH: 381
<212> TYPE: PRT
<213> ORGANISM: Homo sapiens

<400> SEQUENCE: 45

Met Thr Val Ala Arg Pro Ser Val Pro Ala Leu Pro Leu Leu Gly
1               5                   10                  15

Glu Leu Pro Arg Leu Leu Leu Val Leu Leu Cys Leu Pro Ala Val
            20                  25                  30

Trp Gly Asp Cys Gly Leu Pro Pro Asp Val Pro Asn Ala Gln Pro Ala
                35                  40                  45

Leu Glu Gly Arg Thr Ser Phe Pro Glu Asp Thr Val Ile Thr Tyr Lys
    50                  55                  60

Cys Glu Glu Ser Phe Val Lys Ile Pro Gly Glu Lys Asp Ser Val Ile
65                  70                  75                  80

Cys Leu Lys Gly Ser Gln Trp Ser Asp Ile Glu Glu Phe Cys Asn Arg
                85                  90                  95

Ser Cys Glu Val Pro Thr Arg Leu Asn Ser Ala Ser Leu Lys Gln Pro
            100                 105                 110

Tyr Ile Thr Gln Asn Tyr Phe Pro Val Gly Thr Val Val Glu Tyr Glu
        115                 120                 125

Cys Arg Pro Gly Tyr Arg Arg Glu Pro Ser Leu Ser Pro Lys Leu Thr
    130                 135                 140

Cys Leu Gln Asn Leu Lys Trp Ser Thr Ala Val Glu Phe Cys Lys Lys
145                 150                 155                 160

Lys Ser Cys Pro Asn Pro Gly Glu Ile Arg Asn Gly Gln Ile Asp Val
                165                 170                 175

Pro Gly Gly Ile Leu Phe Gly Ala Thr Ile Ser Phe Ser Cys Asn Thr
            180                 185                 190

Gly Tyr Lys Leu Phe Gly Ser Thr Ser Ser Phe Cys Leu Ile Ser Gly
        195                 200                 205

Ser Ser Val Gln Trp Ser Asp Pro Leu Pro Glu Cys Arg Glu Ile Tyr
    210                 215                 220

Cys Pro Ala Pro Pro Gln Ile Asp Asn Gly Ile Ile Gln Gly Glu Arg
225                 230                 235                 240

Asp His Tyr Gly Tyr Arg Gln Ser Val Thr Tyr Ala Cys Asn Lys Gly
                245                 250                 255

Phe Thr Met Ile Gly Glu His Ser Ile Tyr Cys Thr Val Asn Asn Asp
            260                 265                 270

```
Glu Gly Glu Trp Ser Gly Pro Pro Glu Cys Arg Gly Lys Ser Leu
            275                 280                 285

Thr Ser Lys Val Pro Pro Thr Val Gln Lys Pro Thr Thr Val Asn Val
    290                 295                 300

Pro Thr Thr Glu Val Ser Pro Thr Ser Gln Lys Thr Thr Thr Lys Thr
305                 310                 315                 320

Thr Thr Pro Asn Ala Gln Ala Thr Arg Ser Thr Pro Val Ser Arg Thr
                325                 330                 335

Thr Lys His Phe His Glu Thr Thr Pro Asn Lys Gly Ser Gly Thr Thr
                340                 345                 350

Ser Gly Thr Thr Arg Leu Leu Ser Gly His Thr Cys Phe Thr Leu Thr
            355                 360                 365

Gly Leu Leu Gly Thr Leu Val Thr Met Gly Leu Leu Thr
        370                 375                 380

<210> SEQ ID NO 46
<211> LENGTH: 390
<212> TYPE: PRT
<213> ORGANISM: Mus musculus

<400> SEQUENCE: 46

Met Ile Arg Gly Arg Ala Pro Arg Thr Arg Pro Ser Pro Pro Pro Pro
1               5                   10                  15

Leu Leu Pro Leu Leu Ser Leu Ser Leu Leu Leu Ser Pro Thr Val
                20                  25                  30

Arg Gly Asp Cys Gly Pro Pro Asp Ile Pro Asn Ala Arg Pro Ile
            35                  40                  45

Leu Gly Arg His Ser Lys Phe Ala Glu Gln Ser Lys Val Ala Tyr Ser
    50                  55                  60

Cys Asn Asn Gly Phe Lys Gln Val Pro Asp Lys Ser Asn Ile Val Val
65                  70                  75                  80

Cys Leu Glu Asn Gly Gln Trp Ser Ser His Glu Thr Phe Cys Glu Lys
                85                  90                  95

Ser Cys Val Ala Pro Glu Arg Leu Ser Phe Ala Ser Leu Lys Lys Glu
            100                 105                 110

Tyr Leu Asn Met Asn Phe Phe Pro Val Gly Thr Ile Val Glu Tyr Glu
        115                 120                 125

Cys Arg Pro Gly Phe Arg Lys Gln Pro Pro Leu Pro Gly Lys Ala Thr
    130                 135                 140

Cys Leu Glu Asp Leu Val Trp Ser Pro Val Ala Gln Phe Cys Lys Lys
145                 150                 155                 160

Lys Ser Cys Pro Asn Pro Lys Asp Leu Asp Asn Gly His Ile Asn Ile
                165                 170                 175

Pro Thr Gly Ile Leu Phe Gly Ser Glu Ile Asn Phe Ser Cys Asn Pro
            180                 185                 190

Gly Tyr Arg Leu Val Gly Val Ser Ser Thr Phe Cys Ser Val Thr Gly
        195                 200                 205

Asn Thr Val Asp Trp Asp Asp Glu Phe Pro Val Cys Thr Glu Ile His
    210                 215                 220

Cys Pro Glu Pro Pro Lys Ile Asn Asn Gly Ile Met Arg Gly Glu Ser
225                 230                 235                 240

Asp Ser Tyr Thr Tyr Ser Gln Val Val Thr Tyr Ser Cys Asp Lys Gly
                245                 250                 255

Phe Ile Leu Val Gly Asn Ala Ser Ile Tyr Cys Thr Val Ser Lys Ser
```

```
                260                 265                 270
Asp Val Gly Gln Trp Ser Ser Pro Pro Arg Cys Ile Glu Lys Ser
            275                 280                 285

Lys Val Pro Thr Lys Pro Thr Ile Asn Val Pro Ser Thr Gly Thr
            290                 295                 300

Pro Ser Thr Pro Gln Lys Pro Thr Glu Ser Val Pro Asn Pro Gly
305                 310                 315                 320

Asp Gln Pro Thr Pro Gln Lys Pro Ser Thr Val Lys Val Ser Ala Thr
                325                 330                 335

Gln His Val Pro Val Thr Lys Thr Thr Val Arg His Pro Ile Arg Thr
            340                 345                 350

Ser Thr Asp Lys Gly Glu Pro Asn Thr Gly Gly Asp Arg Tyr Ile Tyr
            355                 360                 365

Gly His Thr Cys Leu Ile Thr Leu Thr Val Leu His Val Met Leu Ser
            370                 375                 380

Leu Ile Gly Tyr Leu Thr
385                 390

<210> SEQ ID NO 47
<211> LENGTH: 128
<212> TYPE: PRT
<213> ORGANISM: Homo sapiens

<400> SEQUENCE: 47

Met Gly Ile Gln Gly Gly Ser Val Leu Phe Gly Leu Leu Val Leu
1               5                   10                  15

Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
            35                  40                  45

Asp Ala Cys Leu Ile Thr Lys Ala Gly Leu Gln Val Tyr Asn Lys Cys
            50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Asn Gly Gly Thr Ser Leu Ser Glu Lys Thr Val
            100                 105                 110

Leu Leu Leu Val Thr Pro Phe Leu Ala Ala Ala Trp Ser Leu His Pro
            115                 120                 125

<210> SEQ ID NO 48
<211> LENGTH: 123
<212> TYPE: PRT
<213> ORGANISM: Mus musculus

<400> SEQUENCE: 48

Met Arg Ala Gln Arg Gly Leu Ile Leu Leu Leu Leu Leu Ala Val
1               5                   10                  15

Phe Cys Ser Thr Ala Val Ser Leu Thr Cys Tyr His Cys Phe Gln Pro
            20                  25                  30

Val Val Ser Ser Cys Asn Met Asn Ser Thr Cys Ser Pro Asp Gln Asp
            35                  40                  45

Ser Cys Leu Tyr Ala Val Ala Gly Met Gln Val Tyr Gln Arg Cys Trp
            50                  55                  60

Lys Gln Ser Asp Cys His Gly Glu Ile Ile Met Asp Gln Leu Glu Glu
```

```
                65                  70                  75                  80
Thr Lys Leu Lys Phe Arg Cys Cys Gln Phe Asn Leu Cys Asn Lys Ser
                    85                  90                  95
Asp Gly Ser Leu Gly Lys Thr Pro Leu Leu Gly Thr Ser Val Leu Val
                    100                 105                 110
Ala Ile Leu Asn Leu Cys Phe Leu Ser His Leu
                    115                 120

<210> SEQ ID NO 49
<211> LENGTH: 129
<212> TYPE: PRT
<213> ORGANISM: Mus musculus

<400> SEQUENCE: 49

Met Arg Ala Gln Arg Gly Leu Ile Leu Leu Leu Leu Leu Ala Val
1               5                   10                  15
Phe Cys Ser Thr Ala Val Ser Leu Lys Cys Tyr Asn Cys Phe Gln Phe
                    20                  25                  30
Val Ser Ser Cys Lys Ile Asn Thr Thr Cys Ser Pro Asn Leu Asp Ser
                    35                  40                  45
Cys Leu Tyr Ala Val Ala Gly Arg Gln Val Tyr Gln Gln Cys Trp Lys
        50                  55                  60
Leu Ser Asp Cys Asn Ser Asn Tyr Ile Met Ser Arg Leu Asp Val Ala
65                  70                  75                  80
Gly Ile Gln Ser Lys Cys Cys Gln Trp Gly Leu Cys Asn Lys Asn Leu
                    85                  90                  95
Asp Gly Leu Glu Glu Pro Asn Asn Ala Glu Thr Ser Ser Leu Arg Lys
                    100                 105                 110
Thr Ala Leu Leu Gly Thr Ser Val Leu Val Ala Ile Leu Lys Phe Cys
                    115                 120                 125
Phe

<210> SEQ ID NO 50
<211> LENGTH: 483
<212> TYPE: PRT
<213> ORGANISM: Mus musculus

<400> SEQUENCE: 50

Met Glu Val Ser Ser Arg Ser Ser Glu Pro Leu Asp Pro Val Trp Leu
1               5                   10                  15
Leu Val Ala Phe Gly Arg Gly Gly Val Lys Leu Glu Val Leu Leu Leu
                    20                  25                  30
Phe Leu Leu Pro Phe Thr Leu Gly Glu Leu Arg Gly Gly Leu Gly Lys
                    35                  40                  45
His Gly His Thr Val His Arg Glu Pro Ala Val Asn Arg Leu Cys Ala
        50                  55                  60
Asp Ser Lys Arg Trp Ser Gly Leu Pro Val Ser Ala Gln Arg Pro Phe
65                  70                  75                  80
Pro Met Gly His Cys Pro Ala Pro Ser Gln Leu Pro Ser Ala Lys Pro
                    85                  90                  95
Ile Asn Leu Thr Asp Glu Ser Met Phe Pro Ile Gly Tyr Leu Leu
                    100                 105                 110
Tyr Glu Cys Leu Pro Gly Tyr Ile Lys Arg Gln Phe Ser Ile Thr Cys
                    115                 120                 125
Lys Gln Asp Ser Thr Trp Thr Ser Ala Glu Asp Lys Cys Ile Arg Lys
                    130                 135                 140
```

Gln Cys Lys Thr Pro Ser Asp Pro Glu Asn Gly Leu Val His Val His
145                 150                 155                 160

Thr Gly Ile Gln Phe Gly Ser Arg Ile Asn Tyr Thr Cys Asn Gln Gly
                165                 170                 175

Tyr Arg Leu Ile Gly Ser Ser Ala Val Cys Val Ile Thr Asp Gln
            180                 185                 190

Ser Val Asp Trp Asp Thr Glu Ala Pro Ile Cys Glu Trp Ile Pro Cys
                195                 200                 205

Glu Ile Pro Pro Gly Ile Pro Asn Gly Asp Phe Phe Ser Ser Thr Arg
210                 215                 220

Glu Asp Phe His Tyr Gly Met Val Val Thr Tyr Arg Cys Asn Thr Asp
225                 230                 235                 240

Ala Arg Gly Lys Ala Leu Phe Asn Leu Val Gly Glu Pro Ser Leu Tyr
            245                 250                 255

Cys Thr Ser Asn Asp Gly Glu Ile Gly Val Trp Ser Gly Pro Pro Pro
            260                 265                 270

Gln Cys Ile Glu Leu Asn Lys Cys Thr Pro Pro Tyr Val Glu Asn
            275                 280                 285

Ala Val Met Leu Ser Glu Asn Arg Ser Leu Phe Ser Leu Arg Asp Ile
290                 295                 300

Val Glu Phe Arg Cys His Pro Gly Phe Ile Met Lys Gly Ala Ser Ser
305                 310                 315                 320

Val His Cys Gln Ser Leu Asn Lys Trp Glu Pro Glu Leu Pro Ser Cys
                325                 330                 335

Phe Lys Gly Val Ile Cys Arg Leu Pro Gln Glu Met Ser Gly Phe Gln
            340                 345                 350

Lys Gly Leu Gly Met Lys Lys Glu Tyr Tyr Tyr Gly Glu Asn Val Thr
            355                 360                 365

Leu Glu Cys Glu Asp Gly Tyr Thr Leu Glu Gly Ser Ser Gln Ser Gln
370                 375                 380

Cys Gln Ser Asp Gly Ser Trp Asn Pro Leu Leu Ala Lys Cys Val Ser
385                 390                 395                 400

Arg Ser Ile Ser Gly Leu Ile Val Gly Ile Phe Ile Gly Ile Ile Val
                405                 410                 415

Phe Ile Leu Val Ile Ile Val Phe Ile Trp Met Ile Leu Lys Tyr Lys
                420                 425                 430

Lys Arg Asn Thr Thr Asp Glu Lys Tyr Lys Glu Val Gly Ile His Leu
            435                 440                 445

Asn Tyr Lys Glu Asp Ser Cys Val Arg Leu Gln Ser Leu Leu Thr Ser
            450                 455                 460

Gln Glu Asn Ser Ser Thr Thr Ser Pro Ala Arg Asn Ser Leu Thr Gln
465                 470                 475                 480

Glu Val Ser

<210> SEQ ID NO 51
<211> LENGTH: 2039
<212> TYPE: PRT
<213> ORGANISM: Homo sapiens

<400> SEQUENCE: 51

Met Gly Ala Ser Ser Pro Arg Ser Pro Glu Pro Val Gly Pro Pro Ala
1               5                   10                  15

Pro Gly Leu Pro Phe Cys Cys Gly Gly Ser Leu Leu Ala Val Val Val
            20                  25                  30

Leu Leu Ala Leu Pro Val Ala Trp Gly Gln Cys Asn Ala Pro Glu Trp
        35                  40                  45

Leu Pro Phe Ala Arg Pro Thr Asn Leu Thr Asp Glu Phe Glu Phe Pro
 50                  55                  60

Ile Gly Thr Tyr Leu Asn Tyr Glu Cys Arg Pro Gly Tyr Ser Gly Arg
 65                  70                  75                  80

Pro Phe Ser Ile Ile Cys Leu Lys Asn Ser Val Trp Thr Gly Ala Lys
                 85                  90                  95

Asp Arg Cys Arg Arg Lys Ser Cys Arg Asn Pro Pro Asp Pro Val Asn
             100                 105                 110

Gly Met Val His Val Ile Lys Gly Ile Gln Phe Gly Ser Gln Ile Lys
             115                 120                 125

Tyr Ser Cys Thr Lys Gly Tyr Arg Leu Ile Gly Ser Ser Ser Ala Thr
             130                 135                 140

Cys Ile Ile Ser Gly Asp Thr Val Ile Trp Asp Asn Glu Thr Pro Ile
145                 150                 155                 160

Cys Asp Arg Ile Pro Cys Gly Leu Pro Pro Thr Ile Thr Asn Gly Asp
                 165                 170                 175

Phe Ile Ser Thr Asn Arg Glu Asn Phe His Tyr Gly Ser Val Val Thr
             180                 185                 190

Tyr Arg Cys Asn Pro Gly Ser Gly Gly Arg Lys Val Phe Glu Leu Val
             195                 200                 205

Gly Glu Pro Ser Ile Tyr Cys Thr Ser Asn Asp Asp Gln Val Gly Ile
             210                 215                 220

Trp Ser Gly Pro Ala Pro Gln Cys Ile Ile Pro Asn Lys Cys Thr Pro
225                 230                 235                 240

Pro Asn Val Glu Asn Gly Ile Leu Val Ser Asp Asn Arg Ser Leu Phe
                 245                 250                 255

Ser Leu Asn Glu Val Val Glu Phe Arg Cys Gln Pro Gly Phe Val Met
             260                 265                 270

Lys Gly Pro Arg Arg Val Lys Cys Gln Ala Leu Asn Lys Trp Glu Pro
             275                 280                 285

Glu Leu Pro Ser Cys Ser Arg Val Cys Gln Pro Pro Asp Val Leu
             290                 295                 300

His Ala Glu Arg Thr Gln Arg Asp Lys Asp Asn Phe Ser Pro Gly Gln
305                 310                 315                 320

Glu Val Phe Tyr Ser Cys Glu Pro Gly Tyr Asp Leu Arg Gly Ala Ala
                 325                 330                 335

Ser Met Arg Cys Thr Pro Gln Gly Asp Trp Ser Pro Ala Ala Pro Thr
             340                 345                 350

Cys Glu Val Lys Ser Cys Asp Asp Phe Met Gly Gln Leu Leu Asn Gly
             355                 360                 365

Arg Val Leu Phe Pro Val Asn Leu Gln Leu Gly Ala Lys Val Asp Phe
370                 375                 380

Val Cys Asp Glu Gly Phe Gln Leu Lys Gly Ser Ser Ala Ser Tyr Cys
385                 390                 395                 400

Val Leu Ala Gly Met Glu Ser Leu Trp Asn Ser Ser Val Pro Val Cys
                 405                 410                 415

Glu Gln Ile Phe Cys Pro Ser Pro Val Ile Pro Asn Gly Arg His
             420                 425                 430

Thr Gly Lys Pro Leu Glu Val Phe Pro Phe Gly Lys Ala Val Asn Tyr
             435                 440                 445

-continued

```
Thr Cys Asp Pro His Pro Asp Arg Gly Thr Ser Phe Asp Leu Ile Gly
    450                 455                 460
Glu Ser Thr Ile Arg Cys Thr Ser Asp Pro Gln Gly Asn Gly Val Trp
465                 470                 475                 480
Ser Ser Pro Ala Pro Arg Cys Gly Ile Leu Gly His Cys Gln Ala Pro
                485                 490                 495
Asp His Phe Leu Phe Ala Lys Leu Lys Thr Gln Thr Asn Ala Ser Asp
                500                 505                 510
Phe Pro Ile Gly Thr Ser Leu Lys Tyr Glu Cys Arg Pro Glu Tyr Tyr
                515                 520                 525
Gly Arg Pro Phe Ser Ile Thr Cys Leu Asp Asn Leu Val Trp Ser Ser
530                 535                 540
Pro Lys Asp Val Cys Lys Arg Lys Ser Cys Lys Thr Pro Pro Asp Pro
545                 550                 555                 560
Val Asn Gly Met Val His Val Ile Thr Asp Ile Gln Val Gly Ser Arg
                565                 570                 575
Ile Asn Tyr Ser Cys Thr Thr Gly His Arg Leu Ile Gly His Ser Ser
                580                 585                 590
Ala Glu Cys Ile Leu Ser Gly Asn Ala Ala His Trp Ser Thr Lys Pro
                595                 600                 605
Pro Ile Cys Gln Arg Ile Pro Cys Gly Leu Pro Pro Thr Ile Ala Asn
        610                 615                 620
Gly Asp Phe Ile Ser Thr Asn Arg Glu Asn Phe His Tyr Gly Ser Val
625                 630                 635                 640
Val Thr Tyr Arg Cys Asn Pro Gly Ser Gly Gly Arg Lys Val Phe Glu
                645                 650                 655
Leu Val Gly Glu Pro Ser Ile Tyr Cys Thr Ser Asn Asp Asp Gln Val
                660                 665                 670
Gly Ile Trp Ser Gly Pro Ala Pro Gln Cys Ile Ile Pro Asn Lys Cys
        675                 680                 685
Thr Pro Pro Asn Val Glu Asn Gly Ile Leu Val Ser Asp Asn Arg Ser
        690                 695                 700
Leu Phe Ser Leu Asn Glu Val Val Glu Phe Arg Cys Gln Pro Gly Phe
705                 710                 715                 720
Val Met Lys Gly Pro Arg Arg Val Lys Cys Gln Ala Leu Asn Lys Trp
                725                 730                 735
Glu Pro Glu Leu Pro Ser Cys Ser Arg Val Cys Gln Pro Pro Pro Asp
                740                 745                 750
Val Leu His Ala Glu Arg Thr Gln Arg Asp Lys Asp Asn Phe Ser Pro
        755                 760                 765
Gly Gln Glu Val Phe Tyr Ser Cys Glu Pro Gly Tyr Asp Leu Arg Gly
770                 775                 780
Ala Ala Ser Met Arg Cys Thr Pro Gln Gly Asp Trp Ser Pro Ala Ala
785                 790                 795                 800
Pro Thr Cys Glu Val Lys Ser Cys Asp Asp Phe Met Gly Gln Leu Leu
                805                 810                 815
Asn Gly Arg Val Leu Phe Pro Val Asn Leu Gln Leu Gly Ala Lys Val
                820                 825                 830
Asp Phe Val Cys Asp Glu Gly Phe Gln Leu Lys Gly Ser Ser Ala Ser
                835                 840                 845
Tyr Cys Val Leu Ala Gly Met Glu Ser Leu Trp Asn Ser Ser Val Pro
850                 855                 860
Val Cys Glu Gln Ile Phe Cys Pro Ser Pro Pro Val Ile Pro Asn Gly
```

-continued

```
                865                 870                 875                 880
            Arg His Thr Gly Lys Pro Leu Glu Val Phe Pro Phe Gly Lys Ala Val
                        885                 890                 895
            Asn Tyr Thr Cys Asp Pro His Pro Asp Arg Gly Thr Ser Phe Asp Leu
                        900                 905                 910
            Ile Gly Glu Ser Thr Ile Arg Cys Thr Ser Asp Pro Gln Gly Asn Gly
                        915                 920                 925
            Val Trp Ser Ser Pro Ala Pro Arg Cys Gly Ile Leu Gly His Cys Gln
            930                 935                 940
            Ala Pro Asp His Phe Leu Phe Ala Lys Leu Lys Thr Gln Thr Asn Ala
            945                 950                 955                 960
            Ser Asp Phe Pro Ile Gly Thr Ser Leu Lys Tyr Glu Cys Arg Pro Glu
                        965                 970                 975
            Tyr Tyr Gly Arg Pro Phe Ser Ile Thr Cys Leu Asp Asn Leu Val Trp
                        980                 985                 990
            Ser Ser Pro Lys Asp Val Cys Lys Arg Lys Ser Cys Lys Thr Pro Pro
                        995                 1000                1005
            Asp Pro Val Asn Gly Met Val His Val Ile Thr Asp Ile Gln Val
            1010                1015                1020
            Gly Ser Arg Ile Asn Tyr Ser Cys Thr Thr Gly His Arg Leu Ile
            1025                1030                1035
            Gly His Ser Ser Ala Glu Cys Ile Leu Ser Gly Asn Thr Ala His
            1040                1045                1050
            Trp Ser Thr Lys Pro Pro Ile Cys Gln Arg Ile Pro Cys Gly Leu
            1055                1060                1065
            Pro Pro Thr Ile Ala Asn Gly Asp Phe Ile Ser Thr Asn Arg Glu
            1070                1075                1080
            Asn Phe His Tyr Gly Ser Val Val Thr Tyr Arg Cys Asn Leu Gly
            1085                1090                1095
            Ser Arg Gly Arg Lys Val Phe Glu Leu Val Gly Glu Pro Ser Ile
            1100                1105                1110
            Tyr Cys Thr Ser Asn Asp Asp Gln Val Gly Ile Trp Ser Gly Pro
            1115                1120                1125
            Ala Pro Gln Cys Ile Ile Pro Asn Lys Cys Thr Pro Pro Asn Val
            1130                1135                1140
            Glu Asn Gly Ile Leu Val Ser Asp Asn Arg Ser Leu Phe Ser Leu
            1145                1150                1155
            Asn Glu Val Val Glu Phe Arg Cys Gln Pro Gly Phe Val Met Lys
            1160                1165                1170
            Gly Pro Arg Arg Val Lys Cys Gln Ala Leu Asn Lys Trp Glu Pro
            1175                1180                1185
            Glu Leu Pro Ser Cys Ser Arg Val Cys Gln Pro Pro Pro Glu Ile
            1190                1195                1200
            Leu His Gly Glu His Thr Pro Ser His Gln Asp Asn Phe Ser Pro
            1205                1210                1215
            Gly Gln Glu Val Phe Tyr Ser Cys Glu Pro Gly Tyr Asp Leu Arg
            1220                1225                1230
            Gly Ala Ala Ser Leu His Cys Thr Pro Gln Gly Asp Trp Ser Pro
            1235                1240                1245
            Glu Ala Pro Arg Cys Ala Val Lys Ser Cys Asp Asp Phe Leu Gly
            1250                1255                1260
            Gln Leu Pro His Gly Arg Val Leu Phe Pro Leu Asn Leu Gln Leu
            1265                1270                1275
```

```
Gly Ala Lys Val Ser Phe Val Cys Asp Glu Gly Phe Arg Leu Lys
    1280            1285            1290

Gly Ser Ser Val Ser His Cys Val Leu Val Gly Met Arg Ser Leu
    1295            1300            1305

Trp Asn Asn Ser Val Pro Val Cys Glu His Ile Phe Cys Pro Asn
    1310            1315            1320

Pro Pro Ala Ile Leu Asn Gly Arg His Thr Gly Thr Pro Ser Gly
    1325            1330            1335

Asp Ile Pro Tyr Gly Lys Glu Ile Ser Tyr Thr Cys Asp Pro His
    1340            1345            1350

Pro Asp Arg Gly Met Thr Phe Asn Leu Ile Gly Glu Ser Thr Ile
    1355            1360            1365

Arg Cys Thr Ser Asp Pro His Gly Asn Gly Val Trp Ser Ser Pro
    1370            1375            1380

Ala Pro Arg Cys Glu Leu Ser Val Arg Ala Gly His Cys Lys Thr
    1385            1390            1395

Pro Glu Gln Phe Pro Phe Ala Ser Pro Thr Ile Pro Ile Asn Asp
    1400            1405            1410

Phe Glu Phe Pro Val Gly Thr Ser Leu Asn Tyr Glu Cys Arg Pro
    1415            1420            1425

Gly Tyr Phe Gly Lys Met Phe Ser Ile Ser Cys Leu Glu Asn Leu
    1430            1435            1440

Val Trp Ser Ser Val Glu Asp Asn Cys Arg Arg Lys Ser Cys Gly
    1445            1450            1455

Pro Pro Pro Glu Pro Phe Asn Gly Met Val His Ile Asn Thr Asp
    1460            1465            1470

Thr Gln Phe Gly Ser Thr Val Asn Tyr Ser Cys Asn Glu Gly Phe
    1475            1480            1485

Arg Leu Ile Gly Ser Pro Ser Thr Thr Cys Leu Val Ser Gly Asn
    1490            1495            1500

Asn Val Thr Trp Asp Lys Lys Ala Pro Ile Cys Glu Ile Ile Ser
    1505            1510            1515

Cys Glu Pro Pro Pro Thr Ile Ser Asn Gly Asp Phe Tyr Ser Asn
    1520            1525            1530

Asn Arg Thr Ser Phe His Asn Gly Thr Val Val Thr Tyr Gln Cys
    1535            1540            1545

His Thr Gly Pro Asp Gly Glu Gln Leu Phe Glu Leu Val Gly Glu
    1550            1555            1560

Arg Ser Ile Tyr Cys Thr Ser Lys Asp Asp Gln Val Gly Val Trp
    1565            1570            1575

Ser Ser Pro Pro Pro Arg Cys Ile Ser Thr Asn Lys Cys Thr Ala
    1580            1585            1590

Pro Glu Val Glu Asn Ala Ile Arg Val Pro Gly Asn Arg Ser Phe
    1595            1600            1605

Phe Ser Leu Thr Glu Ile Ile Arg Phe Arg Cys Gln Pro Gly Phe
    1610            1615            1620

Val Met Val Gly Ser His Thr Val Gln Cys Gln Thr Asn Gly Arg
    1625            1630            1635

Trp Gly Pro Lys Leu Pro His Cys Ser Arg Val Cys Gln Pro Pro
    1640            1645            1650

Pro Glu Ile Leu His Gly Glu His Thr Leu Ser His Gln Asp Asn
    1655            1660            1665
```

Phe Ser Pro Gly Gln Glu Val Phe Tyr Ser Cys Glu Pro Ser Tyr
1670            1675                1680

Asp Leu Arg Gly Ala Ala Ser Leu His Cys Thr Pro Gln Gly Asp
1685            1690                1695

Trp Ser Pro Glu Ala Pro Arg Cys Thr Val Lys Ser Cys Asp Asp
1700            1705                1710

Phe Leu Gly Gln Leu Pro His Gly Arg Val Leu Leu Pro Leu Asn
1715            1720                1725

Leu Gln Leu Gly Ala Lys Val Ser Phe Val Cys Asp Glu Gly Phe
1730            1735                1740

Arg Leu Lys Gly Arg Ser Ala Ser His Cys Val Leu Ala Gly Met
1745            1750                1755

Lys Ala Leu Trp Asn Ser Ser Val Pro Val Cys Glu Gln Ile Phe
1760            1765                1770

Cys Pro Asn Pro Pro Ala Ile Leu Asn Gly Arg His Thr Gly Thr
1775            1780                1785

Pro Phe Gly Asp Ile Pro Tyr Gly Lys Glu Ile Ser Tyr Ala Cys
1790            1795                1800

Asp Thr His Pro Asp Arg Gly Met Thr Phe Asn Leu Ile Gly Glu
1805            1810                1815

Ser Ser Ile Arg Cys Thr Ser Asp Pro Gln Gly Asn Gly Val Trp
1820            1825                1830

Ser Ser Pro Ala Pro Arg Cys Glu Leu Ser Val Pro Ala Ala Cys
1835            1840                1845

Pro His Pro Pro Lys Ile Gln Asn Gly His Tyr Ile Gly Gly His
1850            1855                1860

Val Ser Leu Tyr Leu Pro Gly Met Thr Ile Ser Tyr Thr Cys Asp
1865            1870                1875

Pro Gly Tyr Leu Leu Val Gly Lys Gly Phe Ile Phe Cys Thr Asp
1880            1885                1890

Gln Gly Ile Trp Ser Gln Leu Asp His Tyr Cys Lys Glu Val Asn
1895            1900                1905

Cys Ser Phe Pro Leu Phe Met Asn Gly Ile Ser Lys Glu Leu Glu
1910            1915                1920

Met Lys Lys Val Tyr His Tyr Gly Asp Tyr Val Thr Leu Lys Cys
1925            1930                1935

Glu Asp Gly Tyr Thr Leu Glu Gly Ser Pro Trp Ser Gln Cys Gln
1940            1945                1950

Ala Asp Asp Arg Trp Asp Pro Pro Leu Ala Lys Cys Thr Ser Arg
1955            1960                1965

Ala His Asp Ala Leu Ile Val Gly Thr Leu Ser Gly Thr Ile Phe
1970            1975                1980

Phe Ile Leu Leu Ile Ile Phe Leu Ser Trp Ile Ile Leu Lys His
1985            1990                1995

Arg Lys Gly Asn Asn Ala His Glu Asn Pro Lys Glu Val Ala Ile
2000            2005                2010

His Leu His Ser Gln Gly Gly Ser Ser Val His Pro Arg Thr Leu
2015            2020                2025

Gln Thr Asn Glu Glu Asn Ser Arg Val Leu Pro
2030            2035

<210> SEQ ID NO 52
<211> LENGTH: 1231
<212> TYPE: PRT

-continued

<213> ORGANISM: Homo sapiens

<400> SEQUENCE: 52

Met Arg Leu Leu Ala Lys Ile Ile Cys Leu Met Leu Trp Ala Ile Cys
1               5                   10                  15

Val Ala Glu Asp Cys Asn Glu Leu Pro Pro Arg Arg Asn Thr Glu Ile
            20                  25                  30

Leu Thr Gly Ser Trp Ser Asp Gln Thr Tyr Pro Glu Gly Thr Gln Ala
        35                  40                  45

Ile Tyr Lys Cys Arg Pro Gly Tyr Arg Ser Leu Gly Asn Val Ile Met
    50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
            100                 105                 110

Thr Cys Asn Glu Gly Tyr Gln Leu Leu Gly Glu Ile Asn Tyr Arg Glu
        115                 120                 125

Cys Asp Thr Asp Gly Trp Thr Asn Asp Ile Pro Ile Cys Glu Val Val
130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
            180                 185                 190

Ser Asp Asp Gly Phe Trp Ser Lys Glu Lys Pro Lys Cys Val Glu Ile
        195                 200                 205

Ser Cys Lys Ser Pro Asp Val Ile Asn Gly Ser Pro Ile Ser Gln Lys
210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
            260                 265                 270

Pro Asn Gly Asp Tyr Ser Pro Leu Arg Ile Lys His Arg Thr Gly Asp
        275                 280                 285

Glu Ile Thr Tyr Gln Cys Arg Asn Gly Phe Tyr Pro Ala Thr Arg Gly
290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
            340                 345                 350

Tyr Ser Tyr Tyr Cys Asp Glu His Phe Glu Thr Pro Ser Gly Ser Tyr
        355                 360                 365

Trp Asp His Ile His Cys Thr Gln Asp Gly Trp Ser Pro Ala Val Pro
370                 375                 380

Cys Leu Arg Lys Cys Tyr Phe Pro Tyr Leu Glu Asn Gly Tyr Asn Gln
385                 390                 395                 400

```
Asn Tyr Gly Arg Lys Phe Val Gln Gly Lys Ser Ile Asp Val Ala Cys
            405                 410                 415
His Pro Gly Tyr Ala Leu Pro Lys Ala Gln Thr Thr Val Thr Cys Met
        420                 425                 430
Glu Asn Gly Trp Ser Pro Thr Pro Arg Cys Ile Arg Val Lys Thr Cys
        435                 440                 445
Ser Lys Ser Ser Ile Asp Ile Glu Asn Gly Phe Ile Ser Glu Ser Gln
    450                 455                 460
Tyr Thr Tyr Ala Leu Lys Glu Lys Ala Lys Tyr Gln Cys Lys Leu Gly
465                 470                 475                 480
Tyr Val Thr Ala Asp Gly Glu Thr Ser Gly Ser Ile Thr Cys Gly Lys
                485                 490                 495
Asp Gly Trp Ser Ala Gln Pro Thr Cys Ile Lys Ser Cys Asp Ile Pro
            500                 505                 510
Val Phe Met Asn Ala Arg Thr Lys Asn Asp Phe Thr Trp Phe Lys Leu
        515                 520                 525
Asn Asp Thr Leu Asp Tyr Glu Cys His Asp Gly Tyr Glu Ser Asn Thr
    530                 535                 540
Gly Ser Thr Thr Gly Ser Ile Val Cys Gly Tyr Asn Gly Trp Ser Asp
545                 550                 555                 560
Leu Pro Ile Cys Tyr Glu Arg Glu Cys Glu Leu Pro Lys Ile Asp Val
                565                 570                 575
His Leu Val Pro Asp Arg Lys Lys Asp Gln Tyr Lys Val Gly Glu Val
            580                 585                 590
Leu Lys Phe Ser Cys Lys Pro Gly Phe Phe Ile Val Gly Pro Asn Ser
        595                 600                 605
Val Gln Cys Tyr His Phe Gly Leu Ser Pro Asp Leu Pro Ile Cys Lys
    610                 615                 620
Glu Gln Val Gln Ser Cys Gly Pro Pro Glu Leu Leu Asn Gly Asn
625                 630                 635                 640
Val Lys Glu Lys Thr Lys Glu Glu Tyr Gly His Ser Glu Val Val Glu
                645                 650                 655
Tyr Tyr Cys Asn Pro Arg Phe Leu Met Lys Gly Pro Asn Lys Ile Gln
            660                 665                 670
Cys Val Asp Gly Glu Trp Thr Thr Leu Pro Val Cys Ile Val Glu Glu
        675                 680                 685
Ser Thr Cys Gly Asp Ile Pro Glu Leu Glu His Gly Trp Ala Gln Leu
    690                 695                 700
Ser Ser Pro Pro Tyr Tyr Tyr Gly Asp Ser Val Glu Phe Asn Cys Ser
705                 710                 715                 720
Glu Ser Phe Thr Met Ile Gly His Arg Ser Ile Thr Cys Ile His Gly
                725                 730                 735
Val Trp Thr Gln Leu Pro Gln Cys Val Ala Ile Asp Lys Leu Lys Lys
            740                 745                 750
Cys Lys Ser Ser Asn Leu Ile Ile Leu Glu Glu His Leu Lys Asn Lys
        755                 760                 765
Lys Glu Phe Asp His Asn Ser Asn Ile Arg Tyr Arg Cys Arg Gly Lys
    770                 775                 780
Glu Gly Trp Ile His Thr Val Cys Ile Asn Gly Arg Trp Asp Pro Glu
785                 790                 795                 800
Val Asn Cys Ser Met Ala Gln Ile Gln Leu Cys Pro Pro Pro Gln
                805                 810                 815
Ile Pro Asn Ser His Asn Met Thr Thr Thr Leu Asn Tyr Arg Asp Gly
```

```
                820             825             830
Glu Lys Val Ser Val Leu Cys Gln Glu Asn Tyr Leu Ile Gln Glu Gly
            835             840             845
Glu Glu Ile Thr Cys Lys Asp Gly Arg Trp Gln Ser Ile Pro Leu Cys
    850             855             860
Val Glu Lys Ile Pro Cys Ser Gln Pro Pro Gln Ile Glu His Gly Thr
865             870             875             880
Ile Asn Ser Ser Arg Ser Ser Gln Glu Ser Tyr Ala His Gly Thr Lys
                885             890             895
Leu Ser Tyr Thr Cys Glu Gly Gly Phe Arg Ile Ser Glu Glu Asn Glu
            900             905             910
Thr Thr Cys Tyr Met Gly Lys Trp Ser Ser Pro Pro Gln Cys Glu Gly
            915             920             925
Leu Pro Cys Lys Ser Pro Pro Glu Ile Ser His Gly Val Val Ala His
    930             935             940
Met Ser Asp Ser Tyr Gln Tyr Gly Glu Glu Val Thr Tyr Lys Cys Phe
945             950             955             960
Glu Gly Phe Gly Ile Asp Gly Pro Ala Ile Ala Lys Cys Leu Gly Glu
            965             970             975
Lys Trp Ser His Pro Pro Ser Cys Ile Lys Thr Asp Cys Leu Ser Leu
            980             985             990
Pro Ser Phe Glu Asn Ala Ile Pro Met Gly Glu Lys Lys Asp Val Tyr
        995             1000            1005
Lys Ala Gly Glu Gln Val Thr Tyr Thr Cys Ala Thr Tyr Tyr Lys
    1010            1015            1020
Met Asp Gly Ala Ser Asn Val Thr Cys Ile Asn Ser Arg Trp Thr
    1025            1030            1035
Gly Arg Pro Thr Cys Arg Asp Thr Ser Cys Val Asn Pro Pro Thr
    1040            1045            1050
Val Gln Asn Ala Tyr Ile Val Ser Arg Gln Met Ser Lys Tyr Pro
    1055            1060            1065
Ser Gly Glu Arg Val Arg Tyr Gln Cys Arg Ser Pro Tyr Glu Met
    1070            1075            1080
Phe Gly Asp Glu Glu Val Met Cys Leu Asn Gly Asn Trp Thr Glu
    1085            1090            1095
Pro Pro Gln Cys Lys Asp Ser Thr Gly Lys Cys Gly Pro Pro Pro
    1100            1105            1110
Pro Ile Asp Asn Gly Asp Ile Thr Ser Phe Pro Leu Ser Val Tyr
    1115            1120            1125
Ala Pro Ala Ser Ser Val Glu Tyr Gln Cys Gln Asn Leu Tyr Gln
    1130            1135            1140
Leu Glu Gly Asn Lys Arg Ile Thr Cys Arg Asn Gly Gln Trp Ser
    1145            1150            1155
Glu Pro Pro Lys Cys Leu His Pro Cys Val Ile Ser Arg Glu Ile
    1160            1165            1170
Met Glu Asn Tyr Asn Ile Ala Leu Arg Trp Thr Ala Lys Gln Lys
    1175            1180            1185
Leu Tyr Ser Arg Thr Gly Glu Ser Val Glu Phe Val Cys Lys Arg
    1190            1195            1200
Gly Tyr Arg Leu Ser Ser Arg Ser His Thr Leu Arg Thr Thr Cys
    1205            1210            1215
Trp Asp Gly Lys Leu Glu Tyr Pro Thr Cys Ala Lys Arg
    1220            1225            1230
```

-continued

```
<210> SEQ ID NO 53
<211> LENGTH: 1234
<212> TYPE: PRT
<213> ORGANISM: Mus musculus

<400> SEQUENCE: 53

Met Arg Leu Ser Ala Arg Ile Ile Trp Leu Ile Leu Trp Thr Val Cys
1               5                   10                  15

Ala Ala Glu Asp Cys Lys Gly Pro Pro Arg Glu Asn Ser Glu Ile
            20                  25                  30

Leu Ser Gly Ser Trp Ser Glu Gln Leu Tyr Pro Glu Gly Thr Gln Ala
        35                  40                  45

Thr Tyr Lys Cys Arg Pro Gly Tyr Arg Thr Leu Gly Thr Ile Val Lys
    50                  55                  60

Val Cys Lys Asn Gly Lys Trp Val Ala Ser Asn Pro Ser Arg Ile Cys
65                  70                  75                  80

Arg Lys Lys Pro Cys Gly His Pro Gly Asp Thr Pro Phe Gly Ser Phe
                85                  90                  95

Arg Leu Ala Val Gly Ser Gln Phe Glu Phe Gly Ala Lys Val Val Tyr
            100                 105                 110

Thr Cys Asp Asp Gly Tyr Gln Leu Leu Gly Glu Ile Asp Tyr Arg Glu
        115                 120                 125

Cys Gly Ala Asp Gly Trp Ile Asn Asp Ile Pro Leu Cys Glu Val Val
    130                 135                 140

Lys Cys Leu Pro Val Thr Glu Leu Glu Asn Gly Arg Ile Val Ser Gly
145                 150                 155                 160

Ala Ala Glu Thr Asp Gln Glu Tyr Tyr Phe Gly Gln Val Val Arg Phe
                165                 170                 175

Glu Cys Asn Ser Gly Phe Lys Ile Glu Gly His Lys Glu Ile His Cys
            180                 185                 190

Ser Glu Asn Gly Leu Trp Ser Asn Glu Lys Pro Arg Cys Val Glu Ile
        195                 200                 205

Leu Cys Thr Pro Pro Arg Val Glu Asn Gly Asp Gly Ile Asn Val Lys
    210                 215                 220

Pro Val Tyr Lys Glu Asn Glu Arg Tyr His Tyr Lys Cys Lys His Gly
225                 230                 235                 240

Tyr Val Pro Lys Glu Arg Gly Asp Ala Val Cys Thr Gly Ser Gly Trp
                245                 250                 255

Ser Ser Gln Pro Phe Cys Glu Glu Lys Arg Cys Ser Pro Pro Tyr Ile
            260                 265                 270

Leu Asn Gly Ile Tyr Thr Pro His Arg Ile Ile His Arg Ser Asp Asp
        275                 280                 285

Glu Ile Arg Tyr Glu Cys Asn Tyr Gly Phe Tyr Pro Val Thr Gly Ser
    290                 295                 300

Thr Val Ser Lys Cys Thr Pro Thr Gly Trp Ile Pro Val Pro Arg Cys
305                 310                 315                 320

Thr Leu Lys Pro Cys Glu Phe Pro Gln Phe Lys Tyr Gly Arg Leu Tyr
                325                 330                 335

Tyr Glu Glu Ser Leu Arg Pro Asn Phe Pro Val Ser Ile Gly Asn Lys
            340                 345                 350

Tyr Ser Tyr Lys Cys Asp Asn Gly Phe Ser Pro Pro Ser Gly Tyr Ser
        355                 360                 365

Trp Asp Tyr Leu Arg Cys Thr Ala Gln Gly Trp Glu Pro Glu Val Pro
```

```
                370                 375                 380
Cys Val Arg Lys Cys Val Phe His Tyr Val Glu Asn Gly Asp Ser Ala
385                 390                 395                 400

Tyr Trp Glu Lys Val Tyr Val Gln Gly Gln Ser Leu Lys Val Gln Cys
                405                 410                 415

Tyr Asn Gly Tyr Ser Leu Gln Asn Gly Gln Asp Thr Met Thr Cys Thr
                420                 425                 430

Glu Asn Gly Trp Ser Pro Pro Lys Cys Ile Arg Ile Lys Thr Cys
                435                 440                 445

Ser Ala Ser Asp Ile His Ile Asp Asn Gly Phe Leu Ser Glu Ser Ser
450                 455                 460

Ser Ile Tyr Ala Leu Asn Arg Glu Thr Ser Tyr Arg Cys Lys Gln Gly
465                 470                 475                 480

Tyr Val Thr Asn Thr Gly Glu Ile Ser Gly Ser Ile Thr Cys Leu Gln
                485                 490                 495

Asn Gly Trp Ser Pro Gln Pro Ser Cys Ile Lys Ser Cys Asp Met Pro
                500                 505                 510

Val Phe Glu Asn Ser Ile Thr Lys Asn Thr Arg Thr Trp Phe Lys Leu
                515                 520                 525

Asn Asp Lys Leu Asp Tyr Glu Cys Leu Val Gly Phe Glu Asn Glu Tyr
530                 535                 540

Lys His Thr Lys Gly Ser Ile Thr Cys Thr Tyr Tyr Gly Trp Ser Asp
545                 550                 555                 560

Thr Pro Ser Cys Tyr Glu Arg Glu Cys Ser Val Pro Thr Leu Asp Arg
                565                 570                 575

Lys Leu Val Val Ser Pro Arg Lys Glu Lys Tyr Arg Val Gly Asp Leu
                580                 585                 590

Leu Glu Phe Ser Cys His Ser Gly His Arg Val Gly Pro Asp Ser Val
                595                 600                 605

Gln Cys Tyr His Phe Gly Trp Ser Pro Gly Phe Pro Thr Cys Lys Gly
610                 615                 620

Gln Val Ala Ser Cys Ala Pro Pro Leu Glu Ile Leu Asn Gly Glu Ile
625                 630                 635                 640

Asn Gly Ala Lys Lys Val Glu Tyr Ser His Gly Glu Val Val Lys Tyr
                645                 650                 655

Asp Cys Lys Pro Arg Phe Leu Leu Lys Gly Pro Asn Lys Ile Gln Cys
                660                 665                 670

Val Asp Gly Asn Trp Thr Thr Leu Pro Val Cys Ile Glu Glu Arg
                675                 680                 685

Thr Cys Gly Asp Ile Pro Glu Leu Glu His Gly Ser Ala Lys Cys Ser
690                 695                 700

Val Pro Pro Tyr His His Gly Asp Ser Val Glu Phe Ile Cys Glu Glu
705                 710                 715                 720

Asn Phe Phe Met Ile Gly His Gly Ser Val Ser Cys Ile Ser Gly Lys
                725                 730                 735

Trp Thr Gln Leu Pro Lys Cys Val Ala Thr Asp Gln Leu Glu Lys Cys
                740                 745                 750

Arg Val Leu Lys Ser Thr Gly Ile Glu Ala Ile Lys Pro Lys Leu Thr
                755                 760                 765

Glu Phe Phe His Asn Ser Thr Met Asp Tyr Lys Cys Arg Asp Lys Gln
                770                 775                 780

Glu Tyr Glu Arg Ser Ile Cys Ile Asn Gly Lys Trp Asp Pro Glu Pro
785                 790                 795                 800
```

```
Asn Cys Thr Ser Lys Thr Ser Cys Pro Pro Pro Gln Ile Pro Asn
            805                 810                 815
Thr Gln Val Ile Glu Thr Thr Val Lys Tyr Leu Asp Gly Glu Lys Leu
            820                 825                 830
Ser Val Leu Cys Gln Asp Asn Tyr Leu Thr Gln Asp Ser Glu Met
            835                 840                 845
Val Cys Lys Asp Gly Arg Trp Gln Ser Leu Pro Arg Cys Ile Glu Lys
    850                 855                 860
Ile Pro Cys Ser Gln Pro Pro Thr Ile Glu His Gly Ser Ile Asn Leu
865                 870                 875                 880
Pro Arg Ser Ser Glu Glu Arg Asp Ser Ile Glu Ser Ser His
                885                 890                 895
Glu His Gly Thr Thr Phe Ser Tyr Val Cys Asp Asp Gly Phe Arg Ile
                900                 905                 910
Pro Glu Glu Asn Arg Ile Thr Cys Tyr Met Gly Lys Trp Ser Thr Pro
                915                 920                 925
Pro Arg Cys Val Gly Leu Pro Cys Gly Pro Pro Ser Ile Pro Leu
    930                 935                 940
Gly Thr Val Ser Leu Glu Leu Glu Ser Tyr Gln His Gly Glu Glu Val
945                 950                 955                 960
Thr Tyr His Cys Ser Thr Gly Phe Gly Ile Asp Gly Pro Ala Phe Ile
                965                 970                 975
Ile Cys Glu Gly Gly Lys Trp Ser Pro Pro Lys Cys Ile Lys Thr
                980                 985                 990
Asp Cys Asp Val Leu Pro Thr Val Lys Asn Ala Ile Ile Arg Gly Lys
            995                 1000                1005
Ser Lys Lys Ser Tyr Arg Thr Gly Glu Gln Val Thr Phe Arg Cys
    1010                1015                1020
Gln Ser Pro Tyr Gln Met Asn Gly Ser Asp Thr Val Thr Cys Val
    1025                1030                1035
Asn Ser Arg Trp Ile Gly Gln Pro Val Cys Lys Asp Asn Ser Cys
    1040                1045                1050
Val Asp Pro Pro His Val Pro Asn Ala Thr Ile Val Thr Arg Thr
    1055                1060                1065
Lys Asn Lys Tyr Leu His Gly Asp Arg Val Arg Tyr Glu Cys Asn
    1070                1075                1080
Lys Pro Leu Glu Leu Phe Gly Gln Val Glu Val Met Cys Glu Asn
    1085                1090                1095
Gly Ile Trp Thr Glu Lys Pro Lys Cys Arg Asp Ser Thr Gly Lys
    1100                1105                1110
Cys Gly Pro Pro Pro Ile Asp Asn Gly Asp Ile Thr Ser Leu
    1115                1120                1125
Ser Leu Pro Val Tyr Glu Pro Leu Ser Ser Val Glu Tyr Gln Cys
    1130                1135                1140
Gln Lys Tyr Tyr Leu Leu Lys Gly Lys Lys Thr Ile Thr Cys Thr
    1145                1150                1155
Asn Gly Lys Trp Ser Glu Pro Pro Thr Cys Leu His Ala Cys Val
    1160                1165                1170
Ile Pro Glu Asn Ile Met Glu Ser His Asn Ile Ile Leu Lys Trp
    1175                1180                1185
Arg His Thr Glu Lys Ile Tyr Ser His Ser Gly Glu Asp Ile Glu
    1190                1195                1200
```

```
Phe Gly Cys Lys Tyr Gly Tyr Tyr Lys Ala Arg Asp Ser Pro Pro
    1205                1210                1215

Phe Arg Thr Lys Cys Ile Asn Gly Thr Ile Asn Tyr Pro Thr Cys
    1220                1225                1230

Val

<210> SEQ ID NO 54
<211> LENGTH: 21
<212> TYPE: PRT
<213> ORGANISM: Homo sapiens

<400> SEQUENCE: 54

Met Pro Met Gly Ser Leu Gln Pro Leu Ala Thr Leu Tyr Leu Leu Gly
1               5                   10                  15

Met Leu Val Ala Ser
            20

<210> SEQ ID NO 55
<211> LENGTH: 17
<212> TYPE: PRT
<213> ORGANISM: Homo sapiens

<400> SEQUENCE: 55

Met Gly Ala Ala Gly Leu Leu Gly Val Phe Leu Ala Leu Val Ala Pro
1               5                   10                  15

Gly

<210> SEQ ID NO 56
<211> LENGTH: 20
<212> TYPE: PRT
<213> ORGANISM: Homo sapiens

<400> SEQUENCE: 56

Met Gly Ala Ala Gly Leu Leu Gly Val Phe Leu Ala Leu Val Ala Pro
1               5                   10                  15

Gly Val Leu Gly
            20

<210> SEQ ID NO 57
<211> LENGTH: 927
<212> TYPE: DNA
<213> ORGANISM: Artificial Sequence
<220> FEATURE:
<223> OTHER INFORMATION: chemically synthesized

<400> SEQUENCE: 57
gacacgtgat cagccgccac catgcccatg gggtctctgc aaccgctggc caccttgtac      60
ctgctgggga tgctggtcgc ttccgtgcta gcgcatcatc atcatcatca tgtgaaactg     120
caggagtcag gggctgagct tgtgaagcct ggggcttcag tgaagctgtc ctgcaaggct     180
tctggctaca ccttcaccag ctactggatg cactgggtga agcagaggcc tggacgaggc     240
cttgagtgga ttggaaggat tggtcctaat agtggtggta ctaagtacaa tgagaagttc     300
aagagcaagg ccacactgac tgtagacaaa ccctccagca cagcctacat gcagctcagc     360
agcctgacat ctgaggactc tgcggtctat tattgtgcaa gaagaatggt aaaggggtgc     420
tatggactac tggggccaag ggaccacggt caccgtctcc tcaaagggcg aattccagca     480
cactggcggc cgttactagt ggatccgagc tcggtaccaa gcttggcgtc aggaggcggt     540
ggcggctcgg gtggcggcgg ctcttggata tctgcagaat cgcccttga cattgagctc      600
```

```
acccagtctc caaccaccat ggctgcatct cccggggaga agatcactat cacctgcagt    660
gccagctcaa gtataagttc caattacttg cattggtatc agcagaagcc aggattctcc    720
cctaaactct tgatttatag gacatccaat ctggcttctg gagtcccagc tcgcttcagt    780
ggcagtgggt ctgggacctc ttactctctc acaattggca ccatggaggc tgaagatgtt    840
gccacttact actgccagca gggtagtagt ataccacgta cacgttcgga gggggcacca    900
agctggaaat aatagactag tcgtgcg                                        927
```

<210> SEQ ID NO 58
<211> LENGTH: 954
<212> TYPE: DNA
<213> ORGANISM: Artificial Sequence
<220> FEATURE:
<223> OTHER INFORMATION: chemically synthesized

<400> SEQUENCE: 58

```
gacacgaagc ttgccgccac catgcccatg gggtctctgc aaccgctggc caccttgtac     60
ctgctgggga tgctggtcgc ttccgtgcta gcgcatcatc atcatcatca tgtcaagctg    120
caggagtctg ggactgaact ggtgaagcct ggggcttcag tgaagctgtc ctgcaaggct    180
tctggctaca ccttcaccag ctactggatg cactgggtga agcagaggcc tggacaaggc    240
cttgagtgga ttggaaatat taatcctagc aatggtggta ctaactacaa tgagaagttc    300
aagagcaagg ccacactgac tgtagacaaa tcctccagca cagcctacat gcagctcagc    360
agcctgacat ctgaggactc tgcggtctat tattgtgcaa gagaggcat acggttacga    420 cactttgact actggggcca agggaccacg gtcaccgtct cctcaagggc gaattctgca    480
gatatccatc acactggcgg ccgctcgagc atgcatctag agggcccaat tcgccctata    540
gtgagtcgta tatcaggagg cggtggcggc tcgggtggcg gcggctcttg gatatctgca    600
gaattcgccc ttgacattgt gatgacacag tctcctgctt ccttagctgt atctctgggg    660
cagagggcca ccatctcata cagggccagc aaaagtgtca gtacatctgg ctatagttat    720
atgcactgga accaacagaa accaggacag ccacccagac tcctcatcta tcttgtatcc    780
aacctagaat ctggggtccc tgccaggttc agtggcagtg ggtctgggac agacttcacc    840
ctcaacatcc atcctgtgga ggaggaggat gctgcaacct attactgtca gcacattagg    900
gagcttacac gttcggaggg gggaccaagc tggaaataat agcccgggcg tgcg          954
```

<210> SEQ ID NO 59
<211> LENGTH: 385
<212> TYPE: PRT
<213> ORGANISM: Artificial Sequence
<220> FEATURE:
<223> OTHER INFORMATION: alternative splice product of MASP1

<400> SEQUENCE: 59

```
Met Arg Phe Leu Ser Phe Trp Arg Leu Leu Leu Tyr His Ala Leu Cys
1               5                   10                  15

Leu Ala Leu Pro Glu Val Ser Ala His Thr Val Glu Leu Asn Glu Met
                20                  25                  30

Phe Gly Gln Ile Gln Ser Pro Gly Tyr Pro Asp Ser Tyr Pro Ser Asp
            35                  40                  45

Ser Glu Val Thr Trp Asn Ile Thr Val Pro Glu Gly Phe Arg Ile Lys
        50                  55                  60

Leu Tyr Phe Met His Phe Asn Leu Glu Ser Ser Tyr Leu Cys Glu Tyr
65                  70                  75                  80
```

```
Asp Tyr Val Lys Val Glu Thr Glu Asp Gln Val Leu Ala Thr Phe Cys
                85                  90                  95

Gly Arg Glu Thr Thr Asp Thr Gln Thr Pro Gly Gln Glu Val Val
            100                 105                 110

Leu Ser Pro Gly Thr Phe Met Ser Val Thr Phe Arg Ser Asp Phe Ser
            115                 120                 125

Asn Glu Glu Arg Phe Thr Gly Phe Asp Ala His Tyr Met Ala Val Asp
            130                 135                 140

Val Asp Glu Cys Lys Glu Arg Glu Asp Glu Glu Leu Ser Cys Asp His
145                 150                 155                 160

Tyr Cys His Asn Tyr Ile Gly Gly Tyr Tyr Cys Ser Cys Arg Phe Gly
                165                 170                 175

Tyr Ile Leu His Thr Asp Asn Arg Thr Cys Arg Val Glu Cys Ser Gly
            180                 185                 190

Asn Leu Phe Thr Gln Arg Thr Gly Thr Ile Thr Ser Pro Asp Tyr Pro
            195                 200                 205

Asn Pro Tyr Pro Lys Ser Ser Glu Cys Ser Tyr Thr Ile Asp Leu Glu
            210                 215                 220

Glu Gly Phe Met Val Ser Leu Gln Phe Glu Asp Ile Phe Asp Ile Glu
225                 230                 235                 240

Asp His Pro Glu Val Pro Cys Pro Tyr Asp Tyr Ile Lys Ile Lys Ala
                245                 250                 255

Gly Ser Lys Val Trp Gly Pro Phe Cys Gly Glu Lys Ser Pro Glu Pro
                260                 265                 270

Ile Ser Thr Gln Thr His Ser Val Gln Ile Leu Phe Arg Ser Asp Asn
            275                 280                 285

Ser Gly Glu Asn Arg Gly Trp Arg Leu Ser Tyr Arg Ala Ala Gly Asn
290                 295                 300

Glu Cys Pro Lys Leu Gln Pro Pro Val Tyr Gly Lys Ile Glu Pro Ser
305                 310                 315                 320

Gln Ala Val Tyr Ser Phe Lys Asp Gln Val Leu Val Ser Cys Asp Thr
                325                 330                 335

Gly Tyr Lys Val Leu Lys Asp Asn Glu Val Met Asp Thr Phe Gln Ile
            340                 345                 350

Glu Cys Leu Lys Asp Gly Ala Trp Ser Asn Lys Ile Pro Thr Cys Lys
            355                 360                 365

Lys Ser Glu Ile Glu Leu Glu Lys Glu Leu Glu Ser Glu Pro Val Ala
            370                 375                 380

Glu
385

<210> SEQ ID NO 60
<211> LENGTH: 648
<212> TYPE: PRT
<213> ORGANISM: Artificial Sequence
<220> FEATURE:
<223> OTHER INFORMATION: MAp44-B4scFv

<400> SEQUENCE: 60

Met Arg Phe Leu Ser Phe Trp Arg Leu Leu Leu Tyr His Ala Leu Cys
1               5                   10                  15

Leu Ala Leu Pro Glu Val Ser Ala His Thr Val Glu Leu Asn Glu Met
            20                  25                  30

Phe Gly Gln Ile Gln Ser Pro Gly Tyr Pro Asp Ser Tyr Pro Ser Asp
            35                  40                  45
```

```
Ser Glu Val Thr Trp Asn Ile Thr Val Pro Glu Gly Phe Arg Ile Lys
    50                  55                  60

Leu Tyr Phe Met His Phe Asn Leu Glu Ser Ser Tyr Leu Cys Glu Tyr
65                  70                  75                  80

Asp Tyr Val Lys Val Glu Thr Glu Asp Gln Val Leu Ala Thr Phe Cys
                85                  90                  95

Gly Arg Glu Thr Thr Asp Thr Glu Gln Thr Pro Gly Gln Glu Val Val
                100                 105                 110

Leu Ser Pro Gly Thr Phe Met Ser Val Thr Phe Arg Ser Asp Phe Ser
                115                 120                 125

Asn Glu Glu Arg Phe Thr Gly Phe Asp Ala His Tyr Met Ala Val Asp
130                 135                 140

Val Asp Glu Cys Lys Glu Arg Glu Asp Glu Glu Leu Ser Cys Asp His
145                 150                 155                 160

Tyr Cys His Asn Tyr Ile Gly Gly Tyr Tyr Cys Ser Cys Arg Phe Gly
                165                 170                 175

Tyr Ile Leu His Thr Asp Asn Arg Thr Cys Arg Val Glu Cys Ser Gly
            180                 185                 190

Asn Leu Phe Thr Gln Arg Thr Gly Thr Ile Thr Ser Pro Asp Tyr Pro
            195                 200                 205

Asn Pro Tyr Pro Lys Ser Ser Glu Cys Ser Tyr Thr Ile Asp Leu Glu
210                 215                 220

Glu Gly Phe Met Val Ser Leu Gln Phe Glu Asp Ile Phe Asp Ile Glu
225                 230                 235                 240

Asp His Pro Glu Val Pro Cys Pro Tyr Asp Tyr Ile Lys Ile Lys Ala
                245                 250                 255

Gly Ser Lys Val Trp Gly Pro Phe Cys Gly Glu Lys Ser Pro Glu Pro
            260                 265                 270

Ile Ser Thr Gln Thr His Ser Val Gln Ile Leu Phe Arg Ser Asp Asn
            275                 280                 285

Ser Gly Glu Asn Arg Gly Trp Arg Leu Ser Tyr Arg Ala Ala Gly Asn
            290                 295                 300

Glu Cys Pro Lys Leu Gln Pro Pro Val Tyr Gly Lys Ile Glu Pro Ser
305                 310                 315                 320

Gln Ala Val Tyr Ser Phe Lys Asp Gln Val Leu Val Ser Cys Asp Thr
                325                 330                 335

Gly Tyr Lys Val Leu Lys Asp Asn Glu Val Met Asp Thr Phe Gln Ile
            340                 345                 350

Glu Cys Leu Lys Asp Gly Ala Trp Ser Asn Lys Ile Pro Thr Cys Lys
            355                 360                 365

Lys Ser Glu Ile Glu Leu Glu Lys Glu Leu Glu Ser Glu Pro Val Ala
370                 375                 380

Glu Gly Gly Gly Ser Gly Gly Gly Val Lys Leu Gln Glu Ser
385                 390                 395                 400

Gly Pro Glu Leu Val Lys Pro Gly Ala Ser Val Lys Ile Ser Cys Lys
                405                 410                 415

Ala Ser Gly Tyr Thr Phe Thr Asp Tyr Tyr Met Asn Trp Val Lys Gln
                420                 425                 430

Ser His Gly Lys Ser Leu Glu Trp Ile Gly Asp Ile Asn Pro Asn Asn
            435                 440                 445

Gly Gly Thr Ser Tyr Asn Gln Lys Phe Lys Gly Lys Ala Thr Leu Thr
450                 455                 460

Val Asp Lys Ser Ser Ser Thr Ala Tyr Met Glu Leu Arg Ser Leu Thr
```

```
                465                 470                 475                 480
Ser Glu Asp Ser Ala Val Tyr Tyr Cys Ala Arg Tyr Asp Tyr Ala Trp
                    485                 490                 495
Tyr Phe Asp Val Trp Gly Gln Gly Thr Thr Val Thr Val Ser Ser Gly
                500                 505                 510
Gly Gly Gly Ser Gly Gly Gly Gly Ser Gly Gly Gly Gly Asp Val Leu
            515                 520                 525
Met Thr Gln Thr Pro Leu Ser Leu Pro Val Ser Leu Gly Asp Gln Ala
        530                 535                 540
Ser Ile Ser Cys Arg Ser Ser Gln Ser Ile Val His Ser Asn Gly Asn
545                 550                 555                 560
Thr Tyr Leu Glu Trp Tyr Leu Gln Lys Pro Gly Gln Ser Pro Lys Leu
                565                 570                 575
Leu Ile Tyr Lys Val Ser Asn Arg Phe Ser Gly Val Pro Asp Arg Phe
            580                 585                 590
Ser Gly Ser Gly Ser Gly Thr Asp Phe Thr Leu Lys Ile Ser Arg Val
        595                 600                 605
Glu Ala Glu Asp Leu Gly Val Tyr Tyr Cys Phe Gln Gly Ser His Val
    610                 615                 620
Pro Tyr Thr Phe Gly Gly Gly Thr Lys Leu Glu Ile Lys Arg Ile Glu
625                 630                 635                 640
Gly Arg His His His His His His
                645
```

<210> SEQ ID NO 61
<211> LENGTH: 1812
<212> TYPE: DNA
<213> ORGANISM: Artificial Sequence
<220> FEATURE:
<223> OTHER INFORMATION: B4Crry nucleic acid sequence

<400> SEQUENCE: 61

```
atgtccgtgc ctacccaggt gctcggactc ctgctgctgt ggctcaccga cgccaggtgt    60
gtgaagctgc aggagagcgg acccgagctg gtgaagcctg agcctccgt gaagatcagc    120
tgcaaggctt ccggatacac cttcaccgac tactatatga actgggtgaa gcagagccac    180
ggcaagagcc tggagtggat cggcgacatc aaccctaaca cggcggcac ctcctacaac    240
cagaagttca gggcaaggc tacactgacc gtggacaagt cctccagcac cgcctacatg    300
gagctcagga gcctgacctc cgaggattcc gccgtctatt actgtgcccg gtacgactac    360
gcctggtatt tcgacgtgtg gggccagggc acaaccgtca cagtctccag cggaggagga    420
ggaagcggcg gcggaggatc cggaggcgga ggcgatgtcc tgatgacaca gacacctctg    480
agcctccccg tgagcctggg agaccaagcc tccatctcct gcaggtcctc ccagtccatc    540
gtgcacagca atggcaacac ctacctggag tggtatctgc agaagcctgg ccagtccccc    600
aagctgctga tctacaaggt gtccaaccgg ttcagcggcg tccctgacag gttctccgga    660
tccggaagcg gcacagattt caccctgaag atcagcaggg tcgaggccga ggacctggga    720
gtgtactact gcttccaggg ctcccatgtc ccttacacct tcggcggcgg caccaaactg    780
gagatcaagc ggggcggagg tgggtcgggt ggcggcggat cttgcccagc ccatcacag    840
cttccttctg ccaaacctat aaatctaact gatgaatcca tgtttcccat ggaacatat    900
tgttgtatg aatgtctccc aggatatatc aagaggcagt tctctatcac ctgcaaacaa    960
gactcaacct ggacgagtgc tgaagataag tgtatacgaa acaatgtaa aactccttca    1020
```

```
gatcctgaga atggcttggt acatgtacac acaggcattc agtttggatc ccgtattaat    1080
tatacttgta atcaaggata ccgcctcatt ggttcctcct ctgctgtatg tgtcatcact    1140
gatcaaagtg ttgattggga tactgaggca cctatttgtg agtggattcc ttgtgagata    1200
cccccaggca ttcccaatgg agatttcttc agttcaacca gaagagactt tcattatgga    1260
atggtggtta cctaccgctg caacactgat gcgagaggga aggcgctctt taacctggtg    1320
ggtgagccct ccttatactg taccagcaac gatggtgaaa ttggagtctg gagcggccct    1380
cctcctcagt gcattgaact caacaaatgt actcctcctc ctatgttga aaatgcagtc     1440 atgctgtctg agaacagaag cttgtttttc ttaagggata ttgtggagtt agatgtcac     1500 cctggcttta tcatgaaagg agccagcagt gtgcattgtc agtccctaaa caaatgggag    1560
ccagagttac aagctgctt caagggagtg atatgtcgtc tccctcagga gatgagtgga    1620
ttccagaagg ggttgggaat gaaaaaagaa tattattatg agagaatgt aaccttggaa     1680 tgtgaggatg ggtatactct agaaggcagt tctcaaagcc agtgccagtc tgatggcagc    1740
tggaatcctc ttctggccaa atgtgtatct cgctcaatca tcgagggcag gcatcaccac    1800
catcaccact ga                                                        1812
```

<210> SEQ ID NO 62
<211> LENGTH: 603
<212> TYPE: PRT
<213> ORGANISM: Artificial Sequence
<220> FEATURE:
<223> OTHER INFORMATION: B4Crry amino acid sequence

<400> SEQUENCE: 62

```
Met Ser Val Pro Thr Gln Val Leu Gly Leu Leu Leu Trp Leu Thr
1               5                   10                  15

Asp Ala Arg Cys Val Lys Leu Gln Glu Ser Gly Pro Glu Leu Val Lys
                20                  25                  30

Pro Gly Ala Ser Val Lys Ile Ser Cys Lys Ala Ser Gly Tyr Thr Phe
            35                  40                  45

Thr Asp Tyr Tyr Met Asn Trp Val Lys Gln Ser His Gly Lys Ser Leu
        50                  55                  60

Glu Trp Ile Gly Asp Ile Asn Pro Asn Asn Gly Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Arg Tyr Asp Tyr Ala Trp Tyr Phe Asp Val Trp Gly
        115                 120                 125

Gln Gly Thr Thr Val Thr Val Ser Ser Gly Gly Gly Ser Gly Gly
    130                 135                 140

Gly Gly Ser Gly Gly Gly Gly Asp Val Leu Met Thr Gln Thr Pro Leu
145                 150                 155                 160

Ser Leu Pro Val Ser Leu Gly Asp Gln Ala Ser Ile Ser Cys Arg Ser
                165                 170                 175

Ser Gln Ser Ile Val His Ser Asn Gly Asn Thr Tyr Leu Glu Trp Tyr
            180                 185                 190

Leu Gln Lys Pro Gly Gln Ser Pro Lys Leu Leu Ile Tyr Lys Val Ser
        195                 200                 205

Asn Arg Phe Ser Gly Val Pro Asp Arg Phe Ser Gly Ser Gly Ser Gly
    210                 215                 220
```

Thr Asp Phe Thr Leu Lys Ile Ser Arg Val Glu Ala Glu Asp Leu Gly
225                 230                 235                 240

Val Tyr Tyr Cys Phe Gln Gly Ser His Val Pro Tyr Thr Phe Gly Gly
            245                 250                 255

Gly Thr Lys Leu Glu Ile Lys Arg Gly Gly Gly Ser Gly Gly Gly
        260                 265                 270

Gly Ser Cys Pro Ala Pro Ser Gln Leu Pro Ser Ala Lys Pro Ile Asn
        275                 280                 285

Leu Thr Asp Glu Ser Met Phe Pro Ile Gly Thr Tyr Leu Leu Tyr Glu
        290                 295                 300

Cys Leu Pro Gly Tyr Ile Lys Arg Gln Phe Ser Ile Thr Cys Lys Gln
305                 310                 315                 320

Asp Ser Thr Trp Thr Ser Ala Glu Asp Lys Cys Ile Arg Lys Gln Cys
                325                 330                 335

Lys Thr Pro Ser Asp Pro Glu Asn Gly Leu Val His Val His Thr Gly
                340                 345                 350

Ile Gln Phe Gly Ser Arg Ile Asn Tyr Thr Cys Asn Gln Gly Tyr Arg
            355                 360                 365

Leu Ile Gly Ser Ser Ala Val Cys Val Ile Thr Asp Gln Ser Val
370                 375                 380

Asp Trp Asp Thr Glu Ala Pro Ile Cys Glu Trp Ile Pro Cys Glu Ile
385                 390                 395                 400

Pro Pro Gly Ile Pro Asn Gly Asp Phe Phe Ser Ser Thr Arg Glu Asp
                405                 410                 415

Phe His Tyr Gly Met Val Val Thr Tyr Arg Cys Asn Thr Asp Ala Arg
                420                 425                 430

Gly Lys Ala Leu Phe Asn Leu Val Gly Glu Pro Ser Leu Tyr Cys Thr
            435                 440                 445

Ser Asn Asp Gly Glu Ile Gly Val Trp Ser Gly Pro Pro Gln Cys
450                 455                 460

Ile Glu Leu Asn Lys Cys Thr Pro Pro Tyr Val Glu Asn Ala Val
465                 470                 475                 480

Met Leu Ser Glu Asn Arg Ser Leu Phe Ser Leu Arg Asp Ile Val Glu
                485                 490                 495

Phe Arg Cys His Pro Gly Phe Ile Met Lys Gly Ala Ser Ser Val His
                500                 505                 510

Cys Gln Ser Leu Asn Lys Trp Glu Pro Glu Leu Pro Ser Cys Phe Lys
            515                 520                 525

Gly Val Ile Cys Arg Leu Pro Gln Glu Met Ser Gly Phe Gln Lys Gly
        530                 535                 540

Leu Gly Met Lys Lys Glu Tyr Tyr Gly Glu Asn Val Thr Leu Glu
545                 550                 555                 560

Cys Glu Asp Gly Tyr Thr Leu Glu Gly Ser Gln Ser Gln Cys Gln
                565                 570                 575

Ser Asp Gly Ser Trp Asn Pro Leu Leu Ala Lys Cys Val Ser Arg Ser
            580                 585                 590

Ile Ile Glu Gly Arg His His His His His
            595                 600

<210> SEQ ID NO 63
<211> LENGTH: 1806
<212> TYPE: DNA
<213> ORGANISM: Artificial Sequence
<220> FEATURE:

<223> OTHER INFORMATION: C2Crry nucleic acid sequence

<400> SEQUENCE: 63

| | | | | | |
|---|---|---|---|---|---|
| atgagcgtgc | ctacacaggt | gctcggcctg | ctgctcctct | ggctgacaga | cgcccggtgt | 60 |
| gtgaagctgc | aggagtccgg | aaccgagctg | gtgaaacctg | gcgccagcgt | gaaactgagc | 120 |
| tgcaaagcca | gcggatacac | cttcacctcc | tactggatgc | actgggtgaa | acagaggcct | 180 |
| ggccagggcc | tggaatggat | tggcaacatc | aaccccagca | acggcggcac | caactacaat | 240 |
| gagaagttca | agagcaaggc | caccctgacc | gtggataagt | cctcctccac | cgcctacatg | 300 |
| cagctgtcct | ccctcacctc | cgaggacagc | gccgtctatt | actgtgccag | cggggcatc | 360 |
| aggctgaggc | acttcgacta | ctggggccaa | ggcacaaccg | tcaccgtgag | ctccggagga | 420 |
| ggaggcagcg | gaggcggagg | ctccggcgga | ggcggaagcg | acattcagat | gacccagagc | 480 |
| cccaagttca | tgtccacctc | cgtcggcgac | agggtgagca | tcacctgtaa | ggccagccag | 540 |
| gatgtcggca | cagctgtggc | ctggtaccag | cagaagcccg | gccagtcccc | caagctgctg | 600 |
| atctactggg | cttccacaag | gcataccggc | gtccccgata | ggttcacagg | ctccggctcc | 660 |
| ggcaccgact | tcacactcac | catcagcaac | gtccagtccg | aggacctggc | cgactacttc | 720 |
| tgccagcagt | actccagcta | ccccctcacc | ttcggcgctg | gcaccaagct | ggaactcaag | 780 |
| cggggcggag | gtgggtcggg | tggcggcgga | tcttgcccag | ccccatcaca | gcttccttct | 840 |
| gccaaaccta | taaatctaac | tgatgaatcc | atgtttccca | ttggaacata | tttgttgtat | 900 |
| gaatgtctcc | caggatatat | caagaggcag | ttctctatca | cctgcaaaca | agactcaacc | 960 |
| tggacgagtg | ctgaagataa | gtgtatacga | aaacaatgta | aaactccttc | agatcctgag | 1020 |
| aatggcttgg | tacatgtaca | cacaggcatt | cagtttggat | cccgtattaa | ttatacttgt | 1080 |
| aatcaaggat | accgcctcat | tggttcctcc | tctgctgtat | gtgtcatcac | tgatcaaagt | 1140 |
| gttgattggg | atactgaggc | acctatttgt | gagtggattc | cttgtgagat | accccaggc | 1200 |
| attcccaatg | agatttctt | cagttcaacc | agagaagact | tcattatgg | aatggtggtt | 1260 |
| acctaccgct | gcaacactga | tgcgagaggg | aaggcgctct | taacctggt | gggtgagccc | 1320 |
| tcctatact | gtaccagcaa | cgatggtgaa | attggagtct | ggagcggccc | tcctcctcag | 1380 |
| tgcattgaac | tcaacaaatg | tactcctcct | ccctatgttg | aaaatgcagt | catgctgtct | 1440 |
| gagaacagaa | gcttgttttc | cttaagggat | attgtggagt | ttagatgtca | ccctggcttt | 1500 |
| atcatgaaag | gagccagcag | tgtgcattgt | cagtccctaa | acaaatggga | gccagagtta | 1560 |
| ccaagctgct | tcaagggagt | gatatgtcgt | ctccctcagg | agatgagtgg | attccagaag | 1620 |
| gggttgggaa | tgaaaaaaga | atattattat | ggagagaatg | taaccttgga | atgtgaggat | 1680 |
| gggtatactc | tagaaggcag | ttctcaaagc | cagtgccagt | ctgatggcag | ctggaatcct | 1740 |
| cttctggcca | aatgtgtatc | tcgctcaatc | atcgagggca | ggcatcacca | ccatcaccac | 1800 |
| tgatag | | | | | | 1806 |

<210> SEQ ID NO 64
<211> LENGTH: 600
<212> TYPE: PRT
<213> ORGANISM: Artificial Sequence
<220> FEATURE:
<223> OTHER INFORMATION: C2Crry amino acid sequence

<400> SEQUENCE: 64

| Met | Ser | Val | Pro | Thr | Gln | Val | Leu | Gly | Leu | Leu | Leu | Leu | Trp | Leu | Thr |
|---|---|---|---|---|---|---|---|---|---|---|---|---|---|---|---|
| 1 | | | | 5 | | | | | 10 | | | | | 15 | |

```
Asp Ala Arg Cys Val Lys Leu Gln Glu Ser Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Asn Ile Asn Pro Ser Asn Gly Gly Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Arg Gly Ile Arg Leu Arg His Phe Asp Tyr Trp
            115                 120                 125

Gly Gln Gly Thr Thr Val Thr Val Ser Ser Gly Gly Gly Gly Ser Gly
        130                 135                 140

Gly Gly Gly Ser Gly Gly Gly Ser Asp Ile Gln Met Thr Gln Ser
145                 150                 155                 160

Pro Lys Phe Met Ser Thr Ser Val Gly Asp Arg Val Ser Ile Thr Cys
                165                 170                 175

Lys Ala Ser Gln Asp Val Gly Thr Ala Val Ala Trp Tyr Gln Gln Lys
                180                 185                 190

Pro Gly Gln Ser Pro Lys Leu Leu Ile Tyr Trp Ala Ser Thr Arg His
            195                 200                 205

Thr Gly Val Pro Asp Arg Phe Thr Gly Ser Gly Ser Gly Thr Asp Phe
    210                 215                 220

Thr Leu Thr Ile Ser Asn Val Gln Ser Glu Asp Leu Ala Asp Tyr Phe
225                 230                 235                 240

Cys Gln Gln Tyr Ser Ser Tyr Pro Leu Thr Phe Gly Ala Gly Thr Lys
                245                 250                 255

Leu Glu Leu Lys Arg Gly Gly Gly Gly Ser Gly Gly Gly Gly Ser Cys
            260                 265                 270

Pro Ala Pro Ser Gln Leu Pro Ser Ala Lys Pro Ile Asn Leu Thr Asp
        275                 280                 285

Glu Ser Met Phe Pro Ile Gly Thr Tyr Leu Leu Tyr Glu Cys Leu Pro
290                 295                 300

Gly Tyr Ile Lys Arg Gln Phe Ser Ile Thr Cys Lys Gln Asp Ser Thr
305                 310                 315                 320

Trp Thr Ser Ala Glu Asp Lys Cys Ile Arg Lys Gln Cys Lys Thr Pro
            325                 330                 335

Ser Asp Pro Glu Asn Gly Leu Val His Val His Thr Gly Ile Gln Phe
        340                 345                 350

Gly Ser Arg Ile Asn Tyr Thr Cys Asn Gln Gly Tyr Arg Leu Ile Gly
    355                 360                 365

Ser Ser Ser Ala Val Cys Val Ile Thr Asp Gln Ser Val Asp Trp Asp
        370                 375                 380

Thr Glu Ala Pro Ile Cys Glu Trp Ile Pro Cys Glu Ile Pro Pro Gly
385                 390                 395                 400

Ile Pro Asn Gly Asp Phe Phe Ser Ser Thr Arg Glu Asp Phe His Tyr
                405                 410                 415

Gly Met Val Val Thr Tyr Arg Cys Asn Thr Asp Ala Arg Gly Lys Ala
                420                 425                 430

Leu Phe Asn Leu Val Gly Glu Pro Ser Leu Tyr Cys Thr Ser Asn Asp
```

-continued

|  |  |  | 435 |  |  |  | 440 |  |  |  | 445 |  |  |  |
|---|---|---|---|---|---|---|---|---|---|---|---|---|---|---|
| Gly | Glu | Ile | Gly | Val | Trp | Ser | Gly | Pro | Pro | Pro | Gln | Cys | Ile | Glu | Leu |
|  | 450 |  |  |  |  | 455 |  |  |  |  | 460 |  |  |  |  |
| Asn | Lys | Cys | Thr | Pro | Pro | Tyr | Val | Glu | Asn | Ala | Val | Met | Leu | Ser |
| 465 |  |  |  | 470 |  |  |  | 475 |  |  |  |  | 480 |  |
| Glu | Asn | Arg | Ser | Leu | Phe | Ser | Leu | Arg | Asp | Ile | Val | Glu | Phe | Arg | Cys |
|  |  |  |  | 485 |  |  |  | 490 |  |  |  |  | 495 |  |
| His | Pro | Gly | Phe | Ile | Met | Lys | Gly | Ala | Ser | Ser | Val | His | Cys | Gln | Ser |
|  |  |  | 500 |  |  |  | 505 |  |  |  |  | 510 |  |  |
| Leu | Asn | Lys | Trp | Glu | Pro | Glu | Leu | Pro | Ser | Cys | Phe | Lys | Gly | Val | Ile |
|  |  | 515 |  |  |  | 520 |  |  |  |  | 525 |  |  |  |
| Cys | Arg | Leu | Pro | Gln | Glu | Met | Ser | Gly | Phe | Gln | Lys | Gly | Leu | Gly | Met |
|  | 530 |  |  |  |  | 535 |  |  |  |  | 540 |  |  |  |
| Lys | Lys | Glu | Tyr | Tyr | Tyr | Gly | Glu | Asn | Val | Thr | Leu | Glu | Cys | Glu | Asp |
| 545 |  |  |  | 550 |  |  |  | 555 |  |  |  |  | 560 |  |
| Gly | Tyr | Thr | Leu | Glu | Gly | Ser | Ser | Gln | Ser | Gln | Cys | Gln | Ser | Asp | Gly |
|  |  |  | 565 |  |  |  | 570 |  |  |  |  | 575 |  |  |
| Ser | Trp | Asn | Pro | Leu | Leu | Ala | Lys | Cys | Val | Ser | Arg | Ser | Ile | Ile | Glu |
|  |  | 580 |  |  |  | 585 |  |  |  |  | 590 |  |  |  |
| Gly | Arg | His | His | His | His | His |  |  |  |  |  |  |  |  |  |
|  | 595 |  |  |  |  | 600 |  |  |  |  |  |  |  |  |  |

COMPOSITIONS AND METHODS FOR TREATING CENTRAL NERVOUS SYSTEM INJURY

CROSS-REFERENCE TO RELATED APPLICATIONS

This application claims the benefit of priority under 35 U.S.C. § 119(e) to U.S. Provisional Patent Application No. 62/409,196 filed Oct. 17, 2016, the contents of which are incorporated by reference herein in their entirety.

STATEMENT REGARDING FEDERALLY SPONSORED RESEARCH OR DEVELOPMENT

This invention was made with government support under 1P20GM109040-01 awarded by the National Institute of Health. The government has certain rights in the invention.

BACKGROUND OF THE INVENTION

Currently, ischemic stroke is the fifth leading cause of death in the U.S. and is also a major cause of long-term disability in the U. S and worldwide. Traumatic brain injury and spinal cord injury are also major causes of disability worldwide, especially among children and young adults, and such injuries are also prominent types of combat-related injury.

Following onset of cerebral ischemia, many stroke patients show reperfusion of their infarct either spontaneously or as a secondary effect of thrombolytic therapy. Cerebral reperfusion initiates a cascade of pathophysiological events that cause secondary injury, which can lead to greater tissue damage and more severe functional and cognitive deficit. Clinical observation and experimental studies indicate a central role for complement in the propagation of ischemia reperfusion injury (IRI) in both central nervous system (CNS) and in non-CNS tissue.

Despite efforts to develop effective strategies for treatment of stroke, the field remains hampered by the necessity to initiate treatment immediately after onset.

Thus there is a need in the art for improved compositions and methods for treating stroke. The present invention satisfies this unmet need.

SUMMARY OF THE INVENTION

In one aspect, the present invention provides a composition for treating central nervous system injury comprising: (a) a targeted inhibitor molecule comprising a targeting portion and an inhibitor portion, wherein the molecule inhibits complement signaling; and (b) a thrombolytic agent.

In one embodiment, the targeting portion comprises an antibody or fragment thereof that specifically binds to Annexin IV, a post-translational modification found on Annexin IV and other proteins, or a phospholipid. In one embodiment, the inhibitor portion comprises at least one, or a fragment thereof, selected from the group consisting of FH, DAF, MCP, CD59, Crry, MAp44, and CR1.

In one embodiment, the thrombolytic agent is t-PA.

In one aspect, the present invention provides a method for treating central nervous system injury in a subject comprising: (a) administering to the subject a therapeutically effective amount of a composition comprising a targeted inhibitor molecule comprising a targeting portion and an inhibitor portion, wherein the molecule inhibits complement signaling; and (b) providing rehabilitation therapy to the subject.

In one embodiment, the injury is ischemic stroke. In one embodiment, the injury is traumatic brain injury. In one embodiment, the injury is spinal cord injury.

In one embodiment, the targeting portion comprises an antibody or fragment thereof that specifically binds to Annexin IV, a post-translational modification found on Annexin IV and other proteins, or a phospholipid. In one embodiment, the inhibitor portion comprises at least one selected from the group consisting of FH, DAF, MCP, CD59, Crry, MAp44, and CR1.

In one embodiment, the rehabilitation therapy comprises at least one therapy selected from the group consisting of cognitive and motor therapy.

In one aspect, the present invention provides a method for treating central nervous system injury in a subject comprising: (a) administering to the subject a therapeutically effective amount of a composition comprising a targeted inhibitor molecule comprising a targeting portion and an inhibitor portion, wherein the molecule inhibits complement signaling; and (b) administering to the subject a composition comprising a thrombolytic agent.

In one embodiment, the injury is ischemic stroke. In one embodiment, the injury is traumatic brain injury. In one embodiment, the injury is spinal cord injury.

In one embodiment, the targeting portion comprises an antibody or fragment thereof that specifically binds to Annexin IV, a post-translational modification found on Annexin IV and other proteins, or a phospholipid. In one embodiment, the inhibitor portion comprises at least one selected from the group consisting of FH, DAF, MCP, CD59, Crry, MAp44, and CR1.

In one embodiment, the thrombolytic agent is t-PA.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A through FIG. 1E illustrates results from experiments demonstrating that the combination of B4Crry and t-PA reduces t-PA associated hemorrhage and improves survival when administered 2 hours after stroke. FIG. 1A depicts Kaplan-Meyer survival curves showing comparable acute survival up to 3-days after microemboli administration. Mantel-Cox (log-rank) comparison. N=6/group. FIG. 1B depicts hemoglobin content in the ipsilateral hemisphere 48 hours after MCAO showing a significant reduction in hemoglobin by B4Crry alone or in combination with t-PA but not by t-PA alone. One-way ANOVA with Bonferroni's test for multiple comparisons. N=6/group. *$P<0.05$ and **$P<0.01$ compared to vehicle. $P<0.05 compared to t-PA only. FIG. 1C depicts results from C3a ELISA performed 48 hours after microemboli administration and homogenization of the ipsilateral hemisphere showing significant effect of B4Crry and not t-PA on reducing post-stroke complement C3 cleavage. One-way ANOVA with Bonferroni's test for multiple comparisons. N=6/group. *$P<0.05$ and **$P<0.01$ compared to vehicle. $P<0.05 compared to t-PA only. FIG. 1D depicts neurological deficit of animals 72 hours after microemboli administration showing significant reduction in deficits in all three treatment groups. Kruskal-Wallis test with Dunn's test for multiple comparisons. N=8/group. *P<0.05. ***P<0.001. FIG. 1E depicts infarct volume assessed by TTC staining showing a significant reduction in infarct in all treatment groups at 72 hours after microemboli administration. One-way ANOVA with Bonferroni's test for multiple comparisons. N=6/group. *P<0.05 and **P<0.01 compared to vehicle.

FIG. 2, comprising FIG. 2A through FIG. 2E illustrates results from experiments demonstrating that the combination of B4Crry and t-PA reduces t-PA associated hemorrhage and improves survival when administered 4 hours after stroke. FIG. 2A depicts Kaplan-Meyer survival curves showing reduction in survival with t-PA therapy that is nearly statistically significant. Mantel-Cox (log-rank) comparison. N=6/group. P=0.08. FIG. 2B illustrates hemoglobin content in the ipsilateral hemisphere 48 hours after MCAO showing a significant increase in hemoglobin by t-PA alone that is reversed in animals receiving co-treatment with B4Crry. One-way ANOVA with Bonferroni's test for multiple comparisons. N=6/group. *P<0.05 and **P<0.01 compared to vehicle. $P<0.05 compared to t-PA only. FIG. 2C depicts results from C3a ELISA performed 48 hours after microemboli administration showing comparable levels of C3a in vehicle and t-PA treated animals and a near significant reduction in levels in animals treated with B4Crry. One-way ANOVA with Bonferroni's test for multiple comparisons. N=6/group. P=0.07 B4Crry+t-PA compared to t-PA only. FIG. 2D depicts neurological deficit of animals 72 hours after microemboli administration showing significant reduction in deficits in all three treatment groups. Kruskal-Wallis test with Dunn's test for multiple comparisons. N=8/group. *P<0.05. ***P<0.001. FIG. 2E depicts infarct volume assessed by TTC staining showing a significant reduction in infarct only in animals co-treated with B4Crry and t-PA. One-way ANOVA with Bonferroni's test for multiple comparisons. N=6/group. *P<0.05 compared to vehicle.

FIG. 3, comprising FIG. 3A through FIG. 3E illustrates results from experiments demonstrating that the combination of B4Crry and t-PA reduces t-PA associated hemorrhage and improves survival when administered 6 hours after stroke. FIG. 3A depicts Kaplan-Meyer survival curves showing significant reduction in survival compared to vehicle in animals treated with t-PA but not co-treated with B4Crry. Mantel-Cox (log-rank) comparison. N=6/group. *P<0.05. FIG. 3B depicts Hemoglobin content in the ipsilateral hemisphere 48 hours after MCAO showing a significant increase in hemoglobin by t-PA alone that is reversed in animals receiving co-treatment with B4Crry. One-way ANOVA with Bonferroni's test for multiple comparisons. N=6/group. *P<0.05 and ***P<0.001 compared to vehicle. $P<0.05 compared to t-PA only. FIG. 3C depicts results from a C3a ELISA performed 48 hours after microemboli administration showing comparable levels of C3a in vehicle and t-PA treated animals and a significant reduction in levels in animals treated with B4Crry. One-way ANOVA with Bonferroni's test for multiple comparisons. N=6/group. $P<0.05 compared to t-PA only. FIG. 3D depicts results indicating neurological deficit of animals 72 hours after microemboli administration showing significant reduction in deficits only in animals receiving co-therapy compared to vehicle controls. Kruskal-Wallis test with Dunn's test for multiple comparisons. N=8/group. *P<0.05. FIG. 3E depicts infarct volume assessed by TTC staining showing a significant reduction in infarct in animals co-treated with B4Crry and t-PA compared to vehicle or t-PA only. One-way ANOVA with Bonferroni's test for multiple comparisons. N=6/group. **P<0.01 compared to vehicle. $P<0.05 compared to t-PA only.

FIG. 4, comprising FIG. 4A through FIG. 4H is a set of images depicting results from experiments determining optimal motor and cognitive recovery after embolic stroke in response to B4Crry, t-PA, and rehabilitation. Animals were subjected to microembolic stroke, treated with t-PA or vehicle at 2 hours and assessed over 30 days. FIG. 4E depicts a Kaplan-Meyer survival curve showing that animals treated with B4Crry and t-PA have significantly better 30-day survival compared to vehicle. Mantel-Cox (log-rank) test. N=8-12/group. *P<0.05. FIG. 4F depicts Neurological deficit scores showing that B4Crry, t-PA and more effectively their combination significantly improve recovery of function deficits over 30 days of recovery. Kruskal-Wallis test with Bonferroni's test for multiple comparisons. N=8-12/group. *P<0.05. **P<0.05.

FIG. 5, comprising FIG. 5A is a graph illustrating daily neurological deficit score, showing that unlike B4scFv, B4Crry treatment at either 2 hours or 6 hours after ischemia resulted in a significant acute reduction in deficit compared to vehicle controls which was sustained throughout 15 days of recovery. Repeated measures two-way ANOVA with Bonferroni. N=9 (B4scFv, B4Crry (6 hours)). N=13 (Vehicle, B4Crry (2 hours). ^^^p<0.001 comparing vehicle to B4scFv and B4Crry (2 hours). ***P<0.001 comparing vehicle to B4Crry (2 hours) and B4Crry (6 hours). FIG. 5B through FIG. 5E is a set of images depicting animals treated with B4Crry (2 or 6 hours after ischemia) showing significant reduction in forelimb laterality (corner task, FIG. 5B), significant improvement in skilled handling (pasta task, FIG. 5C), significant improvement in spatial learning (Barnes maze, FIG. 5D) and significant improvement in memory retention (passive avoidance, FIG. 5E) with B4Crry treatment at either 2 or 6 hours after ischemia compared to vehicle throughout 15 days of recovery after MCAO. Two-way ANOVA, Bonferroni. N=8-12. *p<0.05. **p<0.01. FIG. 5F depicts the effect of B4Crry administered at 2 or 6 hours after stroke showing significant reduction in lesion volume calculated through 3D-reconstruction of lesions from Nissl stained brain sections at 15 days after MCAO. ANOVA, Bonferroni. N=9-13. *p<0.05. ****p<0.0001. FIG. 5G through FIG. 5J depicts the protective effects of B4Crry administered 24 hours after MCAO on reducing lesion volume (Nissl stain, FIG. 5G), reducing neurological deficits (FIG. 5H) and forelimb laterality (corner test, FIG. 5I), and improving spatial learning and memory (Barnes maze, FIG. 5J) compared to vehicle. Student's t-test. N=6-12/group. *p<0.05. p<0.01. *p<0.001. FIG. 5K and FIG. 5L depicts the effect of B4Crry (administered 2 hours after MCAO) on neurological deficits (FIG. 5K) and lesion volume (FIG. 5L) in adult female mice. Two-way ANOVA (FIG. 5K), t-test (FIG. 5L). N=7-8/group. *p<0.05. **p<0.01. FIG. 5M depicting the effect of B4Crry (administered 2 hours after MCAO) on survival of aged (10 months old) mice after MCAO. Log-rank (Mantel-Cox) test, N=6/group, *p<0.05.

FIG. 6, comprising FIG. 6A through FIG. 6C depicts the effects of B4Crry on markers of inflammation 15 days after MCAO in mice.

FIG. 7, comprising FIG. 7A demonstrates that C2-Crry increases post-stroke survival. FIG. 7B demonstrates that C2-Crry improves neurological deficit after stroke. FIG. 7C demonstrates that C2-Crry improves post-stroke memory retention in passive avoidance test.

FIG. 8 depicts an exemplary nucleic acid sequence and amino acid sequence for B4Crry.

FIG. 9 depicts an exemplary nucleic acid sequence and amino acid sequence for C2Crry.

DETAILED DESCRIPTION

Figure 4A:
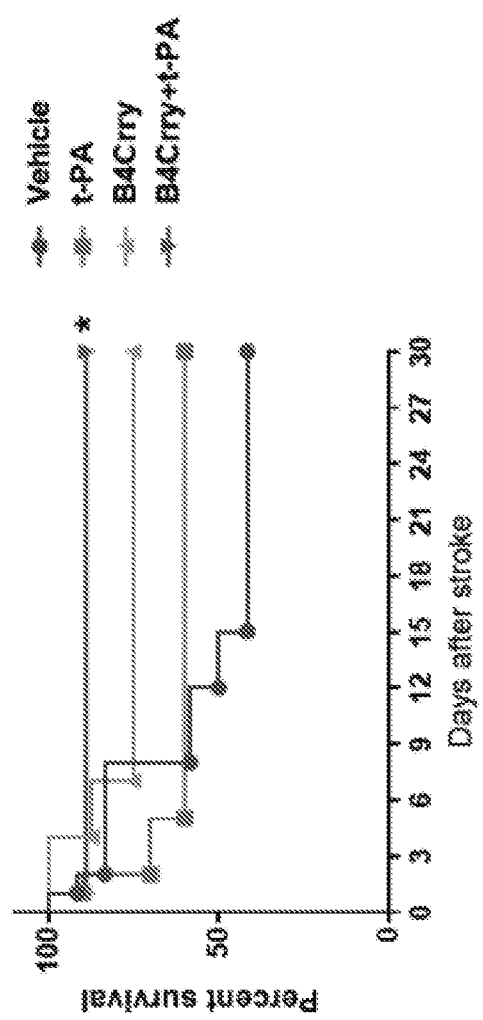
FIG. 4A depicts a Kaplan-Meyer survival curve showing that animals treated with B4Crry and t-PA have significantly better 30-day survival compared to vehicle after microembolic stroke and standard care (No rehabilitation). Mantel-Cox (log-rank) test. N=8-12/group. *P<0.05.

The present invention provides compositions and methods for treating central nervous system injury, including, but not limited to, stroke, traumatic brain injury, and spinal cord injury. For example, the present invention is based upon the discovery that complement inhibition significantly reduces acute mechanisms of degeneration following stroke. For example, it is demonstrated herein that complement inhibition reduces infarct volume and improves functional recovery after stroke. Further, it is demonstrated herein that complement inhibition can be used as an adjuvant therapy in combination with standard stroke therapies to improve patient outcome. Therefore, the present invention provides methods for improving motor recovery, cognitive recovery, and survival after injury to the central nervous system.

In one aspect, the method provides for the use of a complement inhibitor to enhance the response and efficacy of rehabilitation therapy (both cognitive and motor) following central nervous system injury. It is demonstrated herein that a targeted complement inhibitor that inhibits the complement signaling significantly improves rehabilitation-induced motor and cognitive recovery as measured up to 15 days after stroke. The method provides for an effective treatment even when the complement inhibitor is administered as late as about 90 minutes, 2 hours, 4 hours, 6, hours, or 24 hours after injury, which is an improvement over the standard of care where t-PA must be administered with 3 hours of stroke. Thus, the present invention allows for an increase in the available treatment window for central nervous system injury.

In one aspect, the present invention provides for compositions and methods related to the use of targeted complement inhibition as an adjuvant therapy in combination with a thrombolytic agent to improve outcome after central nervous system injury.

A potential problem in the translation of a complement inhibitor strategy to the clinic is the immunosuppressive effect of systemic complement inhibition. Also, complement has important roles in homeostatic and physiological functions such immune complex catabolism, clearance of dead and dying cells, tissue repair, modulation of adaptive immunity, neuroregenerative processes and host defense. Other important concerns regarding the use of systemic complement inhibition relate to efficacy and biodistribution. An approach to alleviate the concerns of systemic inhibition described herein specifically targets complement inhibition to sites of complement activation. In this approach, an antibody or fragment thereof that recognizes Annexin IV, a post-translational modification found on Annexin IV and other proteins, or a phospholipid is linked to a complement inhibitor. It is demonstrated that site-specific targeting of a complement inhibitor obviates the need for systemic inhibition and increases bioavailability and efficacy, without affecting susceptibility to infection, unlike systemic complement inhibition.

In certain instances, the targeting strategy described herein is advantageous for treating and preventing central nervous system injury. First, it will target the proximal event in complement activation, and does not depend on prior complement activation (unlike CR2). Second, the targeting vehicle itself contributes to therapeutic activity by blocking the binding of complement activating pathogenic IgM, which in turn reduces the binding of C1q and MBL, which can impact inflammation, endothelial activation, cell trafficking, and Ag-presentation. Third, it is likely less immunosuppressive since not all sites of infection and C3 deposition will be targeted with complement inhibition. Fourth, it does not limit expression of its own ligand.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "subacute phase" is used herein to describe the period following the incident of a stroke that includes 7 days following an ischemic event or injury.

There term "in combination with" is used herein to that the indicated treatments are administered concurrently or that A "disease" is a state of health of an animal wherein the animal cannot maintain homeostasis, and wherein if the disease is not ameliorated then the animal's health continues to deteriorate.

The terms "effective amount" and "pharmaceutically effective amount" or "therapeutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

The term "fusion protein" used herein refers to two or more peptides, polypeptides, or proteins operably linked to each other.

An "individual" is a vertebrate, preferably a mammal, more preferably a human. Mammals include, but are not limited to, farm animals, sport animals, pets, primates, mice and rats. In some embodiments, the individual is human. In some embodiments, the individual is an individual other than human.

The term "inhibit," as used herein, means to suppress or block an activity or function relative to a control value. Preferably, the activity is suppressed or blocked by 10% compared to a control value, more preferably by 50%, and even more preferably by 95%.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pharmaceutically acceptable" as used herein, refers to agents that, within the scope of sound medical judgment, are suitable for use in contact with tissues of human beings and/or animals without excessive toxicity, irritation, allergic response, or other problem or complication, commensurate with a reasonable benefit/risk ratio.

The terms "subject," "patient," "individual," and the like are used interchangeably herein, and refer to any animal, or cells thereof whether in vitro or in situ, amenable to the methods described herein. In certain non-limiting embodiments, the patient, subject or individual is a human.

The term "sub-therapeutic" as used herein means a treatment at a dose known to be less than what is known to induce a therapeutic effect.

The term "therapeutic" as used herein means a treatment and/or prophylaxis. A therapeutic effect is obtained by suppression, remission, or eradication of a disease state.

The term "therapeutic agent" use herein refers to any agent that has a therapeutic effect and/or elicits a desired biological and/or pharmacological effect, when administered to a subject. In some embodiments, an agent is considered to be a therapeutic agent if its administration to a relevant population is statistically correlated with a desired or beneficial therapeutic outcome in the population, whether or not a particular subject to whom the agent is administered experiences the desired or beneficial therapeutic outcome.

The term "therapeutically effective amount" as used herein, means an amount that is sufficient, when administered to a population suffering from or susceptible to a disease, disorder, and/or condition in accordance with a therapeutic dosing regimen, to treat the disease, disorder, and/or condition (e.g., host versus graft disease). In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. It is specifically understood that particular subjects may, in fact, be "refractory" to a "therapeutically effective amount." To give but one example, a refractory subject may have a low bioavailability such that clinical efficacy is not obtainable. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective agent may be formulated and/or administered in a single dose. In some embodiments, a therapeutically effective agent may be formulated and/or administered in a plurality of doses, for example, as part of a dosing regimen.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

This invention describes a therapeutic composition and method related to the use of targeted complement inhibition as an adjuvant therapy in combination with one or more treatment regimens to improve outcome after central nervous system injury such as ischemic stroke, traumatic brain injury, or spinal cord injury. The present invention relates to compositions and methods for improving the recovery from ischemic stroke, and restoring cerebral function by reducing the risk of stroke-induced damage.

In one embodiment, the method comprises administering to a subject a composition comprising a complement-targeted inhibitor in combination with rehabilitation for use in enhancing recovery following central nervous system injury. In certain embodiments, the complement inhibitor is a composite molecule comprised of a targeting portion and an inhibitor portion wherein the composite molecule targets complement pathways. In certain embodiments, the targeting portion comprises an antibody or a fragment thereof that specifically binds to Annexin IV, a post-translational modification found on Annexin IV and other proteins, or a phospholipid.

In one embodiment, the method comprises administering a composition comprising a complement-targeted inhibitor in combination with rehabilitation therapy. In some instances, the rehabilitation therapy is motor and cognitive therapy. In one embodiment, rehabilitation therapy comprises environmental enrichment.

In one embodiment, the present invention relates to a composition used to treat a subject that has suffered an ischemic stroke, traumatic brain injury, or spinal cord injury. In one embodiment, the composition modulates signaling of complement pathways. In certain instances, the composition of the present invention comprises a composite molecule comprising a targeting portion and an inhibitor portion. In particular, the targeting portion directs the compound of the present invention to complement pathways and the inhibitor portion directs the compound to inhibit complement signaling. In certain embodiments, the targeting portion comprises an antibody or a fragment thereof that specifically binds to Annexin IV, a post-translational modification found on Annexin IV and other proteins, or a phospholipid. In some instances, the inhibiting portion is selected from a list comprising but not limited to Factor H (FH), Crry, DAF, MCP, MAp44, and CR1.

In one embodiment, the composition comprises a composite molecule and a thrombolytic agent. Exemplary thrombolytic agents include, but is not limited to, tissue plasminogen activator (t-PA), urokinase, anistreplase, ancrod, and brinase. It is demonstrated herein that the use of the composite molecule as an adjuvant therapy in combination with t-PA provides improved protection and decreased mortality compared to t-PA alone.

Targeted Complement Inhibitor

In some embodiments, there is provided a molecule (or a composition comprising the molecule such as a pharmaceutical composition), wherein the molecule comprises (a) an antibody or a fragment thereof, wherein the antibody or a fragment thereof specifically binds to Annexin IV, a post-translational modification found on Annexin IV and other proteins, or a phospholipid; and (b) an inhibitor portion.

In some embodiments, the antibody or a fragment thereof specifically binds to a post-translational modification, including, but not limited to, glycosylation, phosphorylation, acetylation, methylation, myristoylation, prenylation, palmitation, amidation, and lipidation, of one or more residues of a protein.

In some embodiments, the molecule comprises an inhibitor portion (such as a complement modulator, for example a complement inhibitor). In some embodiments, the molecule is a fusion protein. In some embodiments, the antibody or fragment thereof (hereinafter also referred to as the "targeting portion" and the inhibitor portion are linked via a linker (such as a peptide linker). In some embodiments, the targeting portion and inhibitor portion are directly linked.

In some embodiments, the targeting portion comprises an antibody or fragment thereof, wherein the antibody or fragment there of comprises: (i) a light chain variable domain comprising a sequence of SEQ ID NO: 1, a sequence of SEQ ID NO:2, or a sequence of SEQ ID NO:3; and/or (ii) heavy chain variable domain comprising a sequence of SEQ ID NO:4, a sequence of SEQ ID NO:5, or a sequence of SEQ ID NO:6.

In some embodiments, the targeting portion comprises an antibody or a fragment thereof, wherein the antibody or a fragment thereof specifically binds to Annexin IV or a post-translational modification found on Annexin IV and other proteins; wherein the antibody or fragment there of comprises: (i) a light chain variable domain comprising a sequence of SEQ ID NO:7, a sequence of SEQ ID NO:8, or a sequence of SEQ ID NO:9; and/or (ii) heavy chain variable domain comprising a sequence of SEQ ID NO: 10, a sequence of SEQ ID NO: 11, or a sequence of SEQ ID NO:

12. In some embodiments, the antibody or fragment thereof competitively inhibits the binding of a pathogenic antibody (such as monoclonal antibody B4) to Annexin IV. In some embodiments, the antibody or fragment thereof binds to the same epitope as a pathogenic antibody (such as a monoclonal antibody B4) to Annexin IV. In some embodiments, the Annexin IV is present on the surface of a cell (and/or in a pathological structure) or in the extracellular matrix in an individual that is in or adjacent to a tissue undergoing (or is at risk of undergoing) tissue injury and/or oxidative damage. In some embodiments, the Annexin IV is produced by a nucleated cell (such as a mammalian cell). In some embodiments, the Annexin IV is recombinant protein.

In some embodiments, the targeting portion comprises an antibody or a fragment thereof, wherein the antibody or a fragment thereof specifically binds to Annexin IV or a post-translational modification found on Annexin IV and other proteins; wherein the antibody or fragment there of comprises: (i) a light chain variable domain comprising a sequence of SEQ ID NO: 1; (ii) a light chain variable domain comprising a sequence of SEQ ID NO:2; and (iii) a light chain variable domain comprising a sequence of SEQ ID NO:3. In some embodiments, the targeting portion comprises an antibody or a fragment thereof, wherein the antibody or a fragment thereof specifically binds to Annexin IV or a post-translational modification found on Annexin IV and other proteins; wherein the antibody or fragment there of comprises: (i) a light chain variable domain comprising a sequence of SEQ ID NO:7; (ii) a light chain variable domain comprising a sequence of SEQ ID NO: 8; and (iii) a light chain variable domain comprising a sequence of SEQ ID NO:9. In some embodiments, the antibody or fragment thereof competitively inhibits the binding of a pathogenic antibody (such as monoclonal antibody B4) to Annexin IV. In some embodiments, the antibody or fragment thereof binds to the same epitope as a pathogenic antibody (such as a monoclonal antibody B4) to Annexin IV. In some embodiments, the Annexin IV is present on the surface of a cell (and/or in a pathological structure) or in the extracellular matrix in an individual that is in or adjacent to a tissue undergoing (or is at risk of undergoing) tissue injury and/or oxidative damage. In some embodiments, the Annexin IV is produced by a nucleated cell (such as a mammalian cell). In some embodiments, the Annexin IV is recombinant protein.

In some embodiments, the targeting portion comprises an antibody or a fragment thereof, wherein the antibody or a fragment thereof specifically binds to Annexin IV or a post-translational modification found on Annexin IV and other proteins; wherein the antibody or fragment there of comprises: (i) heavy chain variable domain comprising a sequence of SEQ ID NO:4; (ii) heavy chain variable domain comprising a sequence of SEQ ID NO:5; and (iii) heavy chain variable domain comprising a sequence of SEQ ID NO:6. In some embodiments, the targeting portion comprises an antibody or a fragment thereof, wherein the antibody or a fragment thereof specifically binds to Annexin IV or a post-translational modification found on Annexin IV and other proteins, wherein the antibody or fragment there of comprises: (i) heavy chain variable domain comprising a sequence of SEQ ID NO: 10; (ii) heavy chain variable domain comprising a sequence of SEQ ID NO: 11; and (iii) heavy chain variable domain comprising a sequence of SEQ ID NO: 12. In some embodiments, the antibody or fragment thereof competitively inhibits the binding of a pathogenic antibody (such as monoclonal antibody B4) to Annexin IV. In some embodiments, the antibody or fragment thereof binds to the same epitope as a pathogenic antibody (such as a monoclonal antibody B4) to Annexin IV. In some embodiments, the Annexin IV is present on the surface of a cell (and/or in a pathological structure) or in the extracellular matrix in an individual that is in or adjacent to a tissue undergoing (or is at risk of undergoing) tissue injury and/or oxidative damage. In some embodiments, the Annexin IV is produced by a nucleated cell (such as a mammalian cell). In some embodiments, the Annexin IV is recombinant protein.

In some embodiments, the targeting portion comprises an antibody or a fragment thereof, wherein the antibody or a fragment thereof specifically binds to Annexin IV or a post-translational modification found on Annexin IV and other proteins; wherein the antibody or fragment there of comprises: (i) a light chain variable domain comprising a sequence of SEQ ID NO: 1; (ii) a light chain variable domain comprising a sequence of SEQ ID NO:2; (iii) a light chain variable domain comprising a sequence of SEQ ID NO:3; (iv) heavy chain variable domain comprising a sequence of SEQ ID NO:4; (v) heavy chain variable domain comprising a sequence of SEQ ID NO:5; and (vi) heavy chain variable domain comprising a sequence of SEQ ID NO:6. In some embodiments, the targeting portion comprises an antibody or a fragment thereof, wherein the antibody or a fragment thereof specifically binds to Annexin IV or a post-translational modification found on Annexin IV and other proteins, wherein the antibody or fragment there of comprises: (i) a light chain variable domain comprising a sequence of SEQ ID NO:7; (ii) a light chain variable domain comprising a sequence of SEQ ID NO: 8; (iii) a light chain variable domain comprising a sequence of SEQ ID NO:9; (iv) heavy chain variable domain comprising a sequence of SEQ ID NO: 10; (v) heavy chain variable domain comprising a sequence of SEQ ID NO: 11; and (vi) heavy chain variable domain comprising a sequence of SEQ ID NO: 12. In some embodiments, the antibody or fragment thereof competitively inhibits the binding of a pathogenic antibody (such as monoclonal antibody B4) to Annexin IV. In some embodiments, the antibody or fragment thereof binds to the same epitope as a pathogenic antibody (such as a monoclonal antibody B4) to Annexin IV. In some embodiments, the Annexin IV is present on the surface of a cell (and/or in a pathological structure) or in the extracellular matrix in an individual that is in or adjacent to a tissue undergoing (or is at risk of undergoing) tissue injury and/or oxidative damage. In some embodiments, the Annexin IV is produced by a nucleated cell (such as a mammalian cell). In some embodiments, the Annexin IV is recombinant protein.

In some embodiments, the targeting portion comprises an antibody or a fragment thereof, wherein the antibody or a fragment thereof specifically binds to Annexin IV or a post-translational modification found on Annexin IV and other proteins, wherein the antibody or fragment there of comprises: (i) a light chain CDR1 of SEQ ID NO: 1; (ii) a light chain CDR2 of SEQ ID NO:2; (iii) a light chain CDR3 of SEQ ID NO:3; (iv) heavy chain CDR1 of SEQ ID NO:4; (v) heavy chain CDR2 of SEQ ID NO:5; and (vi) heavy chain CDR3 of SEQ ID NO:6. In some embodiments the targeting portion comprises an antibody or a fragment thereof, wherein the antibody or a fragment thereof specifically binds to Annexin IV or a post-translational modification found on Annexin IV and other proteins; and (b) a complement modulator or a detectable moiety, wherein the antibody or fragment there of comprises: (i) a light chain CDR1 of SEQ ID NO:7; (ii) a light chain CDR2 of SEQ ID NO: 8; (iii) a light chain CDR3 of SEQ ID NO:9; (iv) heavy chain CDR1 of SEQ ID NO: 10; (v) heavy chain CDR2 of SEQ ID NO: 11; and (vi) heavy chain CDR3 of SEQ ID NO:

12. In some embodiments, the antibody or fragment thereof competitively inhibits the binding of a pathogenic antibody (such as monoclonal antibody B4) to Annexin IV. In some embodiments, the antibody or fragment thereof binds to the same epitope as a pathogenic antibody (such as a monoclonal antibody B4) to Annexin IV. In some embodiments, the Annexin IV is present on the surface of a cell (and/or in a pathological structure) or in the extracellular matrix in an individual that is in or adjacent to a tissue undergoing (or is at risk of undergoing) tissue injury and/or oxidative damage. In some embodiments, the Annexin IV is produced by a nucleated cell (such as a mammalian cell). In some embodiments, the Annexin IV is recombinant protein.

In some embodiments, the targeting portion comprises an antibody or a fragment thereof, wherein the antibody or a fragment thereof specifically binds to Annexin IV or a post-translational modification found on Annexin IV and other proteins, wherein the antibody or fragment there of comprises a light chain variable domain of SEQ ID NO: 13. In some embodiments, the targeting portion comprises an antibody or a fragment thereof, wherein the antibody or a fragment thereof specifically binds to Annexin IV or a post-translational modification found on Annexin IV and other proteins, wherein the antibody or fragment there of comprises a heavy chain variable domain of SEQ ID NO: 15. In some embodiments, the targeting portion comprises an antibody or a fragment thereof, wherein the antibody or a fragment thereof specifically binds to Annexin IV or a post-translational modification found on Annexin IV and other proteins, wherein the antibody or fragment there of comprises a light chain variable domain of SEQ ID NO: 14. In some embodiments, the targeting portion comprises an antibody or a fragment thereof, wherein the antibody or a fragment thereof specifically binds to Annexin IV or a post-translational modification found on Annexin IV and other proteins, wherein the antibody or fragment thereof comprises a heavy chain variable domain of SEQ ID NO: 16. In some embodiments, the antibody or fragment thereof competitively inhibits the binding of a pathogenic monoclonal antibody (such as monoclonal antibody B4) to Annexin IV. In some embodiments, the antibody or fragment thereof competitively inhibits the binding of a pathogenic antibody (such as monoclonal antibody B4) to Annexin IV. In some embodiments, the antibody or fragment thereof binds to the same epitope as a pathogenic antibody (such as a monoclonal antibody B4) to Annexin IV. In some embodiments, the Annexin IV is present on the surface of a cell (and/or in a pathological structure) or in the extracellular matrix in an individual that is in or adjacent to a tissue undergoing (or is at risk of undergoing) tissue injury and/or oxidative damage. In some embodiments, the Annexin IV is produced by a nucleated cell (such as a mammalian cell). In some embodiments, the Annexin IV is recombinant protein In some embodiments, the targeting portion comprises an antibody or a fragment thereof, wherein the antibody or a fragment thereof specifically binds to Annexin IV or a post-translational modification found on Annexin IV and other proteins, wherein the antibody or fragment there of comprises: (i) a light chain variable domain of SEQ ID NO: 13; and (ii) heavy chain variable domain of SEQ ID NO: 15. In some embodiments, the targeting portion comprises an antibody or a fragment thereof, wherein the antibody or a fragment thereof specifically binds to Annexin IV or a post-translational modification found on Annexin IV and other proteins, wherein the antibody or fragment there of comprises: (i) a light chain variable domain of SEQ ID NO: 14; and (ii) heavy chain variable domain of SEQ ID NO: 16.

In some embodiments, the antibody or fragment thereof competitively inhibits the binding of a pathogenic antibody (such as monoclonal antibody B4) to Annexin IV. In some embodiments, the antibody or fragment thereof binds to the same epitope as a pathogenic antibody (such as a monoclonal antibody B4) to Annexin IV. In some embodiments, the Annexin IV is present on the surface of a cell (and/or in a pathological structure) or in the extracellular matrix in an individual that is in or adjacent to a tissue undergoing (or is at risk of undergoing) tissue injury and/or oxidative damage. In some embodiments, the Annexin IV is produced by a nucleated cell (such as a mammalian cell). In some embodiments, the Annexin IV is recombinant protein.

In some embodiments, the targeting portion comprises an antibody or a fragment thereof, wherein the antibody or a fragment thereof specifically binds to Annexin IV or a post-translational modification found on Annexin IV and other proteins, wherein the antibody or fragment is a scFv having the sequence of SEQ ID NO: 17. In some embodiments, the targeting portion comprises an antibody or a fragment thereof, wherein the antibody or a fragment thereof specifically binds to Annexin IV or a post-translational modification found on Annexin IV and other proteins, wherein the antibody or fragment is a scFv having the sequence of SEQ ID NO: 18. In some embodiments, the antibody or fragment thereof competitively inhibits the binding of a pathogenic antibody (such as monoclonal antibody B4) to Annexin IV. In some embodiments, the antibody or fragment thereof binds to the same epitope as a pathogenic antibody (such as a monoclonal antibody B4) to Annexin IV. In some embodiments, the Annexin IV is present on the surface of a cell (and/or in a pathological structure) or in the extracellular matrix in an individual that is in or adjacent to a tissue undergoing (or is at risk of undergoing) tissue injury and/or oxidative damage. In some embodiments, the Annexin IV is produced by a nucleated cell (such as a mammalian cell). In some embodiments, the Annexin IV is recombinant protein.

In some embodiments, the targeting portion comprises an antibody or a fragment thereof, wherein the antibody or a fragment thereof specifically binds to a phospholipid (such as phosphatidylethanolamine (PE), cardiolipin (CL), malondialdehyde (MDA) and/or phosphatidylcholine (PC)), wherein the antibody or fragment thereof comprises: (i) a light chain variable domain comprising a sequence of SEQ ID NO:25, a sequence of SEQ ID NO:26, or a sequence of SEQ ID NO:27; and/or (ii) heavy chain variable domain comprising a sequence of SEQ ID NO:28, a sequence of SEQ ID NO:29, or a sequence of SEQ ID NO:30. In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain variable domain comprising a sequence of SEQ ID NO:31, a sequence of SEQ ID NO:32, or a sequence of SEQ ID NO:33; and/or (ii) heavy chain variable domain comprising a sequence of SEQ ID NO:28, a sequence of SEQ ID NO:29, or a sequence of SEQ ID NO:30. In some embodiments, the antibody or fragment thereof competitively inhibits the binding of a pathogenic antibody (such as monoclonal antibody C2) to phospholipid. In some embodiments, the antibody or antibody fragment thereof binds to the same epitope as a pathogenic antibody (such as monoclonal antibody C2) to phospholipid. In some embodiments, the phospholipid is present on the surface of a cell, a basement membrane, or in a pathological structure in an individual that is in or adjacent to a tissue undergoing (or is at risk of undergoing) tissue injury and/or oxidative damage. In some embodiments, the phospholipid is selected from the group consisting of phosphatidylethanolamine (PE), cardiolipin (CL), and phosphatidylcholine (PC). In some embodiments, the phospholipid is malondialdehyde (MDA). In some embodiments, the phospholipid is neutral. In some embodiments, the phospholipid is positively charged. In some embodiments, the phospholipid is oxidized.

In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain variable domain comprising a sequence of SEQ ID NO:25; (ii) a light chain variable domain comprising a sequence of SEQ ID NO:26; and (iii) a light chain variable domain comprising a sequence of SEQ ID NO:27. In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain variable domain comprising a sequence of SEQ ID NO:31; (ii) a light chain variable domain comprising a sequence of SEQ ID NO:32; and (iii) a light chain variable domain comprising a sequence of SEQ ID NO:33. In some embodiments, the antibody or fragment thereof competitively inhibits the binding of a pathogenic antibody (such as monoclonal antibody C2) to phospholipid. In some embodiments, the antibody or antibody fragment thereof binds to the same epitope as a pathogenic antibody (such as monoclonal antibody C2) to phospholipid. In some embodiments, the phospholipid is present on the surface of a cell, a basement membrane, or in a pathological structure in an individual that is in or adjacent to a tissue undergoing (or is at risk of undergoing) tissue injury and/or oxidative damage. In some embodiments, the phospholipid is selected from the group consisting of phosphatidylethanolamine (PE), cardiolipin (CL), and phosphatidylcholine (PC). In some embodiments, the phospholipid is malondialdehyde (MDA). In some embodiments, the phospholipid is neutral. In some embodiments, the phospholipid is positively charged. In some embodiments, the phospholipid is oxidized.

In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) heavy chain variable domain comprising a sequence of SEQ ID NO:28; (ii) heavy chain variable domain comprising a sequence of SEQ ID NO:29; and (iii) heavy chain variable domain comprising a sequence of SEQ ID NO:30. In some embodiments, the antibody or fragment thereof competitively inhibits the binding of a pathogenic antibody (such as monoclonal antibody C2) to antiphospholipid. In some embodiments, the antibody or antibody fragment thereof binds to the same epitope as a pathogenic antibody (such as monoclonal antibody C2) to phospholipid. In some embodiments, the phospholipid is present on the surface of a cell, a basement membrane, or in a pathological structure in an individual that is in or adjacent to a tissue undergoing (or is at risk of undergoing) tissue injury and/or oxidative damage. In some embodiments, the phospholipid is selected from the group consisting of phosphatidylethanolamine (PE), cardiolipin (CL), and phosphatidylcholine (PC). In some embodiments, the phospholipid is malondialdehyde (MDA). In some embodiments, the phospholipid is neutral. In some embodiments, the phospholipid is positively charged. In some embodiments, the phospholipid is oxidized.

In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain variable domain comprising a sequence of SEQ ID NO:25; (ii) a light chain variable domain comprising a sequence of SEQ ID NO:26; (iii) a light chain variable domain comprising a sequence of SEQ ID NO:27; (iv) heavy chain variable domain comprising a sequence of SEQ ID NO:28; (v) heavy chain variable domain comprising a sequence of SEQ ID NO:29; and (vi) heavy chain variable domain comprising a sequence of SEQ ID NO:30. In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain variable domain comprising a sequence of SEQ ID NO:31; (ii) a light chain variable domain comprising a sequence of SEQ ID NO:32; (iii) a light chain variable domain comprising a sequence of SEQ ID NO:33; (iv) heavy chain variable domain comprising a sequence of SEQ ID NO:28; (v) heavy chain variable domain comprising a sequence of SEQ ID NO:29; and (vi) heavy chain variable domain comprising a sequence of SEQ ID NO:30. In some embodiments, the antibody or fragment thereof competitively inhibits the binding of a pathogenic antibody (such as monoclonal antibody C2) to phospholipid. In some embodiments, the antibody or antibody fragment thereof binds to the same epitope as a pathogenic antibody (such as monoclonal antibody C2) to phospholipid. In some embodiments, the phospholipid is present on the surface of a cell, a basement membrane, or in a pathological structure in an individual that is in or adjacent to a tissue undergoing (or is at risk of undergoing) tissue injury and/or oxidative damage. In some embodiments, the phospholipid is selected from the group consisting of phosphatidylethanolamine (PE), cardiolipin (CL), and phosphatidylcholine (PC). In some embodiments, the phospholipid is malondialdehyde (MDA). In some embodiments, the phospholipid is neutral. In some embodiments, the phospholipid is positively charged. In some embodiments, the phospholipid is oxidized.

In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain CDR1 of SEQ ID NO:25; (ii) a light chain CDR2 of SEQ ID NO:26; (iii) a light chain CDR3 of SEQ ID NO:27; (iv) heavy chain CDR1 of SEQ ID NO:28; (v) heavy chain CDR2 of SEQ ID NO:29; and (vi) heavy chain CDR3 of SEQ ID NO:30. In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain CDR1 of SEQ ID NO:31; (ii) a light chain CDR2 of SEQ ID NO:32; (iii) a light chain CDR3 of SEQ ID NO:33; (iv) heavy chain CDR1 of SEQ ID NO:28; (v) heavy chain CDR2 of SEQ ID NO:29; and (vi) heavy chain CDR3 of SEQ ID NO:30. In some embodiments, the antibody or fragment thereof competitively inhibits the binding of a pathogenic antibody (such as monoclonal antibody C2) to phospholipid. In some embodiments, the antibody or antibody fragment thereof binds to the same epitope as a pathogenic antibody (such as monoclonal antibody C2) to phospholipid. In some embodiments, the phospholipid is present on the surface of a cell, a basement membrane, or in a pathological structure in an individual that is in or adjacent to a tissue undergoing (or is at risk of undergoing) tissue injury and/or oxidative damage. In some embodiments, the phospholipid is selected from the group consisting of phosphatidylethanolamine (PE), cardiolipin (CL), and phosphatidylcholine (PC). In some embodiments, the phospholipid is malondialdehyde (MDA). In some embodiments, the phospholipid is neutral. In some embodiments, the phospholipid is positively charged. In some embodiments, the phospholipid is oxidized.

In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises a light chain variable domain of SEQ ID NO:34. In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises a heavy chain variable domain of SEQ ID NO:36. In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises a light chain variable domain of SEQ ID NO:35. In some embodiments, the antibody or fragment thereof competitively inhibits the binding of a pathogenic antibody (such as monoclonal antibody C2) to phospholipid. In some embodiments, the antibody or antibody fragment thereof binds to the same epitope as a pathogenic antibody (such as monoclonal antibody C2) to phospholipid. In some embodiments, the phospholipid is present on the surface of a cell, a basement membrane, or in a pathological structure in an individual that is in or adjacent to a tissue undergoing (or is at risk of undergoing) tissue injury and/or oxidative damage. In some embodiments, the phospholipid is selected from the group consisting of phosphatidylethanolamine (PE), cardiolipin (CL), and phosphatidylcholine (PC). In some embodiments, the phospholipid is malondialdehyde (MDA). In some embodiments, the phospholipid is neutral. In some embodiments, the phospholipid is positively charged. In some embodiments, the phospholipid is oxidized.

In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain variable domain of SEQ ID NO:34; and (ii) heavy chain variable domain of SEQ ID NO:36. In some embodiments, the targeting portion comprises an antibody or a fragment thereof, wherein the antibody or a fragment thereof specifically binds to a phospholipid (such as PE, CL, MDA, and/or PC), wherein the antibody or fragment thereof comprises: (i) a light chain variable domain of SEQ ID NO:35; and (ii) heavy chain variable domain of SEQ ID NO:36. In some embodiments, the antibody or fragment thereof competitively inhibits the binding of a pathogenic antibody (such as monoclonal antibody C2) to phospholipid. In some embodiments, the antibody or antibody fragment thereof binds to the same epitope as a pathogenic antibody (such as monoclonal antibody C2) to phospholipid. In some embodiments, the phospholipid is present on the surface of a cell, a basement membrane, or in a pathological structure in an individual that is in or adjacent to a tissue undergoing (or is at risk of undergoing) tissue injury and/or oxidative damage. In some embodiments, the phospholipid is selected from the group consisting of phosphatidylethanolamine (PE), cardiolipin (CL), and phosphatidylcholine (PC). In some embodiments, the phospholipid is malondialdehyde (MDA). In some embodiments, the phospholipid is neutral. In some embodiments, the phospholipid is positively charged. In some embodiments, the phospholipid is oxidized.

In some embodiments, the targeting portion comprises an antibody or a fragment thereof, wherein the antibody or a fragment thereof specifically binds to a phospholipid (such as PE, CL, MDA, and/or PC); and (b) an active moiety (e.g., a therapeutic moiety or a detectable moiety), wherein the antibody or fragment is a scFv having the sequence of SEQ ID NO:37. In some embodiments, the targeting portion comprises an antibody or a fragment thereof, wherein the antibody or a fragment thereof specifically binds to a phospholipid (such as PE, CL, MDA, and/or PC), wherein the antibody or fragment is a scFv having the sequence of SEQ ID NO:38. In some embodiments, the antibody or fragment thereof competitively inhibits the binding of a pathogenic antibody (such as monoclonal antibody C2) to phospholipid. In some embodiments, the antibody or antibody fragment thereof binds to the same epitope as a pathogenic antibody (such as monoclonal antibody C2) to phospholipid. In some embodiments, the phospholipid is present on the surface of a cell, a basement membrane, or in a pathological structure in an individual that is in or adjacent to a tissue undergoing (or is at risk of undergoing) tissue injury and/or oxidative damage. In some embodiments, the phospholipid is selected from the group consisting of phosphatidylethanolamine (PE), cardiolipin (CL), and phosphatidylcholine (PC). In some embodiments, the phospholipid is malondialdehyde (MDA). In some embodiments, the phospholipid is neutral. In some embodiments, the phospholipid is positively charged. In some embodiments, the phospholipid is oxidized.

In some embodiments, the targeting portion and inhibitor portion are directly bonded, covalently bonded, or, reversibly bonded. The targeting portion is capable of specifically binding to Annexin IV or a phospholipid. The targeting portion is responsible for targeted delivery of the molecule to the sites of, e.g., complement activation. The inhibitor portion is responsible for therapeutic activity, e.g., specifically inhibiting complement activation. The targeting portion and inhibitor portion of the molecule can be linked together by any methods known in the art, as long as the desired functionalities of the two portions are maintained.

The molecule described herein thus generally has the dual functions of binding to an epitope recognized by an antibody described herein and exerting therapeutic activity. A "epitope of monoclonal antibody B4 antibody" refers to any molecule that binds to a naturally occurring B4 or C2 antibody, which include, epitopes that bind to a B4 or C2 antibody with a binding affinity that is about any of 10%, 20%, 30%, 40%, 50%, 60%, 70%, 80%, 90%, or 100% of the epitope that naturally binds a B4 antibody. Binding affinity can be determined by any method known in the art, including for example, surface plasmon resonance, calorimetry titration, ELISA, and flow cytometry.

In some embodiments, a molecule described herein is generally capable of inhibiting complement activation (for example inhibiting activation of the alternative pathway and/or lectin pathway). The molecule may be a more potent complement inhibitor than the naturally occurring antibody as described herein. For example, in some embodiments, the molecule has a complement inhibitory activity that is about any of 1.5, 2, 2.5, 3, 3.5, 4, 5, 6, 7, 8, 9, 10, 12, 14, 16, 18, 20, 25, 30, 40, or more fold of that of a B4 or C2 antibody. In some embodiments, the molecule has an EC50 of less than about any of 100 nM, 90 nM, 80 nM, 70 nM, 60 nM, 50 nM, 40 nM, 30 nM, 20 nM, or 10 nM, inclusive, including any values in between these numbers. In some embodiments, the molecule has an EC50 of about 5 to 60 nM, including for example any of 8 to 50 nM, 8 to 20 nM, 10 to 40 nM, and 20 to 30 nM. In some embodiments, the molecule has complement inhibitory activity that is about any of 50%, 60%, 70%, 80%, 90%, or 100% of that of a B4 or C2 antibody.

Complement inhibition can be evaluated based on any methods known in the art, including for example, in vitro zymosan assays, assays for lysis of erythrocytes, antibody or immune complex activation assays, alternative pathway activation assays, and mannan activation assays.

In some embodiments, the molecule is a fusion protein. "Fusion protein" used herein refers to two or more peptides, polypeptides, or proteins operably linked to each other. In some embodiments, the targeting portion and inhibitor portion are directly fused to each other. In some embodiments, the targeting portion and inhibitor portion are linked by an amino acid linker sequence. Examples of linker sequences are known in the art, and include, for example, (Gly4Ser), (Gly4Ser)2, (Gly4Ser)3, (Gly3Ser)4, (SerGly4), (SerGly4) 2, (SerGly4)3, and (SerGly4)4. Linking sequences can also comprise "natural" linking sequences found between different domains of complement factors. The order of targeting portion and inhibitor portion in the fusion protein can vary. For example, in some embodiments, the C-terminus of the targeting portion is fused (directly or indirectly) to the N-terminus of the inhibitor portion of the targeting construct. In some embodiments, the N-terminus of the targeting portion is fused (directly or indirectly) to the C-terminus of the inhibitor portion of the molecule. In some embodiments, the targeting portion is encoded by a polynucleotide comprising a nucleic acid sequence of any of 19-24, 39-43, 57 and 58. In some embodiments, the targeting portion is encoded by a polynucleotide comprising a nucleic acid sequence that is at least about 50%, 60%, 70%, 80%, 90%, 91%, 92%, 93%, 94%, 95%, 96%, 97%, 98%, or 99% identical to that of any of SEQ ID NOs: 19-24, 39-43, 57 and 58.

In some embodiments, the molecule comprises a targeting portion and an inhibitor portion linked via a chemical cross-linker. Linking of the two portions can occur on reactive groups located on the two moieties. Reactive groups that can be targeted using a crosslinker include primary amines, sulfhydryls, carbonyls, carbohydrates, and carboxylic acids, or active groups that can be added to proteins. Examples of chemical linkers are well known in the art and include, but are not limited to, bismaleimidohexane, maleimidobenzoyl-N-hydroxysuccinimide ester, NHS-Esters-Maleimide Crosslinkers such as SPDP, carbodiimide, glutaraldehyde, MBS, Sulfo-MBS, SMPB, sulfo-SMPB, GMBS, Sulfo-GMBS, EMCS, Sulfo-EMCS, imidoester crosslinkers such as DMA, DMP, DMS, DTBP, EDC and DTME.

In some embodiments, the targeting portion and inhibitor portion are non-covalently linked. For example, the two portions may be brought together by two interacting bridging proteins (such as biotin and streptavidin), each linked to a targeting portion or an inhibitor portion In some embodiments, the targeting portion comprises two or more (same or different) targeting portions described herein. In some embodiments, the molecule comprises two or more (same or different) inhibitor portions described herein. These two or more portions may be tandemly linked (such as fused) to each other. In some embodiments, the molecule comprises a targeting portion and two or more (such as three, four, five, or more) inhibitor portions. In some embodiments, the molecule comprises an inhibitor portion and two or more (such as three, four, five, or more) targeting portions. In some embodiments, the molecule comprises two or more targeting portions and two or more inhibitor portions.

In some embodiments, there is provided isolated targeted molecules. In some embodiments, the targeting molecules form dimers or multimers.

The active portion and the targeting portion in the targeted molecule can be from the same species (such as human or mouse), or from different species.

Annexin IV belongs to a family of proteins that are Ca2+ and phospholipid proteins. The structure of annexins consists of a conserved Ca2+ and membrane binding core of four annexin repeats (eight for annexin IV) and variable N-terminal regions. Annexins are soluble cytosolic proteins, but despite the lack of obvious signal sequences and the apparent inability to enter the classical secretory pathway, annexins have been identified in extracellular fluids or associated with the external cell surface through poorly understood binding sites. Annexin IV is predominantly produced by epithelial cells and is also found at high levels in lung, intestine, pancreas, liver, photoreceptors, and kidney. Rescher et al., J. Cell Sci., (2004), 117:2631-2639, Kulik et al., (2009) J Immunol. 182(9):5363-73, and Zernii et al., Biochemistry (Mosc), (2003), 68(1): 129-60.

In some embodiments, the Annexin IV is present on the surface of a cell (and/or in a pathological structure) or in the extracellular matrix in an individual that is in or adjacent to a tissue undergoing (or is at risk of undergoing) tissue injury. In some embodiments, the Annexin IV is present on the surface of a cell of an individual that is in or adjacent to a tissue undergoing (or is at risk of undergoing) non-ischemic injury. In some embodiments, the Annexin IV is present on the surface of a cell of an individual that is in or adjacent to a tissue undergoing (or is at risk of undergoing) oxidative damage. In some embodiments, the Annexin IV is present on the surface of a cell of an individual that is in or adjacent to a tissue undergoing (or is at risk of undergoing) ischemia-reperfusion injury. In some embodiments, the Annexin IV is produced by a nucleated cell (such as a mammalian cell). In some embodiments, the Annexin IV is recombinant protein.

In some embodiments, the Annexin IV is present on the surface of a cell, a basement membrane, or in a pathological structure in an individual that is in or adjacent to a tissue undergoing (or is at risk of undergoing) tissue injury. In some embodiments, the Annexin IV is present on the surface of a cell, a basement membrane (or in a pathological structure of an individual that is in or adjacent to a tissue undergoing (or is at risk of undergoing) non-ischemic injury. In some embodiments, the Annexin IV is present on the surface of a cell, a basement membrane or in a pathological structure of an individual that is in or adjacent to a tissue undergoing (or is at risk of undergoing) oxidative damage. In some embodiments, the Annexin IV is present on the surface of a cell, a basement membrane (e.g., Bruch's membrane), or in a pathological structure (e.g., drusen) of an individual that is in or adjacent to a tissue undergoing (or is at risk of undergoing) ischemia-reperfusion injury. In some embodiments, the Annexin IV is produced by a nucleated cell (such as a mammalian cell). In some embodiments, the Annexin IV is recombinant protein.

In some embodiments, the epitope on Annexin IV for the antibody or fragment thereof is present on the surface of a cell (and/or in a pathological structure) or in the extracellular matrix in an individual that is in or adjacent to a tissue undergoing (or is at risk of undergoing) tissue injury but not on the surface of a cell that is in or adjacent to a tissue not undergoing (or is not at risk of undergoing) tissue injury. In some embodiments, the epitope on Annexin IV for the antibody or fragment thereof is present on the surface of a cell (and/or in a pathological structure) or in the extracellular matrix in an individual that is in or adjacent to a tissue undergoing (or is at risk of undergoing) non-ischemic injury but not on the surface of a cell that is in or adjacent to a tissue not undergoing (or is not at risk of undergoing) non-ischemic injury. In some embodiments, the epitope on Annexin IV for the antibody or fragment thereof is present on the surface of a cell that is in or adjacent to a tissue undergoing (or is at risk of undergoing) oxidative damage but not on the surface of a cell that is in or adjacent to a tissue not undergoing (or is not at risk of undergoing) oxidative damage. In some embodiments, the epitope on Annexin IV for the antibody or fragment thereof is present on the surface of a cell (and/or in a pathological structure) or in the extracellular matrix in an individual that is in or adjacent to a tissue undergoing (or is at risk of undergoing) ischemia-reperfusion injury but is not present on the surface of a cell that is in or adjacent to a tissue not undergoing (or is not at risk of undergoing) ischemia reperfusion injury.

In some embodiments, the epitope on Annexin IV for the antibody or fragment thereof is present on the surface of a cell, a basement membrane, or in a pathological structure in an individual that is in or adjacent to a tissue undergoing (or is at risk of undergoing) tissue injury but not on the surface of a cell, a basement membrane, or in a pathological structure that is in or adjacent to a tissue not undergoing (or is not at risk of undergoing) tissue injury. In some embodiments, the epitope on Annexin IV for the antibody or fragment thereof is present on the surface of a cell, a basement membrane, or in a pathological structure in an individual that is in or adjacent to a tissue undergoing (or is at risk of undergoing) non-ischemic injury but not on the surface of a cell, a basement membrane, or in a pathological structure that is in or adjacent to a tissue not undergoing (or is not at risk of undergoing) nonischemic injury. In some embodiments, the epitope on Annexin IV for the antibody or fragment thereof is present on the surface of a cell, a basement membrane, or in a pathological structure that is in or adjacent to a tissue undergoing (or is at risk of undergoing) oxidative damage but not on the surface of a cell, a basement membrane, or in a pathological structure that is in or adjacent to a tissue not undergoing (or is not at risk of undergoing) oxidative damage. In some embodiments, the epitope on Annexin IV for the antibody or fragment thereof is present on the surface of a cell, a basement membrane, or in a pathological structure in an individual that is in or adjacent to a tissue undergoing (or is at risk of undergoing) ischemia-reperfusion injury but is not present on the surface of a cell, a basement membrane, or in a pathological structure that is in or adjacent to a tissue not undergoing (or is not at risk of undergoing) ischemia reperfusion injury.

In some embodiments, the antibody or fragment thereof described herein specifically binds to a phospholipid, which include, but is not limited to, phosphatidylethanolamine (PE), cardiolipin (CL), phosphatidylcholine (PC), and malondialdehyde (MDA). PE, CL, and PC are classes of phospholipids found in biological membranes. Phosphatidylcholine is more commonly found in the exoplasmic or outer leaflet of a cell membrane. It is thought to be transported between membranes within the cell by phosphatidylcholine transfer protein (PCTP). The phospholipid is composed of a choline head group and glycerophosphoric acid with a variety of fatty acids, one being a saturated fatty acid and one being an unsaturated fatty acid. PE consists of a combination of glycerol esterified with two fatty acids and phosphoric acid. Whereas the phosphate group is combined with choline in phosphatidylcholine, it is combined with the ethanolamine in PE. The two fatty acids may be the same, or different, and are usually in the 1,2 positions (though they can be in the 1,3 positions). Cardiolipin (IUPAC name "1,3-bis(sn-3'-phosphatidyl)-sn-glycerol") is an important component of the inner mitochondrial membrane, where it constitutes about 20% of the total lipid composition. Cardiolipin (CL) is a kind of diphosphatidylglycerol lipid, in which two phosphatidylglycerols connect with a glycerol backbone in the center to form a dimeric structure. In most animal tissues, cardiolipin contains 18-carbon fatty alkyl chains with 2 unsaturated bonds on each of them. It has been proposed that the (18:2)4 acyl chain configuration is an important structural requirement for the high affinity of CL to inner membrane proteins in mammalian mitochondria.

Malondialdehyde (MDA) is generated from reactive oxygen species (ROS), and as such is often assayed in vivo as a bio-marker of oxidative stress. Reactive oxygen species degrade polyunsaturated lipids, forming malondialdehyde. This compound is a reactive aldehyde and is one of the many reactive electrophile species that cause toxic stress in cells and form covalent protein adducts referred to as advanced lipoxidation end-products (ALE). The production of this aldehyde is also used as a biomarker to measure the level of oxidative stress in an organism.

In some embodiments, the phospholipid (such as PE, CL, MDA, and/or PC) is present on the surface of a cell (or in a pathological structure) in an individual that is in or adjacent to a tissue undergoing (or is at risk of undergoing) tissue injury. In some embodiments, the phospholipid (such as PE, CL, MDA, and/or PC) is present on the surface of a cell (or in a pathological structure) of an individual that is in or adjacent to a tissue undergoing (or is at risk of undergoing) ocular disease. In some embodiments, the phospholipid (such as PE, CL, MDA, and/or PC) is present on the surface of a cell (or in a pathological structure) of an individual that is in or adjacent to a tissue undergoing (or is at risk of undergoing) oxidative damage. In some embodiments, the phospholipid is neutral. In some embodiments, the phospholipid is positively charged. In some embodiments, the phospholipid (such as PE, CL, MDA, and/or PC) is oxidized.

In some embodiments, the phospholipid (such as PE, CL, MDA, and/or PC) is present on the surface of a cell, a basement membrane, or in a pathological structure in an individual that is in or adjacent to an ocular tissue undergoing (or is at risk of undergoing) tissue injury. In some embodiments, the phospholipid (such as PE, CL, MDA, and/or PC) is present on the surface of a cell, a basement membrane, or in a pathological structure of an individual that is in or adjacent to an ocular tissue undergoing (or is at risk of undergoing) ocular disease. In some embodiments, the phospholipid (such as PE, CL, MDA, and/or PC) is present on the surface of a cell, a basement membrane, or in a pathological structure of an individual that is in or adjacent to a tissue undergoing (or is at risk of undergoing) oxidative damage. In some embodiments, the phospholipid is neutral.

In some embodiments, the phospholipid is positively charged. In some embodiments, the phospholipid (such as PE, CL, MDA, and/or PC) is oxidized.

In some embodiments, the epitope of phospholipid (such as PE, CL, MDA, and/or PC) to which the antibody or fragment thereof binds is present on the surface of a cell or in a pathological structure in an individual that is in or adjacent to a tissue undergoing (or is at risk of undergoing) tissue injury but not on the surface of a cell or in a pathological structure that is in or adjacent to a tissue not undergoing (or is not at risk of undergoing) tissue injury. In some embodiments, the epitope on phospholipid (such as PE, CL, MDA, and/or PC) to which the antibody or fragment thereof binds is present on the surface of a cell or in a pathological structure that is in or adjacent to a tissue undergoing (or is at risk of undergoing) oxidative damage but not on the surface of a cell or in a pathological structure that is in or adjacent to a tissue not undergoing (or is not at risk of undergoing) oxidative damage.

In some embodiments, the epitope of phospholipid (such as PE, CL, MDA, and/or PC) to which the antibody or fragment thereof binds is present on the surface of a cell, a basement membrane, or in a pathological structure in an individual that is in or adjacent to a ocular tissue undergoing (or is at risk of undergoing) tissue injury but not on the surface of a cell, a basement membrane, or in a pathological structure that is in or adjacent to a ocular tissue not undergoing (or is not at risk of undergoing) tissue injury. In some embodiments, the epitope on phospholipid (such as PE, CL, MDA, and/or PC) to which the antibody or fragment thereof binds is present on the surface of a cell, a basement membrane, or in a pathological structure that is in or adjacent to a tissue undergoing (or is at risk of undergoing) oxidative damage but not on the surface of a cell, a basement membrane, or in a pathological structure that is in or adjacent to a tissue not undergoing (or is not at risk of undergoing) oxidative damage.

As described herein, a cell (and/or a pathological structure) that is in or adjacent to a particular tissue as described herein includes a cell (and/or a pathological structure) that is part of a tissue or organ, or adjacent to (near, directly next to, in the microenvironment of, bordering, flanking, adjoining) a tissue or organ, in which a certain event (such as non-ischemic injury or oxidative damage) is going to occur, is likely to occur, or is beginning to occur. As described herein, a cell, a basement, or in a pathological structure that is in or adjacent to a particular tissue as described herein includes a cell that is part of a tissue or organ, or adjacent to (near, directly next to, in the microenvironment of, bordering, flanking, adjoining) a tissue or organ, in which a certain event (such as non-ischemic injury or oxidative damage) is going to occur, is likely to occur, or is beginning to occur. In the case of an adjacent cell, the cell is sufficiently within the microenvironment of the specific tissue or organ such that conditions of oxidative damage and/or inflammation affect the adjacent cell, as well as the specific tissue or organ. Such a cell may display signs of stress, including, but not limited to, the display of "stress proteins" (e.g., heat shock proteins and other proteins associated with a cellular stress response, including annexins) or other molecules on the cell surface (phospholipids, carbohydrate moieties), including the display of abnormal levels of proteins, modified proteins, or other molecules on the cell surface. Such a cell may be undergoing apoptosis or showing signs of apoptosis, such signs including morphological changes in the cell, chromatin condensation, changes in cellular signal transduction protein interactions, changes in intracellular calcium levels, externalization of phospholipids, cell detachment, loss of cell surface structures, etc.

As used herein, the term "selectively binds to" refers to the specific binding of one protein to another protein, to a lipid, or to a carbohydrate moiety (e.g., the binding of an antibody, a fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art, including, but not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

According to the present invention, an "epitope" of a given protein or peptide or other molecule is generally defined, with regard to antibodies, as a part of or site on a larger molecule to which an antibody or antigen-binding fragment thereof will bind, and against which an antibody will be produced. The term epitope can be used interchangeably with the term "antigenic determinant", "antibody binding site", or "conserved binding surface" of a given protein or antigen. More specifically, an epitope can be defined by both the amino acid residues involved in antibody binding and also by their conformation in three-dimensional space (e.g., a conformational epitope or the conserved binding surface). An epitope can be included in peptides as small as about 4-6 amino acid residues, or can be included in larger segments of a protein, and need not be comprised of contiguous amino acid residues when referring to a three dimensional structure of an epitope, particularly with regard to an antibody-binding epitope. Antibody-binding epitopes are frequently conformational epitopes rather than a sequential epitope (i.e., linear epitope), or in other words, an epitope defined by amino acid residues arrayed in three dimensions on the surface of a protein or polypeptide to which an antibody binds. As mentioned above, the conformational epitope is not comprised of a contiguous sequence of amino acid residues, but instead, the residues are perhaps widely separated in the primary protein sequence, and are brought together to form a binding surface by the way the protein folds in its native conformation in three dimensions.

Competition assays can be performed using standard techniques in the art (e.g., competitive ELISA or other binding assays). For example, competitive inhibitors can be detected and quantitated by their ability to inhibit the binding of an antigen to a known, labeled antibody (e.g., the rriAb B4) or to sera or another composition that is known to contain antibodies against the particular antigen (e.g., sera known to contain natural antibodies against the antigen).

According to the present invention, antibodies are characterized in that they comprise immunoglobulin domains and as such, they are members of the immunoglobulin superfamily of proteins. Generally speaking, an antibody molecule comprises two types of chains. One type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to an L chain by a disulfide bond. There are only two types of L chains referred to as lambda (λ) and kappa (κ) chains. In contrast, there are five major H chain classes referred to as isotypes. The five classes include immunoglobulin M (IgM or μ), immunoglobulin D (IgD or δ), immunoglobulin G (IgG or λ), immunoglobulin A (IgA or a), and immunoglobulin E (IgE or ε). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 (γï), IgG2 (γ2), IgG3 (γ3) and IgG4 (γ4), and two subclasses of IgA including IgA1 (l) and IgA2 (a2). In humans, IgG subclass 3 and IgM are the most potent complement activators (classical complement system), while IgG subclass 1 and to an even lesser extent, 2, are moderate to low activators of the classical complement system. IgG4 subclass does not activate the complement system (classical or alternative). The only human immunoglobulin isotype known to activate the alternative complement system is IgA. In mice, the IgG subclasses are IgG1, IgG2a, IgG2b and IgG3. Murine IgG1 does not activate complement, while IgG2a, IgG2b and IgG3 are complement activators.

Each H or L chain of an immunoglobulin molecule comprises two regions referred to as L chain variable domains (VL domains) and L chain constant domains (CL domains), and H chain variable domains (VH domains) and H chain constant domains (CH domains). A complete CH domain comprises three sub-domains (CHI, CH2, CH3) and a hinge region. Together, one H chain and one L chain can form an arm of an immunoglobulin molecule having an immunoglobulin variable region. A complete immunoglobulin molecule comprises two associated (e.g., di-sulfide linked) arms. Thus, each arm of a whole immunoglobulin comprises a VH+L region, and a CH+L region. As used herein, the term "variable region" or "V region" refers to a VH+L region (also known as an Fv fragment), a VL region or a VH region. Also as used herein, the term "constant region" or "C region" refers to a CH+L region, a CL region or a CH region.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are more conserved than others and are referred to as framework regions (FR regions). In contrast, certain portions of a V region are highly variable and are designated hypervariable regions. When the VL and VH domains pair in an immunoglobulin molecule, the hypervariable regions from each domain associate and create hypervariable loops that form the antigen binding sites (antigen combining sites). Thus, the hypervariable loops determine the specificity of an immunoglobulin and are termed complementarity-determining regions (CDRs) because their surfaces are complementary to antigens.

Both an L chain and H chain V gene segment contain three regions of substantial amino acid sequence variability. Such regions are referred to as L chain CDR1, CDR2 and CDR3, and H chain CDR1, CDR2 and CDR3, respectively. The length of an L chain CDR1 can vary substantially between different VL regions. For example, the length of CDR1 can vary from about 7 amino acids to about 17 amino acids. In contrast, the lengths of L chain CDR2 and CDR3 typically do not vary between different VL regions. The length of an H chain CDR3 can vary substantially between different VH regions. For example, the length of CDR3 can vary from about 1 amino acid to about 20 amino acids. Each H and L chain CDR region is flanked by FR regions.

Limited digestion of an immunoglobulin with a protease may produce two fragments. An antigen binding fragment is referred to as an Fab, an Fab', or an F(ab')2 fragment. A fragment lacking the ability to bind to antigen is referred to as an Fc fragment. A Fab fragment comprises one arm of an immunoglobulin molecule containing a L chain (VL+CL domains) paired with the VH region and a portion of the CH region (CHI domain). An Fab' fragment corresponds to an Fab fragment with part of the hinge region attached to the CHI domain. An F(ab')2 fragment corresponds to two Fab' fragments that are normally covalently linked to each other through a disulfide bond, typically in the hinge regions.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab')2 fragments), as well as genetically-engineered antibodies or antigen binding fragments thereof, including single chain antibodies (e.g., scFv), humanized antibodies, antibodies that can bind to more than one epitope (e.g., bi-specific antibodies), or antibodies that can bind to one or more different antigens (e.g., bi- or multi-specific antibodies), may also be employed in the invention.

In some embodiments, the targeting portion comprises an antibody. In some embodiments, the targeting moiety is a scFv. In some embodiments, the targeting portion is a scFv comprising a (i) a light chain variable domain of SEQ ID NO: 13; and/or (ii) heavy chain variable domain of SEQ ID NO: 15. In some embodiments, the targeting portion is a scFv comprising (i) a light chain variable domain of SEQ ID NO: 14; and/or (ii) heavy chain variable domain of SEQ ID NO: 16. In some embodiments, the targeting portion is a scFv having the sequence of SEQ ID NO: 17. In some embodiments, the targeting portion is a scFv having the sequence of SEQ ID NO: 18.

In some embodiments, the targeting portion is a scFv comprising a (i) a light chain variable domain of SEQ ID NO:34; and/or (ii) heavy chain variable domain of SEQ ID NO:36. In some embodiments, the targeting portion is a scFv comprising (i) a light chain variable domain of SEQ ID NO:35; and/or (ii) heavy chain variable domain of SEQ ID NO:36. In some embodiments, the targeting portion is a scFv having the sequence of SEQ ID NO:37. In some embodiments, the targeting portion is a scFv having the sequence of SEQ ID NO:38.

In one embodiment, targeted molecules of the present invention include humanized antibodies or a fragment thereof (such as a humanized scFv). A humanized antibody or fragment thereof are molecules having an antigen binding site derived from an immunoglobulin from a non-human species, the remaining immunoglobulin-derived parts of the molecule being derived from a human immunoglobulin. The antigen binding site may comprise either complete variable regions fused onto human constant domains or only the complementarity determining regions (CDRs) grafted onto appropriate human framework regions in the variable domains. A humanized antibody or fragment thereof can be produced, for example, by modeling the antibody variable domains, and producing the antibodies using genetic engineering techniques, such as CDR grafting. A description various techniques for the production of humanized antibodies is found, for example, in Morrison et al. (1984) Proc. Natl. Acad. Sci. USA 81:6851-55; Whittle et al. (1987) Prot. Eng. 1:499-505; Co et al. (1990) J. Immunol. 148: 1149-1154; Co et al. (1992) Proc. Natl. Acad. Sci. USA 88:2869-2873; Carter et al. (1992) Proc. Natl. Acad. Sci. 89:4285-4289; Routledge et al. (1991) Eur. J. Immunol. 21:2717-2725 and PCT Patent Publication Nos. WO 91/09967; WO 91/09968 and WO 92/113831.

In some embodiments, the antibody or fragment thereof does not activate complement activation. Methods of modifying antibodies or fragments thereof by reducing or eliminating their complement activation activities are known in the art (Tan et al. (1990) Proc Natl Acad Sci USA 87, 162-166).

In some embodiments, the targeting portion of the targeted molecules is a homolog of any of the targeting portion amino acid sequences described herein or a biologically active fragment thereof. Homologs of the targeting portion (or biologically active fragments thereof) include proteins which differ from a targeting portion described herein (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition glycosylphosphatidyl inositol). For example, homologue of a targeting portion may have an amino acid sequence that is at least about 70% identical to the amino acid sequence of a targeting portion described herein, for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a targeting portion described herein. Amino acid sequence identity can be determined in various ways, for example, using publicly available computer software such as BLAST, BLAST-2, ALIGN or MEGALIGNTM (DNAST AR) software. One skilled in the art can determine appropriate parameters for measuring alignment, including any algorithms needed to achieve maximal alignment over the full length of the sequences being compared.

The molecules described herein in some embodiments comprise an inhibitor portion comprising a complement modulator, such as a complement inhibitor.

As used herein, the term "complement inhibitor" refers to any compound, composition, or protein that reduces or eliminates complement activity. The reduction in complement activity may be incremental (e.g., a 10%, 20%, 30%, 40%, 50%, 60%, 70%, 80%, or 90% reduction in activity) or complete. For example, in some embodiments, a complement inhibitor can inhibit complement activity by at least 10 (e.g., at least 15, 20, 25, 30, 35, 40, 45, 50, 55, 60, 65, 70, 75, 80, 85, 90, or 95 or greater) % in a standard in vitro red blood cell hemolysis assay or an in vitro CH50eq assay. See, e.g., Kabat and Mayer (eds), "Experimental Immunochemistry, 2nd Edition," 135-240, Springfield, Ill., CC Thomas (1961), pages 135-139, or a conventional variation of that assay such as the chicken erythrocyte hemolysis method as described in, e.g., Hillmen et al. (2004) N Engl J Med 350(6):552.

The CH50eq assay is a method for measuring the total classical complement activity in serum. This test is a lytic assay, which uses antibody-sensitized erythrocytes as the activator of the classical complement pathway and various dilutions of the test serum to determine the amount required to give 50% lysis (CH50). The percent hemolysis can be determined, for example, using a spectrophotometer. The CH50eq assay provides an indirect measure of terminal complement complex (TCC) formation, since the TCC themselves are directly responsible for the hemolysis that is measured.

The assay is well known and commonly practiced by those of skill in the art. Briefly, to activate the classical complement pathway, undiluted serum samples (e.g., human serum samples) are added to microassay wells containing the antibody-sensitized erythrocytes to thereby generate TCC. Next, the activated sera are diluted in microassay wells, which are coated with a capture reagent (e.g., an antibody that binds to one or more components of the TCC). The TCC present in the activated samples bind to the monoclonal antibodies coating the surface of the microassay wells. The wells are washed and, to each well, is added a detection reagent that is detectably labeled and recognizes the bound TCC. The detectable label can be, e.g., a fluorescent label or an enzymatic label. The assay results are expressed in CH50 unit equivalents per milliliter (CH50 U Eq/mL).

Additional methods for detecting and/or measuring complement activity in vitro are set forth and exemplified in the working examples.

The complement inhibitor described herein in some embodiments is a specific inhibitor of the lectin pathway. In some embodiments, the complement inhibitor is a specific inhibitor of the alternative pathway. In some embodiments, the complement inhibitor is a specific inhibitor of the classical pathway.

In some embodiments, the complement inhibitor is a soluble or membrane-bound protein such as, for example, membrane cofactor protein (MCP), decay accelerating factor (DAF/CD55), CD59, mouse complement receptor 1-related gene/protein y (Crry), human complement receptor 1 (CR1) or factor H, or Factor I, or an antibody specific for a component of a complement pathway such as, for example, eculizumab (an anti-CS antibody marketed under the trade name Soliris®), pexelizumab (the antigen-binding fragment of eculizumab), an anti-factor B antibody (such as the monoclonal antibody 1379 produced by ATCC Deposit No. PTA-6230), an anti-properdin antibody, an anti-factor D antibody, an anti-MASP antibody, an anti MB L-antibody, and the like (see below). Alternatively, a complement inhibitor may be a small molecule or a linear or cyclic peptide such as, for example, compstatin, N-acetylaspartylglutamic acid (NAAGA), and the like. In some embodiments, the complement inhibitor is selected from the group consisting of: an anti-C5 antibody, an Eculizumab, an pexelizumab, an anti-C3b antibody, an anti-C6 antibody, an anti-C7 antibody, an anti-factor B antibody, an anti-factor D antibody, and an anti-properdin antibody, a human membrane co factor protein (MCP), a human decay accelerating factor (DAF), a mouse decay accelerating factor (DAF), a human CD59, a mouse CD59, a mouse CD59 isoform B, a mouse Crry, a human CR1, a Factor I, a human factor H, a mouse factor H, and a biologically active fragment of any the preceding.

As used herein, the term "membrane cofactor protein," "MCP," or "CD46" refers to a widely distributed C3b/C4b-binding cell surface glycoprotein which inhibits complement activation on host cells and serves as a cofactor for the factor I-mediated cleavage of C3b and C4b, including homologs thereof. T. J. Oglesby et al., J. Exp. Med. (1992)

175: 1547-1551. MCP belongs to a family known as the regulators of complement activation ("RCA"). Family members share certain structural features, comprising varying numbers of short consensus repeat (SCR) domains, which are typically between 60 and 70 amino acids in length. Beginning at its amino-terminus, MCP comprises four SCRs, a serine/threonine/proline-enriched region, an area of undefined function, a transmembrane hydrophobic domain, a cytoplasmic anchor and a cytoplasmic tail. It is understood that species and strain variations exist for the disclosed peptides, polypeptides, and proteins, and that human MCP or biologically active fragments thereof encompass all species and strain variations.

SEQ ID NO:44 represents the full-length human MCP amino acid sequence (see, e.g., UniProtKB/Swiss-Prot. Accession No. P15529). Amino acids 1-34 correspond to the signal peptide, amino acids 35-343 correspond to the extracellular domain, amino acids 344-366 correspond to the transmembrane domain, and amino acids 367-392 correspond to the cytoplasmic domain. In the extracellular domain, amino acids 35-96 correspond to SCR 1, amino acids 97-159 correspond to SCR 2, amino acids 160-225 correspond to SCR 3, amino acids 226-285 correspond to SCR 4, and amino acids 302-326 correspond to the serine/threonine-rich domain. It is understood that species and strain variations exist for the disclosed peptides, polypeptides, and proteins, and that MCP or biologically active fragments thereof encompass all species and strain variations. As used herein, the term "biologically active" fragment of MCP refers to any soluble fragment lacking both the cytoplasmic domain and the transmembrane domain, including fragments comprising, consisting essentially of or consisting of 1, 2, 3, or 4 SCR domains, with or without the serine/threonine-rich domain, having some or all of the complement inhibitory activity of the full-length human MCP protein. In some embodiments, the complement inhibitor portion comprises full-length human MCP (amino acids 35-392 of SEQ ID NO:44), the extracellular domain of human MCP (amino acids 35-343 of SEQ ID NO:44), or SCRs 1-4 of human MCP (amino acids 35-285 of SEQ ID NO:44).

Decay accelerating factor, also referred to as CD55 (DAF/CD55) (SEQ ID NO:45 and SEQ ID NO:46), is an ~70 kiloDalton (kDa) membrane-bound glycoprotein which inhibits complement activation on host cells. Like several other complement regulatory proteins, DAF comprises several approximately 60 amino acid repeating motifs termed short consensus repeats (SCR).

As used herein, the term "decay accelerating factor," "DAF," or "CD55" refers to a seventy kilodalton ("kDa") membrane glycoprotein comprising four short consensus repeat (SCR) domains followed by a heavily O-glycosylated serine/threonine-rich domain at the C-terminus that elevates the molecule from the membrane surface, followed by a glycosylphosphatidylinositol ("GPI") anchor. DAF protects the cell surface from complement activation by dissociating membrane-bound C3 convertases that are required to cleave complement protein C3 and to amplify the complement cascade. DAF prevents assembly or accelerates decay of both the C3- and C5-convertases of the alternative and classical complement pathways.

SEQ ID NO:45 represents the full-length human DAF amino acid sequence (see, e.g., UniProtKB/Swiss-Prot. Accession No. P08173); SEQ ID NO:46 represents the full-length mouse DAF amino acid sequence (see, e.g., UniProtKB/Swiss-Prot. Accession No. Q61475). In the human DAF sequence, amino acids 1-34 correspond to the signal peptide, amino acids 35-353 appear in the mature protein, and amino acids 354-381 are removed from the polypeptide after translation. Within the mature protein, amino acids 35-96 correspond to SCR 1, amino acids 96-160 correspond to SCR 2, amino acids 161-222 correspond to SCR 3, amino acids 223-285 correspond to SCR 4, and amino acids 287-353 correspond to the O-glycosylated serine/threonine-rich domain. The GPI anchor is attached to human DAF at a serine at position 353. In the mouse DAF sequence, amino acids 1-34 correspond to the signal peptide, amino acids 35-362 appear in the mature protein, and amino acids 363-390 are removed from the polypeptide after translation. Within the mature protein, amino acids 35-96 correspond to SCR 1, amino acids 97-160 correspond to SCR 2, amino acids 161-222 correspond to SCR 3, amino acids 223-286 correspond to SCR 4, and amino acids 288-362 correspond to the O-glycosylated serine/threonine-rich domain. The GPI anchor is attached to mouse DAF at a serine at position 362. It is understood that species and strain variations exist for the disclosed peptides, polypeptides, and proteins, and that DAF or biologically active fragments thereof encompass all species and strain variations. As used herein, the term "biologically active" fragment of DAF refers to any fragment of DAF lacking a GPI anchor and/or the amino acid to which it is attached (i.e., Ser-353), including any fragments of the full-length DAF protein comprising, consisting essentially of or consisting of 1, 2, 3, or 4 SCR domains, with or without the O-glycosylated serine/threonine-rich domain, having some or all the complement inhibitory activity of the full-length DAF protein.

As used herein, the term "CD59" refers to a membrane-bound 128 amino acid glycoprotein that potently inhibits the membrane attack complex (MAC) of complement. CD59 acts by binding to the C8 and/or C9 components of the MAC during assembly, ultimately preventing incorporation of the multiple copies of C9 required for complete formation of the osmolytic pore at the heart of the MAC. CD59 is both N- and O-glycosylated. The N-glycosylation comprises primarily bi- or tri-antennary structures with and without lactosamine and outer arm fucose residues, with variable sialylation present at some sites. Like DAF, CD59 is anchored in the cell membrane by a glycosylphosphatidylinositol ("GPI") anchor, which is attached to an asparagine at amino acid 102. Soluble forms of CD59 (sCD59) have been produced, but they generally have low functional activity in vitro, particularly in the presence of serum, suggesting that unmodified sCD59 has little or no therapeutic efficacy. See, e.g., S. Meri et al., "Structural composition and functional characterization of soluble CD59: heterogeneity of the oligosaccharide and glycophosphoinositol (GPI) anchor revealed by laser-desorption mass spectrometric analysis," Biochem. J. 316: 923-935 (1996).

SEQ ID NO:47 represents the full-length human CD59 amino acid sequence (see, e.g., UniProtKB/Swiss-Prot. Accession No. P13987); SEQ ID NO:48 represents the full-length mouse CD59 sequence, isoform A (see, e.g., UniProtKB/Swiss-Prot. Accession No. O55186); SEQ ID NO:49 represents the full-length mouse CD59 sequence, isoform B (see, e.g., UniProtKB/SwissProt. Accession No. P58019). In the human CD59 sequence, amino acids 1-25 of SEQ ID NO:47 correspond to the leader peptide, amino acids 26-102 of SEQ ID NO:47 correspond to the mature protein, and amino acids 103-128 of SEQ ID NO:47 are removed after translation. The GPI anchor is attached to CD59 at an asparagine at position 102 of SEQ ID NO:47. In isoform A of the mouse CD59 sequence, amino acids 1-23 of SEQ ID NO:48 correspond to the leader peptide, amino acids 24-96 of SEQ ID NO: 48 correspond to the mature protein, and amino acids 97-123 of SEQ ID NO:48 are removed after translation. The GPI anchor is attached to CD59 at a serine at position 96 of SEQ ID NO: 48. In isoform B of the mouse CD59 sequence, amino acids 1-23 of SEQ ID NO: 49 correspond to the leader peptide, amino acids 24-104 of SEQ ID NO: 49 correspond to the mature protein, and amino acids 105-129 of SEQ ID NO:49 are removed after translation. The GPI anchor is attached to CD59 at an asparagine at position 104 of SEQ ID NO:49. It is understood that species and strain variations exist for the disclosed peptides, polypeptides, and proteins, and that CD59 or biologically active fragments thereof encompass all species and strain variations.

As used herein, the term "biologically active" fragment of human CD59 refers to any fragment of human CD59 lacking a GPI anchor and/or the amino acid to which it is attached (i.e., Asn-102), including any fragments of the full-length human CD59 protein having some or all the complement inhibitory activity of the full-length CD59 protein; and the term "biologically active" fragment of mouse CD59 refers to any fragment of mouse CD59 isoform A or isoform B lacking a GPI anchor and/or the amino acid to which it is attached (i.e., Ser-96 of isoform A, or Asp-104 of isoform B), including any fragments of either full-length mouse CD59 protein isoform having some or all the complement inhibitory activity of the full-length CD59 protein.

As used herein, the term "mouse complement receptor 1-related gene/protein y" or "Crry" refers to a membrane-bound mouse glycoprotein that regulates complement activation, including homologs thereof. Crry regulates complement activation by serving as a cofactor for complement factor I, a serine protease which cleaves C3b and C4b deposited on host tissue. Crry also acts as a decay-accelerating factor, preventing the formation of C4b2a and C3bBb, the amplification convertases of the complement cascade.

SEQ ID NO:50 represents the full-length mouse Crry protein amino acid sequence. Amino acids 1-40 correspond to the leader peptide, amino acids 41-483 of SEQ ID NO:50 correspond to the mature protein, comprising amino acids 41-405 of SEQ ID NO:50, corresponding to the extracellular domain, amino acids 406-426 of SEQ ID NO:50, corresponding to the transmembrane domain, and amino acids 427-483 of SEQ ID NO:50, corresponding to the cytoplasmic domain. In the extracellular domain, amino acids 83-143 of SEQ ID NO:50 correspond to SCR 1, amino acids 144-205 of SEQ ID NO:50 correspond to SCR 2, amino acids 206-276 of SEQ ID NO:50 correspond to SCR 3, amino acids 277-338 of SEQ ID NO:50 correspond to SCR 4, and amino acids 339-400 of SEQ ID NO:50 correspond to SCR 5. It is understood that species and strain variations exist for the disclosed peptides, polypeptides, and proteins, and that mouse Crry protein or biologically active fragments thereof encompasses all species and strain variations. As used herein, the term "biologically active" fragment of mouse Crry protein refers to any soluble fragment of mouse Crry lacking the transmembrane domain and the cytoplasmic domain, including fragments comprising, consisting essentially of or consisting of 1, 2, 3, 4, or 5 SCR domains, including any fragments of the full-length mouse Crry protein having some or all the complement inhibitory activity of the full-length Crry protein. In one embodiment, the biologically active fragment of mouse Crry comprises amino acids 85-403 of SEQ ID NO: 50.

As used herein, the term "complement receptor 1," "CR1," or "CD35" refers to a human gene encoding a protein of 2039 amino acids, with a predicted molecular weight of 220 kiloDaltons ("kDa"), including homologs thereof. The gene is expressed principally on erythrocytes, monocytes, neutrophils, and B cells, but is also present on some T lymphocytes, mast cells, and glomerular podocytes. CR1 protein is typically expressed at between 100 and 1000 copies per cell. CR1 is the main system for processing and clearance of complement-opsonized immune complexes. CR1 negatively regulates the complement cascade, mediates immune adherence and phagocytosis, and inhibits both the classic and alternative complement pathways. The full-length CR1 protein comprises a 42 amino acid signal peptide, an extracellular domain of 1930 amino acids, a 25 amino acid transmembrane domain, and a 43 amino acid C-terminal cytoplasmic domain. The extracellular domain of CR1 has 25 potential N-glycosylation signal sequences, and comprises 30 short consensus ("SCR") domains, also known as complement control protein (CCP) repeats, or sushi domains, each 60 to 70 amino acids long. The sequence homology between SCRs ranges between 60-99 percent. The 30 SCR domains are further grouped into four longer regions termed long homologous repeats ("LHRs"), each encoding approximately 45 kDa segments of the CR1 protein, designated LHR-A, -B, -C, and -D. The first three comprise seven SCR domains each, while LHR-D comprises 9 SCR domains. The active sites on the extracellular domain of CR1 protein include a C4b-binding site with lower affinity for C3b in SCRs 1-4 comprising amino acids 42-295, a C3b-binding site with lower affinity for C4b in SCRs 8-11 comprising amino acids 490-745, a C3b-binding site with lower affinity for C4b in SCRs 15-18 comprising amino acids 940-1196, and a C1q-binding site in SCRs 22-28 comprising amino acids 1394-1842.

SEQ ID NO:51 represents the full-length human CR1 amino acid sequence (see, e.g., UniProtKB/Swiss-Prot. Accession No. P17927). Amino acids 1-41 correspond to the signal peptide, amino acids 42-2039 correspond to the mature protein, comprising amino acids 42-1971, corresponding to the extracellular domain, amino acids 1972-1996, corresponding to the transmembrane domain, and amino acids 1997-2039, corresponding to the cytoplasmic domain. In the extracellular domain, amino acids 42-101 correspond to SCR 1, 102-163 correspond to SCR2, amino acids 164-234 correspond to SCR3, amino acids 236-295 correspond to SCR4, amino acids 295-355 correspond to SCR5, amino acids 356-418 correspond to SCR6, amino acids 419-489 correspond to SCR7, amino acids 491-551 correspond to SCR8, amino acids 552-613 correspond to SCR9, amino acids 614-684 correspond to SCRIO, amino acids 686-745 correspond to SCR11, amino acids 745-805 correspond to SCR12, amino acids 806-868 correspond to SCR13, amino acids 869-939 correspond to SCR 14, amino acids 941-1001 correspond to SCR15, amino acids 1002-1063 correspond to SCR16, amino acids 1064-1134 correspond to SCR17, amino acids 1136-1195 correspond to SCR18, amino acids 1195-1255 correspond to SCR 19, amino acids 1256-1318 correspond to SCR 20, amino acids 1319-1389 correspond to SCR 21, amino acids 1394-1454 correspond to SCR 22, amino acids 1455-1516 correspond to SCR 23, amino acids 1517-1587 correspond to SCR 24, amino acids 1589-1648 correspond to SCR 25, amino acids 1648-1708 correspond to SCR 26, amino acids 1709-1771 correspond to SCR 27, amino acids 1772-1842 correspond to SCR 28, amino acids 1846-1906 correspond to SCR 29, amino acids 1907-1967 correspond to SCR 30. It is understood that species and strain variations exist for the disclosed peptides, polypeptides, and proteins, and that CR1 protein or biologically active fragments thereof encompass all species and strain variations. As used herein, the term "biologically active" fragment of CR1 protein refers to any soluble fragment of CR1 lacking the transmembrane domain and the cytoplasmic domain, including fragments comprising, consisting essentially of or consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 SCR domains, including any fragments of the full-length CR1 protein having some or all the complement inhibitory activity of the full-length CR1 protein.

As used herein, the term "complement factor H," "factor H," or "FH" refers to complement factor H, a single polypeptide chain plasma glycoprotein, including homologs thereof. The protein is composed of 20 conserved short consensus repeat (SCR) domains of approximately 60 amino acids, arranged in a continuous fashion like a string of beads, separated by short linker sequences of 2-6 amino acids each. Factor H binds to C3b, accelerates the decay of the alternative pathway C3-convertase (C3bBb), and acts as a cofactor for the proteolytic inactivation of C3b. In the presence of factor H, proteolysis by factor I results in the cleavage and inactivation of C3b. Factor H has at least three distinct binding domains for C3b, which are located within SCRs 1-4, SCRs 5-8, and SCRs 19-20. Each domain binds to a distinct region within the C3b protein: the N-terminal sites bind to native C3b; the second site, located in the middle region of factor H, binds to the C3c fragment and the site located within SCR19 and 20 binds to the C3d region. In addition, factor H also contains binding sites for heparin, which are located within SCR 7, SCRs 5-12, and SCR 20 of factor H and overlap with those of the C3b binding sites. Structural and functional analyses have shown that the domains for the complement inhibitory activity of factor H are located within the first four N-terminal SCR domains.

SEQ ID NO:52 represents the full-length human factor H amino acid sequence (see, e.g., UniProtKB/Swiss-Prot. Accession No. P08603); SEQ ID NO:53 represents the full-length mouse factor H amino acid sequence (see, e.g., UniProtKB/Swiss-Prot. Accession No. P06909). In the human factor H sequence, amino acids 1-18 of SEQ ID NO:52 correspond to the signal peptide, and amino acids 19-1231 of SEQ ID NO:52 correspond to the mature protein. Within that protein, amino acids 21-80 of SEQ ID NO:52 correspond to SCR 1, amino acids 85-141 of SEQ ID NO:52 correspond to SCR 2, amino acids 146-205 of SEQ ID NO:52 correspond to SCR 3, amino acids 210-262 of SEQ ID NO:52 correspond to SCR 4, and amino acids 267-320 of SEQ ID NO:52 correspond to SCR 5. In the mouse factor H sequence, amino acids 1-18 of SEQ ID NO:53 correspond to the signal peptide, and amino acids 19-1234 of SEQ ID NO:53 correspond to the mature protein. Within that protein, amino acids 19-82 of SEQ ID NO:53 correspond to SCR 1, amino acids 83-143 of SEQ ID NO:53 correspond to SCR 2, amino acids 144-207 of SEQ ID NO:53 correspond to SCR 3, amino acids 208-264 of SEQ ID NO:53 correspond to SCR 4, and amino acids 265-322 of SEQ ID NO:53 correspond to SCR 5. It is understood that species and strain variations exist for the disclosed peptides, polypeptides, and proteins, and that factor H or biologically active fragments thereof encompass all species and strain variations.

As used herein, the term "biologically active" fragment of factor H refers to any portion of a factor H protein having some or all the complement inhibitory activity of the full-length factor H protein, and includes, but is not limited to, factor H fragments comprising SCRs 1-4, SCRs 1-5, SCRs 1-8, SCRs 1-18, SCRs 19-20, or any homolog of a naturally-occurring factor H or fragment thereof, as described in detail below. In some embodiments, the biologically active fragment of factor H has one or more of the following properties: (1) binding to C-reactive protein (CRP), (2) binding to C3b, (3) binding to heparin, (4) binding to sialic acid, (5) binding to endothelial cell surfaces, (6) binding to cellular integrin receptor, (7) binding to pathogens, (8) C3b co-factor activity, (9) C3b decay-acceleration activity, and (10) inhibiting the alternative complement pathway.

SEQ ID NO: 59 represents the amino acid sequence for mannose-binding lectin-associated protein of 44 kDa (MAp44). MAp44 is an alternatively spliced product encoded by the MASP1 gene. In certain aspects, MAp44 is an inhibitor of lectin pathway activation.

Thus, in some embodiments, the inhibitor portion of the targeted molecule described herein comprises a complement inhibitor or biologically active fragment thereof. In some embodiments, the complement inhibitor is selected from the group consisting of human MCP, human DAF, mouse DAF, human CD59, mouse CD59 isoform A, mouse CD59 isoform B, mouse Crry protein, human CR1, human factor H, or mouse factor H, a Factor I, or a biologically active fragment thereof.

In some embodiments, the inhibitor portion comprises full-length human MCP (SEQ ID NO:44). In some embodiments, the complement inhibitor portion of the targeting construct comprises a biologically active fragment of human MCP (SEQ ID NO:44). In some embodiments, the biologically active fragment of human MCP is selected from the group consisting of SCRs 1-4 (amino acids 35-285 of SEQ ID NO:44), SCRs 1-4 plus the serine/threonine-rich domain (amino acids 35-326 of SEQ ID NO:44), and the extracellular domain of MCP (amino acids 35-343 of SEQ ID NO:44).'

In some embodiments, the inhibitor portion comprises full-length human DAF. In some embodiments, the inhibitor portion comprises a biologically active fragment of human DAF (SEQ ID NO:45). In some embodiments, the biologically active fragment of human DAF is selected from the group consisting of SCRs 1-4 (amino acids 25-285 of SEQ ID NO:45) and SCRs 1-4 plus the O-glycosylated serine/threonine-rich domain (amino acids 25-353 of SEQ ID NO:45). In some embodiments, the inhibitor portion comprises full-length mouse DAF (SEQ ID NO:46). In some embodiments, the inhibitor portion comprises a biologically active fragment of mouse DAF. In some embodiments, the biologically active fragment of mouse DAF is selected from the group consisting of SCRs 1-4 (amino acids 35-286 of SEQ ID NO:46) and SCRs 1-4 plus the O-glycosylated serine/threonine-rich domain (amino acids 35-362 of SEQ ID NO:46).

In some embodiments, the inhibitor portion comprises full-length human CD59 (SEQ ID NO:47). In some embodiments, the inhibitor portion comprises a biologically active fragment of human CD59 (SEQ ID NO:47). In some embodiments, the biologically active fragment of human CD59 comprises the extracellular domain of human CD59 lacking its GPI anchor (amino acids 26-101 of SEQ ID NO:47). In some embodiments, the inhibitor portion comprises full-length mouse CD59, isoform A (SEQ ID NO:48). In some embodiments, the inhibitor portion comprises a biologically active fragment of mouse CD59, isoform A (SEQ ID NO:48). In some embodiments, the biologically active fragment of mouse CD59, isoform A comprises the extracellular domain of mouse CD59, isoform A lacking its GPI anchor (amino acids 24-95 of SEQ ID NO:48). In some embodiments, the inhibitor portion comprises full-length mouse CD59, isoform B (SEQ ID NO:49). In some embodiments, the c inhibitor portion comprises a biologically active fragment of mouse CD59, isoform B (SEQ ID NO:49). In some embodiments, the biologically active fragment of mouse CD59, isoform B comprises the extracellular domain of mouse CD59, isoform lacking its GPI anchor (amino acids 24-103 of SEQ ID NO:49).

In some embodiments, the inhibitor portion comprises full-length mouse Crry protein (SEQ ID NO:50). In some embodiments, the inhibitor portion comprises a biologically active fragment of mouse Crry protein (SEQ ID NO:50). In some embodiments, the biologically active fragment of mouse Crry protein is selected from the group consisting of SCRs 1-5 (amino acids 41-400 of SEQ ID NO:50) and the extracellular domain of mouse Crry protein (amino acids 41-405 of SEQ ID NO:50). In one embodiment, the inhibitor portion comprises the biologically active fragment of mouse Crry comprising amino acids 85-403 of SEQ ID NO: 50.

In some embodiments, the inhibitor portion comprises full-length human CR1 protein (SEQ ID NO:51). In some embodiments, the t inhibitor portion comprises a biologically active fragment of human CR1 protein (SEQ ID NO:51). In some embodiments, the biologically active fragment of human CR1 protein is selected from the group consisting of SCRs 1-4 (amino acids 42-295 of SEQ ID NO:51), SCRs 1-10 (amino acids 42-684 of SEQ ID NO:51), SCRs 8-11 (amino acids 490-745 of SEQ ID NO:51), SCRs 15-18 (amino acids 940-1196 of SEQ ID NO:51), and SCRs 22-28 (amino acids 1394-1842 of SEQ ID NO:51).

In some embodiments, the inhibitor portion comprises full-length human (SEQ ID NO:52) or mouse (SEQ ID NO:53) factor H. In some embodiments, the inhibitor portion comprises a biologically active fragment of human (SEQ ID NO:52) or mouse (SEQ ID NO:53) factor H. In some embodiments, the biologically active fragment of human factor H (SEQ ID NO:52) is selected from the group consisting of SCRs 1-4 (amino acids 21-262 of SEQ ID NO:52), SCRs 1-5 of factor H (amino acids 21-320 of SEQ ID NO:52), SCRs 1-8 of factor H (amino acids 21-507 of SEQ ID NO:52), and SCRs 1-18 of factor H (amino acids 21-1104 of SEQ ID NO:52). In some embodiments, the biologically active fragment of mouse factor H (SEQ ID NO:53) is selected from the group consisting of SCRs 1-4 (amino acids 19-264 of SEQ ID NO:53), SCRs 1-5 of factor H (amino acids 19-322 of SEQ ID NO:53), SCRs 1-8 of factor H (amino acids 19-507 of SEQ ID NO:53), and SCRs 1-18 of factor H (amino acids 19-1109 of SEQ ID NO:53). In some embodiments, the biologically active fragment of human (SEQ ID NO:52) or mouse (SEQ ID NO:53) factor H comprises (and in some embodiments consists of or consists essentially of) at least the first four N-terminal SCR domains of factor H, including for example, at least any of the first 5, 6, 7, 8, 9, 10, 11, 12, 13, 14, 15, 16, 17, 18, or more N-terminal SCR domains of factor H.

In some embodiments, the inhibitor portion comprises MAp44 (SEQ ID NO:59). In some embodiments, the inhibitor portion comprises a biologically active fragment of MAp44 (SEQ ID NO: 59).

In some embodiments, the inhibitor portion of the targeted molecules is a homolog of any of the complement inhibitors described herein or a biologically active fragment thereof. Homologs of the complement inhibitors (or biologically active fragments thereof) include proteins which differ from a naturally occurring complement inhibitor (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition glycosylphosphatidyl inositol). For example, homologue of a complement inhibitor may have an amino acid sequence that is at least about 70% identical to the amino acid sequence of a naturally complement inhibitor (e.g., SEQ ID NOs:44-53, 59), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of a naturally occurring complement inhibitor (e.g., SEQ ID NOs:44-53). Amino acid sequence identity can be determined in various ways, for example, using publicly available computer software such as BLAST, BLAST-2, ALIGN or MEGALIGN™ (DNAST AR) software. One skilled in the art can determine appropriate parameters for measuring alignment, including any algorithms needed to achieve maximal alignment over the full length of the sequences being compared.

In certain embodiments, a homolog of complement inhibitor (or a biologically active fragment thereof) retains all the complement pathway inhibitory activity of the complement inhibitor (or a biologically active fragment thereof) from which it is derived. In certain embodiments, the homolog of a complement inhibitor (or a biologically-active fragment thereof) retains at least about 50%, for example, at least about any of 60%, 70%, 80%, 90%, or 95% of the complement inhibition activity the complement inhibitor (or a biologically-active fragment thereof) from which is derived.

In some embodiments, the inhibitor portion comprises an antibody (or an antigen binding fragment thereof) that binds to a complement component, e.g., a complement component selected from the group consisting of CI, Clq, Cis, C2, C2a, C3, C3a, C3b, C4, C4b, C5, C5a, C5b, C6, C7, C8, and C9. The complement polypeptides to which the antibodies or antigen binding fragments thereof bind can be, in some embodiments, human polypeptides, e.g., human CI, Clq, Cls, C2, C2a, C3, C3a, C3b, C4, C4b, C5, C5a, C5b, C6, C7, C8, C9, factor B, factor D, or properdin polypeptides. The amino acid sequences for the foregoing complement proteins are well-known in the art as are methods for preparing the proteins or fragments thereof for use in preparing an antibody (or antigen-binding fragment thereof) specific for one or more of the complement proteins. Suitable methods are also described and exemplified herein.

Exemplary anti-complement protein antibodies, which are suitable for incorporation into the targeted molecules described herein and for subsequent use in any of the methods described herein, are also well known in the art. For example, antibodies that bind to complement component C5 and inhibit the cleavage of C5 into fragments C5a and C5b include, e.g., eculizumab (Soliris®; Alexion Pharmaceuticals, Inc., Cheshire, Conn.) and pexelizumab (Alexion Pharmaceuticals, Inc., Cheshire, Conn.). See, e.g., Kaplan (2002) Curr Opin Investig Drugs 3(7): 1017-23; Hill (2005) Clin Adv Hematol Oncol 3(11):849-50; Rother et al. (2007) Nature Biotechnol 25(11): 1256-1488; Whiss (2002) Curr Opin Investig Drugs 3(6):870-7; Patel et al. (2005) Drugs Today (Bare) 41(3): 165-70; and Thomas et al. (1996) Mol Immunol. 33(17-18): 1389-401.

In some embodiments, the anti-C5 antibody can bind to an epitope in the alpha chain of the human complement component C5 protein. Antibodies that bind to the alpha chain of C5 are described in, for example, PCT application publication no. WO 2010/136311 and U.S. Pat. No. 6,355,245. In some embodiments, the anti-C5 antibody can bind to an epitope in the beta chain of the human complement component C5 protein. Antibodies that bind to the C5 beta chain are described in, e.g., Moongkarndi et al. (1982) Immunobiol 162:397; Moongkarndi et al. (1983) Immunobiol 165: 323; and Mollnes et al. (1988) Scand 1 Immunol 28:307-312.

Additional anti-C5 antibodies, and antigen-binding fragments thereof, suitable for use in the targeting constructs described herein are described in, e.g., PCT application publication no. WO 2010/015608, the disclosure of which is incorporated herein by reference in its entirety.

Antibodies that bind to C3b and, for example, inhibit the C3b convertase are also well known in the art. For example, PCT application publication nos. WO 2010/136311, WOb2009/056631, and WO 2008/154251, the disclosures of each of which are incorporated herein by reference in their entirety. Antagonistic anti-C6 antibodies and anti-C7 antibodies have been described in, e.g., Brauer et al. (1996) Transplantation 61(4):588-594 and U.S. Pat. No. 5,679,345.

In some embodiments, the inhibitor portion comprises an anti-factor B antibody (such as the monoclonal antibody 1379 produced by ATCC Deposit No. PTA-6230). Anti-factor B antibodies are also described in, e.g., Ueda et al. (1987) J Immunol 138(4): 1143-9; Tanhehco et al. (1999) Transplant Proc 31(5):2168-71; U.S. patent application publication nos. 20050260198 and 2008029911; and PCT publication no. WO 09/029669.

In some embodiments, the inhibitor portion comprises an anti-factor D antibody, e.g., an antibody described in Pascual et al. (1990) 1 Immunol Methods 127:263-269; Sahu et al. (1993) Mol Immunol 30(7):679-684; Pascual et al. (1993) Eur 1 Immunol 23: 1389-1392; Niemann et al. (1984) J Immunol 132(2):809-815; U.S. Pat. No. 7,439,331; or U.S. patent application publication no. 20080118506.

In some embodiments, the inhibitor portion comprises an anti-properdin antibody. Suitable anti-properdin antibodies are also well-known in the art and include, e.g., U.S. patent application publication nos. 20110014614 and PCT application publication no. WO2009110918.

In some embodiments, the inhibitor portion comprises an anti-MBL antibody. Mannose-binding mannan-binding lectin (MBL), a plasma protein, forms a complex with proteins known as MBL-associated serine proteases (MASPs). MBL binds to several monosaccharides that are uncharacteristic of mammalian proteins, e.g., mannose, N-acetylglucosamine, N-acetylmannoseamine, L-fucose and glucose, whereas sialic acid and galactose are not bound. When the MBL-MASP complex binds to microorganisms, the proenzymic forms of the serine proteases are activated and mediate the activation of complement components C4 and C2, thereby generating the C3 convertase C4b2b and leading to opsonization by the deposition of C4b and C3b fragments. MASP-2 has been shown to cleave C4 and C2, while MASP-1 may be responsible for direct cleavage of C3. The functions of MASP-3 and MAp19 are less well understood. Studies have shown a clear link between low levels of MBL and opsonic deficiency, as well as clinical manifestations such as severe diarrhea, chronic hepatitis and HIV infection, and autoimmune disease. See, Petersen et al., J. Immunological Methods, 257: 107-16 (2001); Petersen et al., Molecular Immunology, 38: 133-49 (2001). Anti-mannan-binding lectin antibodies are known in the art (see, e.g., Pradhan et al. (2012) Rheumatol. Int. epublished September, 2012) and commercially available (AbCam).

In some embodiments, the inhibitor portion comprises an anti-MASP antibody. The mannan-binding lectin-associated serine proteases (MASPs) are a family of at least three proteins (mannan-binding lectin-associated serine protease-1, -2 and -3 (MASP-1, MASP-2 and MASP-3, respectively)), which have been taught to play a significant role in modulation of the lectin pathway of complement activation. Petersen et al., Molecular Immunology 38: 133-149 (2001).

MASP-1 has a histidine loop structure of the type found in trypsin and trypsin-like serine proteases. MASP-1 has been found to be involved in complement activation by MBL. A cDNA clone encoding MASP-1 has been reported that encodes a putative leader peptide of 19 amino acids followed by 680 amino acid residues predicted to form the mature peptide. MASP-2 (MBL-associated serine protease 2) is a serine protease also similar in structure to CI r and CI s of the complement pathway. Like these, and contrary to MASP-1, it has no histidine loop structure of the type found in trypsin and trypsin-like serine proteases. It has been theorized that MASP-1 can cleave C3, generating C3b, which may be deposited on an activated cell or tissue surface It has been shown that MASP-2, cleaves C4 and C2, giving rise to the C3 convertase, C4b2b (Thiel et al., Nature, 386:506-10 (1997)). The MASP-2 protein comprises of a number of domains namely the CUB1, EGF, CUB2, CCP1, CCP2 and serine protease domains. It is believed that the domain responsible for association with MBL is situated in the N-terminus, whereas the serine protease domain is responsible for the serine protease activity of MASP-2. sMAP, also known as MAp19, is a 19 kd is derived from the same gene as MASP-2, which lacks the serine protease domain and a major part of the A chain. Skjoedt et al., Immunobiology, 215:921-31 (2010). Recently, a third member of the family, MASP-3 was identified, which shares a high degree of homology with MASP-1, such that it appears that MASP-1 and MASP-3 are generated as a result of alternative splicing of primary mRNA transcripts.

Antibodies against MBL, MASP-1, MASP-2, MASP-3 and the MBL/MASP complex, and their use for inhibiting the adverse effects of complement activation, such as ischemia-reperfusion injury, have been disclosed, for example, in WO04/075837; US 2009/0017031.

Other antibodies to MASP-2 have been described previously, as well. See, e.g., WO 02/06460, US2007/0009528, Peterson et al., Mol. Immunol. 37:803-11 (2000), MoUer-Kristensen et al., J. of Immunol. Methods 282: 159-67 (2003), Petersen et al., Mol. Immunol. 35:409, and WO 04/106384.

An additional related protein, MBL/Ficolin Associated Protein (MAP-1), which is present in low serum levels compared to MASP-1 and MASP-3, has been reported to function as a local lectin pathway specific complement inhibitor. Skjodt et al., Molecular Immunology, 47:2229-30 (2010). Accordingly, MAP-1 itself, or fragments of MAP-1, may be useful in the present invention as an inhibitor of MASP, and accordingly, as a lectin-pathway-specific inhibitor of complement activation. Finally, the ficolin family of proteins are characterized by carbohydrate binding and opsonic activities, sharing a structure similar to MBL. Like MBL, the ficolins have been shown to associate with MASPs in serum and may mediate complement activation in response to pathogenic, necrotic, or apoptotic cell-specific carbohydrate markers. Accordingly, inhibitors of the ficolin family or functional fragments thereof may be useful in the present invention as an inhibitor of MASPs and as a lectin-pathway specific inhibitor of complement activation. U.S.

Pat. Nos. 6,333,034 and 7,423,128; see also, WO 2008/154018 and WO 2009/110918.

In some embodiments, the inhibitor portion comprises an antibody (or antigen binding fragment thereof) that specifically binds to a human complement component protein (e.g., human C5, C6, C7, C8, or C9). The terms "specific binding" or "specifically binds" refer to two molecules forming a complex (e.g., a complex between an antibody and a complement component protein) that is relatively stable under physiologic conditions. Typically, binding is considered specific when the association constant (Ka) is higher than 106 M-1. Thus, an antibody can specifically bind to a C5 protein with a Ka of at least (or greater than) 106 (e.g., at least or greater than 107, 108, 109, 1010, 1011, 1012, 1013, 1014, or 1015 or higher) M-1. Examples of antibodies that specifically bind to a human complement component C5 protein are described in, e.g., U.S. Pat. No. 6,355,245 and PCT application publication no. WO 2010/015608.

Methods for determining whether an antibody binds to a protein antigen and/or the affinity for an antibody to a protein antigen are known in the art and described herein. For example, the binding of an antibody to a protein antigen can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), or enzyme-linked immunosorbent assay (ELISA) assays. See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2nd Edition, Oxford University Press, NY, Oxford; Johne et al. (1993) 1 Immunol Meth. 160: 191-198; Jonsson et al. (1993) Ann Biol Clin 51: 19-26; and Jonsson et al. (1991) Biotechniques 11:620-627. See also, U.S. Pat. No. 6,355,245.

In any of the embodiments described herein, the targeted molecule also includes an amino acid linker sequence linking the targeting portion and the inhibitor portion.

In some embodiments, a targeted molecule described herein comprises more than one (e.g., two, three, four, five, six, or seven or more) inhibitor portion e.g., more than one complement inhibitor polypeptide or drug described herein. The two or more inhibitor portions can be the same or different. For example, a targeted molecule described herein can comprise, in some embodiments, two or more soluble CD59 portions (e.g., soluble human CD59 portions). In another example, a targeted molecule described herein can contain two or more complement inhibitor polypeptide portions, wherein one is a soluble human CD59 and another is soluble human MCP. In another example, a targeted molecule described herein can contain a complement inhibitor and a drug, e.g., one soluble CD59 portion and one corticosteroid. Thus, e.g., a targeted molecule described herein can comprise: (a) a targeting portion (e.g., a C2 antibody, a B4 antibody, or an antigen-binding fragment of either of the foregoing); (b) a first inhibitor portion (e.g., a soluble form of CD59, e.g., human CD59); and (c) a second inhibitor portion (e.g., a soluble form of DAF, e.g., a soluble form of human DAF, or a corticosteroid such as prednisone). The inhibitor portion can be, e.g., any of those described herein including variants and biologically active fragments of the complement inhibitors described herein.

In some embodiments, the light chain of the targeting portion of the targeted molecule comprises at least one inhibitor portion and the heavy chain comprises at least one inhibitor portion. The two or more inhibitor portions can be the same or different. For example, in some embodiments, the targeted molecule comprises the Fab fragment of a targeting portion described herein, wherein: (i) the light chain of the Fab fragment comprises (at its C-terminal end) an inhibitor portion such as DAF, CD59, or any of the complement inhibitor polypeptides described herein and (ii) the heavy chain of the Fab fragment comprises (at its C-terminal end) the same or a different inhibitor portion as in (i), e.g., a complement inhibitor or a drug described herein. Appropriate pairing of the two chains can be expected to occur as an inherent property of the Fab. The inhibitor portion and the light chain or heavy chain of the Fab can be joined together directly or by way of a linker sequence (such as any of those described herein).

In one embodiment, the targeted molecule comprises B4Crry comprising the amino acid sequence of SEQ ID NO: 62. An exemplary nucleotide sequence encoding B4Crry is provided in SEQ ID ON: 61. In one embodiment, the targeted molecule comprises a homolog or biologically active fragment of B4Crry. Homologs of the B4Crry include proteins which differ from B4Crry described herein (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition glycosylphosphatidyl inositol). For example, homologue of B4Crry may have an amino acid sequence that is at least about 70% identical to the amino acid sequence B4Crry (e.g., SEQ ID NO: 62), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of B4Crry (e.g., SEQ ID NO: 62). Amino acid sequence identity can be determined in various ways, for example, using publicly available computer software such as BLAST, BLAST-2, ALIGN or MEGALIGN™ (DNASTAR) software. One skilled in the art can determine appropriate parameters for measuring alignment, including any algorithms needed to achieve maximal alignment over the full length of the sequences being compared.

In one embodiment, the targeted molecule comprises C2Crry comprising the amino acid sequence of SEQ ID NO: 64. An exemplary nucleotide sequence encoding C2Crry is provided in SEQ ID NO: 63. In one embodiment, the targeted molecule comprises a homolog or biologically active fragment of C2Crry. Homologs of the C2Crry include proteins which differ from C2Crry described herein (or biologically-active fragment thereof) in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition glycosylphosphatidyl inositol). For example, homologue of C2Crry may have an amino acid sequence that is at least about 70% identical to the amino acid sequence C2Crry (e.g., SEQ ID NO: 64), for example at least about any of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of C2Crry (e.g., SEQ ID NO: 64). Amino acid sequence identity can be determined in various ways, for example, using publicly available computer software such as BLAST, BLAST-2, ALIGN or MEGALIGN™ (DNASTAR) software. One skilled in the art can determine appropriate parameters for measuring alignment, including any algorithms needed to achieve maximal alignment over the full length of the sequences being compared.

Preparation of Targeted Molecules

The molecules (described herein may be made by chemical synthesis methods, or by linkage of a polynucleotide encoding the targeting portion (e.g. B4 or C2 antibody or fragment thereof) and a polynucleotide encoding the inhibitor portion (with or without a linker sequence), and introducing the resulting polynucleotide molecule in a vector for transfecting host cells that are capable of expressing the molecule. Chemical synthesis, especially solid phase synthesis, is preferred for short peptides or those containing unnatural or unusual amino acids such as D-Tyr, Ornithine, and the like. Recombinant procedures are preferred for longer polypeptides. The molecule can be isolated in vitro by protein purification methods. The molecule can also be provided "in situ" by introduction of a gene therapy system to the tissue of interest which then expresses the molecule.

Recombinant DNA techniques for making a fusion protein involves, in simplified form, taking the fusion protein encoding polynucleotide, inserting it into an appropriate vector, inserting the vector into an appropriate host cell, and recovering or isolating the fusion protein produced thereby.

Provided herein are polynucleotides that encode the molecule. Such polynucleotide may also be used for delivery and expression of molecule. For example, in some embodiments, there is provided a polynucleotide encoding a fusion protein comprising a targeting portion comprising an antibody or a fragment thereof described herein, and an inhibitor portion comprising an intact inhibitor molecule or a fragment thereof. In some embodiments, the polynucleotide also comprises a sequence encoding a signal peptide operably linked at the 5' end of the sequence encoding the fusion protein. In some embodiments, a linker sequence is used for linking the targeting portion and the inhibitor portion Also provided are expression vectors comprising a polynucleotide described herein for expression of the fusion protein. The expression vector can be used to direct expression of a fusion protein in vitro or in vivo. The vector may include any element to establish a conventional function of a vector, for example, promoter, terminator, selection marker, and origin of replication. The promoter can be constitutive or regulative, and is selected from, for example, promoters of genes for galactokinase (GAL1), uridylyltransferase (GALT), epimerase (GAL10), phosphoglycerate kinase (PGK), glyceraldehydes-3-phosphate dehydrogenase (GPD), alcohol dehydrogenase (ADH), and the like.

Many expression vectors are known to those of skill in the art. For example, E. coli may be transformed using pBR322, a plasmid derived from an E. coli species (Mandel et al., J. Mol. Biol., 53:154 (1970)). Plasmid pBR322 contains genes for ampicillin and tetracycline resistance, and thus provides easy means for selection. Other vectors include different features such as different promoters, which are often important in expression. For example, plasmids pKK223-3 (Pharmacia Fine Chemicals, Uppsala, Sweden), pKK233-2 (Clontech, Palo Alto, Calif., USA), and pGEM1 (Promega Biotech, Madison, Wis., USA), are all commercially available. Other vectors that can be used in the present invention include, but are not limited to, pET21a (Studier et al., Methods Enzymol., 185: 60-89 (1990)), pR1T5, and pR1T2T (Pharmacia Biotechnology), and pB0475 (Cunningham et al., Science, 243: 1330-1336 (1989); U.S. Pat. No. 5,580,723). Mammalian expression vectors may contain non-transcribed elements such as an origin of replication, promoter and enhancer, and 5' or 3' nontranslated sequences such as ribosome binding sites, a polyadenylation site, acceptor site and splice donor, and transcriptional termination sequences. Promoters for use in mammalian expression vectors usually are for example viral promoters such as Polyoma, Adenovirus, HTLV, Simian Virus 40 (SV 40), and human cytomegalovirus (CMV). Vectors can also be constructed using standard techniques by combining the relevant traits of the vectors described above.

Also provided are host cells (such as isolated cells, transient cell lines, and stable cell lines) for expressing the molecule described herein. The host cell may be prokaryotic or eukaryotes. Exemplary prokaryote host cells include E. coli K12 strain 294 (ATCC No. 31446), E. coli B, E. coli X1776 (ATCC No. 31537), E. coli W3110 (F-, gamma-, prototrophic/ATCC No. 27325), bacilli such as Bacillus subtilis, and other enterobacteriaceae such as Salmonella typhimurium or Serratia marcesans, and various Pseudomonas species. One suitable prokaryotic host cell is E. coli BL21 (Stratagene), which is deficient in the OmpT and Lon proteases, which may interfere with isolation of intact recombinant proteins, and useful with T7 promoter-driven vectors, such as the pET vectors. Another suitable prokaryote is E. coli W3110 (ATCC No. 27325). When expressed by prokaryotes the peptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic microbes such as filamentous fungi or yeast are suitable cloning or expression hosts for fusion-protein-encoding vectors. Saccharomyces cerevisiae is a commonly used lower eukaryotic host microorganism. Others include Schizosaccharomyces pombe (Beach and Nurse, Nature, 290: 140 (1981); EP 139,383 published 2 May 1985); Kluyveromyces hosts (U.S. Pat. No. 4,943,529; Fleer et al., Bio/Technology, 9:968-975 (1991)) such as, e.g., K. lactis (MW98-8C, CBS683, CBS4574; Louvencourt et al., J. Bacteriol., 154(2):737-742 (1983)), K. fragilis (ATCC 12,424), K. bulgaricus (ATCC No. 16,045), K. wickeramii (ATCC No. 24,178), K. waltii (ATCC No. 56,500), K. drosophilarum (ATCC No. 36,906; Van den Berg et al., Bio/Technology, 8:135 (1990)), K. thermotolerans, and K. marxianus; yarrowia (EP 402,226); Pichia pastoris (EP 183,070; Sreekrishna et al., J. Basic Microbiol., 28:265-278 (1988)); Candida; Trichoderma reesia (EP 244, 234); Neurospora crassa (Case et al., Proc. Natl. Acad. Sci. USA, 76:5259-5263 (1979)); Schwanniomyces such as Schwanniomyces occidentalis (EP 394,538 published 31 Oct. 1990); and filamentous fungi such as, e.g., Neurospora, Penicillium, Tolypocladium (WO 91/00357 published 10 Jan. 1991), and Aspergillus hosts such as A. nidulans (Ballance et al., Biochem. Biophys. Res. Commun., 112:284-289 (1983); Tilburn et al., Gene, 26:205-221 (1983); Yelton et al., Proc. Natl. Acad. Sci. USA, 81: 1470-1474 (1984)) and A. niger (Kelly and Hynes, EMBO J., 4:475-479 (1985)). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, The Biochemistry of Methylotrophs, 269 (1982). Host cells also include insect cells such as *Drosophila* S2 and *Spodoptera* Sf9, as well as plant cells.

Examples of useful mammalian host cell lines include, but are not limited to, HeLa, Chinese hamster ovary (CHO), COS-7, L cells, C127, 3T3, BHK, CHL-1, NSO, HEK293, WI38, BHK, C127 or MDCK cell lines. Another exemplary mammalian cell line is CHL-1. When CHL-1 is used hygromycin is included as a eukaryotic selection marker. CHL-1 cells are derived from RPMI 7032 melanoma cells, a readily available human cell line. Cells suitable for use in this invention are commercially available from the ATCC.

In some embodiments, the host cell is a non-human host cell. In some embodiment, the host cell is a CHO cell. In some embodiments, the host cell is a 293 cell.

The molecules can be isolated by a variety of methods known in the art. In some embodiments, when the molecule is a fusion protein secreted into the growth media, the molecule can be purified directly from the media. If the fusion protein is not secreted, it is isolated from cell lysates. Cell disruption can be done by any conventional method, including freeze-thaw cycling, sonication, mechanical disruption, or use of cell lysing agents. The molecules can be obtained by various methods. These include, but are not limited to, immunoaffinity chromatography, reverse phase chromatography, cation exchange chromatography, anion exchange chromatography, hydrophobic interaction chromatography, gel filtration chromatography, and HPLC. For example, the molecule can be purified by immunoaffinity chromatography using an antibody that recognizes the targeting portion or an antibody that recognizes the inhibitor portion, or both. In some embodiments, the molecule is purified by ion change chromatography.

The peptide may or may not be properly folded when expressed as a fusion protein. These factors determine whether the fusion protein must be denatured and refolded, and if so, whether these procedures are employed before or after cleavage. When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

The molecules described herein may also contain a tag (such as a cleavable tag) for purification. This tag can be fused to the C-terminus or N-terminus of the targeting portion or the inhibitor portion, and can be used to facilitate protein purification.

In some embodiments, the molecule could be synthesized de novo in whole or in part, using chemical methods well known in the art. For example, the component amino acid sequences can be synthesized by solid phase techniques, cleaved from the resin, and purified by preparative high performance liquid chromatography followed by chemical linkage to form a desired polypeptide. The composition of the synthetic peptides may be confirmed by amino acid analysis or sequencing.

The molecules can be assayed for their desired properties using in vitro or in vivo assays, for example surface plasmon resonance or in vitro zymosan complement assay.

Targeted Molecules in Combination with a Thrombolytic Agent

In one aspect, the present invention relates to a composition comprising a thrombolytic agent in combination with a targeted molecule described herein. In one embodiment, the composition comprises a sub-therapeutic amount of a thrombolytic agent in combination with a targeted molecule. In one embodiment, the thrombolytic agent is selected from a list comprising but not limited to t-PA, urokinase, anistreplase, ancrod, and brinase.

In certain embodiments, the composition comprises an amount of the thrombolytic agent that is less than the amount necessary when the thrombolytic agent is administered alone. For example, in certain embodiments, the amount or concentration of the thrombolytic agent, when administered in combination with a targeted complement inhibitor described herein, is about 1%, 5%, 10%, 20%, 30%, 40%, 50%, 60%, 70%, 80%, 90%, or 95% of the amount or concentration of the thrombolytic agent that is efficacious when administered alone.

Uses of Targeted Molecules and Compositions Thereof

The targeted molecules described herein can function to specifically inhibit in vivo complement activation in the complement pathway and inflammatory manifestations that accompany it, such as recruitment and activation of macrophages, neutrophils, platelets, and mast cells, edema, tissue damage, and direct activation of local and endogenous cells. Compositions comprising these molecules can therefore be used for treatment of diseases or conditions that are mediated by excessive or uncontrolled activation of the complement system, particularly diseases or conditions mediated by excessive or uncontrolled activation of complement signaling. In some embodiments, there are provided methods of treating diseases involving local inflammation process.

In some embodiments, there is provided a method of treating a disease in which complement signaling is implicated in an individual, comprising administering to the individual an effective amount of a composition comprising a targeted molecule comprising: a) a targeting portion comprising an antibody or a fragment thereof, and b) an inhibitor portion comprising an inhibitor (for example a complement inhibitor) or a fragment thereof. In some embodiments, there is provided a method of inhibiting complement activation in an individual having a disease associated with complement activation, comprising administering to the individual an effective amount of a composition comprising a targeted molecule comprising: a) a targeting portion comprising an antibody or a fragment thereof, and b) an inhibitor portion comprising an inhibitor molecule or a fragment thereof. In some embodiments, there is provided a method of inhibiting inflammation in an individual having a disease associated with complement activation, comprising administering to the individual an effective amount of a composition comprising a targeted molecule comprising: a) a targeting portion comprising an antibody or a fragment thereof, and b) an inhibitor portion comprising an inhibitor or a fragment thereof.

In some embodiments, the disease to be treated is ischemia reperfusion injury. Ischemia reperfusion (I/R) injury refers to inflammatory injury to the endothelium and underlying parenchymal tissues following reperfusion of hypoxic tissues. Ischemia reperfusion injury can result in necrosis and irreversible cell injury. The complement pathway (including the alternative complement pathway) is a major mediator of I/R injury. Methods provided herein are thus useful for treatment of ischemia reperfusion that occurs in any organ or tissues, such as ischemia-reperfusion injury of any transplanted organ or tissue. Other conditions and diseases in which ischemia-reperfusion injury occurs will be known to those of skill in the art.

In one aspect, the present invention provides a method of treating a subject having, or who has had, an ischemic stroke, traumatic brain injury, or spinal cord injury. In certain embodiments, the method comprises administering to the subject one or more of the targeted molecules described herein. In certain embodiments, the method comprises the use of one or more targeted molecules described herein as an adjuvant therapy in combination with one or more standard therapies. For example, in certain embodiments, the one or more targeted molecules are used in combination with rehabilitation therapy.

Exemplary types of rehabilitation therapy include, but is not limited to, motor therapy, mobility training, constraint-induced therapy, range-of-motion therapy, electrical and magnetic stimulation, robot-assisted therapy, physical therapy, occupational therapy, speech therapy, cognitive therapy, visual rehabilitation and the like.

In one embodiment, the method comprises administering one or more targeted molecules as described herein in combination with one or more thrombolytic agents. For example, in one embodiment, the method comprises administering to the subject a composition comprising a targeted molecule and a thrombolytic agent. In one embodiment, the method comprises administering to the subject a first composition comprising a targeted molecule and a second composition comprising a thrombolytic agent.

In certain aspects, the composition is administered to the subject within 1 minute, 5 minutes, 10 minutes, 15 minutes, 30 minutes, 1 hour, 2 hours, 4 hours, 6 hours, 8 hours, 12 hours, 18 hours, 1 day, 2 days, 3 days, 4 days, 5 days, 6 days, 7 days, 10 days, 2 weeks, 4 weeks, or more following the onset of stroke or injury. In certain aspects the use of the composition as an adjuvant therapy in combination with one or more other therapies increases the therapeutic window for the treatment of stroke, traumatic brain injury, or spinal cord injury.

Administration

The compositions described herein can be administered to an individual via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intrathecal, transdermal, transpleural, topical, inhalational (e.g., as mists of sprays), mucosal (such as via nasal mucosa), gastrointestinal, intraarticular, intracisternal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection in intracerebral injection).

Combination Therapy

In some embodiments, provided pharmaceutical formulations are administered to a subject in combination with one or more other therapeutic agents or modalities, for example, useful in the treatment of one or more diseases, disorders, or conditions treated by the relevant provided pharmaceutical formulation, so the subject is simultaneously exposed to both. In some embodiments, a composition is utilized in a pharmaceutical formulation that is separate from and distinct from the pharmaceutical formulation containing the other therapeutic agent. In some embodiments, a composition is admixed with the composition comprising the other therapeutic agent. In other words, in some embodiments, a composition is produced individually, and the composition is simply mixed with another composition comprising another therapeutic agent.

The particular combination of therapies (substances and/or procedures) to employ in a combination regimen will take into account compatibility of the desired substances and/or procedures and the desired therapeutic effect to be achieved. In some embodiments, provided formulations can be administered concurrently with, prior to, or subsequent to, one or more other therapeutic agents (e.g., desired known immunosuppressive therapeutics).

It will be appreciated that the therapies employed may achieve a desired effect for the same disorder or they may achieve different effects. In some embodiments, compositions in accordance with the invention are administered with a second therapeutic agent.

As used herein, the terms "in combination with" and "in conjunction with" mean that the provided formulation can be administered concurrently with, prior to, or subsequent to, one or more other desired therapeutics such as a rehabilitation therapy. In general, each substance will be administered at a dose and/or on a time schedule determined for that agent.

In certain embodiments, the method comprises administering a composition comprising a combination of a thrombolytic agent and a targeted inhibitor described herein. For example, in one embodiment the method comprises administering a composition comprising t-PA and a targeted inhibitor described herein.

In certain embodiments, the method comprises administering one or more compositions. For example, in one embodiment, the method comprises administering a first composition comprising a thrombolytic agent and a second composition comprising a targeted inhibitor described herein. In one embodiment, the method comprises administering a first composition comprising t-PA and a second composition comprising a targeted inhibitor described herein. The different compositions may be administered to the subject in any order and in any suitable interval. For example, in certain embodiments, the one or more compositions are administered simultaneously or near simultaneously. In certain embodiments, the method comprises a staggered administration of the one or more compositions, where a first composition is administered and a second composition administered at some later time point. Any suitable interval of administration which produces the desired therapeutic effect may be used.

In certain embodiments, the method has an additive effect, wherein the overall effect of the administering a combination of therapeutic agents or procedures is approximately equal to the sum of the effects of administering each therapeutic agent or procedure alone. In other embodiments, the method has a synergistic effect, wherein the overall effect of administering a combination of therapeutic agents or procedures is greater than the sum of the effects of administering each therapeutic agent or procedure alone.

Pharmaceutical Compositions

Also provided herein are pharmaceutical compositions comprising a targeted molecule described herein and a pharmaceutically acceptable carrier. The pharmaceutical compositions may be suitable for a variety of modes of administration described herein, including for example systemic or localized administration. The pharmaceutical compositions can be in the form of eye drops, injectable solutions, or in a form suitable for inhalation (either through the mouth or the nose) or oral administration. The pharmaceutical compositions described herein can be packaged in single unit dosages or in multidosage forms.

In some embodiments, the pharmaceutical compositions comprise a pharmaceutically acceptable carrier suitable for administration to human. In some embodiments, the pharmaceutical compositions comprise a pharmaceutically acceptable carrier suitable for intraocular injection. In some embodiments, the pharmaceutical compositions comprise a pharmaceutically acceptable carrier suitable for topical application. In some embodiments, the pharmaceutical compositions comprise a pharmaceutically acceptable carrier suitable for intravenous injection. In some embodiments, the pharmaceutical compositions comprise and a pharmaceutically acceptable carrier suitable for injection into the arteries.

The compositions are generally formulated as sterile, substantially isotonic, and in full compliance with all Good Manufacturing Practice (GMP) regulations of the U.S. Food and Drug Administration. In some embodiments, the composition is free of pathogen. For injection, the pharmaceutical composition can be in the form of liquid solutions, for example in physiologically compatible buffers such as Hank's solution or Ringer's solution. In addition, the pharmaceutical composition can be in a solid form and redissolved or suspended immediately prior to use. Lyophilized compositions are also included.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

The present invention in some embodiments provides compositions comprising a targeted molecule and a pharmaceutically acceptable carrier suitable for administration to the eye. Such pharmaceutical carriers can be sterile liquids, such as water and oil, including those of petroleum, animal, vegetable or synthetic origin, such as peanut oil, soybean oil, mineral oil, and the like. Saline solutions and aqueous dextrose, polyethylene glycol (PEG) and glycerol solutions can also be employed as liquid carriers, particularly for injectable solutions. Suitable pharmaceutical excipients include starch, glucose, lactose, sucrose, gelatin, malt, rice, sodium state, glycerol monostearate, glycerol, propylene, water, and the like. The pharmaceutical composition, if desired, can also contain minor amounts of wetting or emulsifying agents, or pH buffering agents. The molecule and other components of the composition may be encased in polymers or fibrin glues to provide controlled release of the molecule. These compositions can take the form of solutions, suspensions, emulsions, ointment, gel, or other solid or semisolid compositions, and the like. The compositions typically have a pH in the range of 4.5 to 8.0. The compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

In some embodiment, the composition is formulated in accordance with routine procedures as a pharmaceutical composition adapted for injection intravenously, intraperitoneally, or intracranially. Typically, compositions for injection are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions may further comprise additional ingredients, for example preservatives, buffers, tonicity agents, antioxidants and stabilizers, nonionic wetting or clarifying agents, viscosity-increasing agents, and the like.

Suitable preservatives for use in a solution include polyquaternium-1, benzalkonium chloride, thimerosal, chlorobutanol, methyl paraben, propyl paraben, phenylethyl alcohol, edetate disodium, sorbic acid, benzethonium chloride, and the like. Typically (but not necessarily), such preservatives are employed at a level of from 0.001% to 1.0% by weight.

Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5.

Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

The use of viscosity enhancing agents to provide topical compositions with viscosities greater than the viscosity of simple aqueous solutions may be desirable. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

In some embodiments, there is provided a pharmaceutical composition for delivery of a nucleotide encoding the molecule. The pharmaceutical composition for gene therapy can be in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical composition can comprise one or more cells which produce the gene delivery system.

In clinical settings, a gene delivery system for a gene therapeutic can be introduced into a subject by any of a number of methods. For instance, a pharmaceutical composition of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter, See U.S. Pat. No. 5,328,470, or by stereotactic injection, Chen et al. (1994), Proc. Natl. Acad. Sci., USA 91: 3054-3057. A polynucleotide encoding a targeted inhibitor molecule can be delivered in a gene therapy construct by electroporation using techniques described, Dev et al. (1994), Cancer Treat. Rev. 20:105-115.

Dosing

The optimal effective amount of the compositions can be determined empirically and will depend on the type and severity of the disease, route of administration, disease progression and health, mass and body area of the individual. Such determinations are within the skill of one in the art. The effective amount can also be determined based on in vitro complement activation assays. Examples of dosages of molecules which can be used for methods described herein include, but are not limited to, an effective amount within the dosage range of any of about 0.01 mg/kg to about 300 mg/kg, or within about 0.1 mg/kg to about 40 mg/kg, or with about 1 mg/kg to about 20 mg/kg, or within about 1 mg/kg to about 10 mg/kg. In some embodiments, the amount of composition administered to an individual is about 10 mg to about 500 mg per dose, including for example any of about 10 mg to about 50 mg, about 50 mg to about 100 mg, about 100 mg to about 200 mg, about 200 mg to about 300 mg, about 300 mg to about 500 mg, about 500 mg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose.

The compositions may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgical implantation in various locations.

Dosage amounts and frequency will vary according the particular formulation, the dosage form, and individual patient characteristics. Generally speaking, determining the dosage amount and frequency for a particular formulation, dosage form, and individual patient characteristic can be accomplished using conventional dosing studies, coupled with appropriate diagnostics.

Unit Dosages, Articles of Manufacture, and Kits

Also provided are unit dosage forms of compositions, each dosage containing from about 0.01 mg to about 50 mg, including for example any of about 0.1 mg to about 50 mg, about 1 mg to about 50 mg, about 5 mg to about 40 mg, about 10 mg to about 20 mg, or about 15 mg of the targeted molecule. In some embodiments, the unit dosage forms of targeted molecule composition comprise about any of 0.01 mg-0.1 mg, 0.1 mg-0.2 mg, 0.2 mg-0.25 mg, 0.25 mg-0.3 mg, 0.3 mg-0.35 mg, 0.35 mg-0.4 mg, 0.4 mg-0.5 mg, 0.5 mg-1.0 mg, 10 mg-20 mg, 20 mg-50 mg, 50 mg-80 mg, 80 mg-100 mg, 100 mg-150 mg, 150 mg-200 mg, 200 mg-250 mg, 250 mg-300 mg, 300 mg-400 mg, or 400 mg-500 mg targeted inhibitor molecule. In some embodiments, the unit dosage form comprises about 0.25 mg targeted molecule. The term "unit dosage form" refers to a physically discrete unit suitable as unitary dosages for an individual, each unit containing a predetermined quantity of active material calculated to produce the desired therapeutic effect, in association with a suitable pharmaceutical carrier, diluent, or excipient. These unit dosage forms can be stored in suitable packaging in single or multiple unit dosages and may also be further sterilized and sealed.

The present invention also provides kits comprising compositions (or unit dosages forms and/or articles of manufacture) described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing any methods described herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: The Use of B4Crry and t-PA for Treating Stroke

Experiments were conducted to examine the effects of administering B4Crry, t-PA, or the combination of B4Crry and t-PA in treating stroke. It is demonstrated herein that the combination of B4Crry and t-PA reduces t-PA associated hemorrhage and extends the window of efficacy of t-PA therapy.

In order to assess the interaction between B4Crry and t-PA treatment, experiments were conducted using a microembolic model of ischemic stroke. In this model, high dose emboli (1×10⁷ clots) homogenized to a diameter or 2-7 μm were injected via a catheter to the origin of middle cerebral artery. Following injection of emboli, B4Crry (16 mg/kg), t-PA (8 mg/kg), or both B4Crry and t-PA were administered at 2, 4, or 6 hours after emboli administration. Animals were assessed for survival over 72 hours and assessed daily for neurological deficit up to 72 hours. A different subset of animals was euthanized at 48 hours for brain extraction, homogenization and assessment of hemoglobin content (via Drabkin reagent approach), and complement activation (via C3a ELISA).

Experiments were conducted to examine the effects of administering B4Crry, t-PA, or the combination of B4Crry and t-PA 2 hours after stroke (FIG. 1A-FIG. 1E).

It was observed that all treatment groups had comparable acute survival up to 3-days after microemboli administration (FIG. 1A). However, a significant reduction in ipsilateral hemoglobin content 48 hours after MCAO was observed when treated with B4Crry alone or in combination with t-PA but not by t-PA alone (FIG. 1B). A C3a ELISA was performed 48 hours after microemboli administration. A significant effect of B4Crry and not t-PA on reducing post-stroke complement C3 cleavage was observed (FIG. 1C). Neurological deficit of animals 72 hours after microemboli administration was measured, which showed reduction in deficits in all three treatment groups (FIG. 1D). The infarct volume was assessed by TTC staining showing a significant reduction in infarct in all treatment groups at 72 hours after microemboli administration (FIG. 1E). Collectively, these experiments demonstrate that the combination of B4Crry and t-PA reduces t-PA associated hemorrhage and improves survival when administered 2 hours after stroke.

Experiments were also conducted to examine the effects of administering B4Crry, t-PA, or the combination of B4Crry and t-PA 4 hours after stroke (FIG. 2A-FIG. 2E).

Kaplan-Meyer survival curves show reduction in survival with t-PA therapy that is nearly statistically significant (FIG. 2A). FIG. 2B illustrates hemoglobin content in the ipsilateral hemisphere 48 hours after MCAO showing a significant increase in hemoglobin by t-PA alone that is reversed in animals receiving co-treatment with B4Crry. A C3a ELISA was performed 48 hours after microemboli administration showing comparable levels of C3a in vehicle and t-PA treated animals and a near significant reduction in levels in animals treated with B4Crry (FIG. 2C). FIG. 2D depicts neurological deficit of animals 72 hours after microemboli administration showing significant reduction in deficits in all three treatment groups. Infarct volume was assessed by TTC staining, showing a significant reduction in infarct only in animals co-treated with B4Crry and t-PA (FIG. 2E). One-way ANOVA with Bonferroni's test for multiple comparisons. N=6/group. *P<0.05 compared to vehicle. Collectively, these experiments demonstrate that the combination of B4Crry and t-PA reduces t-PA associated hemorrhage and improves survival when administered 4 hours after stroke.

Experiments were also conducted to examine the effects of administering B4Crry, t-PA, or the combination of B4Crry and t-PA 6 hours after stroke (FIG. 3A-FIG. 3E).

Kaplan-Meyer survival curves demonstrate significant reduction in survival compared to vehicle in animals treated with t-PA but not co-treated with B4Crry (FIG. 3A). FIG. 3B depicts Hemoglobin content in the ipsilateral hemisphere 48 hours after MCAO showing a significant increase in hemoglobin by t-PA alone that is reversed in animals receiving co-treatment with B4Crry. A C3a ELISA was performed 48 hours after microemboli administration showing comparable levels of C3a in vehicle and t-PA treated animals and a significant reduction in levels in animals treated with B4Crry (FIG. 3C). FIG. 3D depicts results indicating neurological deficit of animals 72 hours after microemboli administration showing significant reduction in deficits only in animals receiving co-therapy compared to vehicle control. Infarct volume assessed by TTC staining showing a significant reduction in infarct in animals co-treated with B4Crry and t-PA compared to vehicle or t-PA only (FIG. 3C). Collectively, these experiments demonstrate that the combination of B4Crry and t-PA reduces t-PA associated hemorrhage and improves survival when administered 4 hours after stroke.

It is noted that the the same vehicle animals were used in the experiments depicted in FIG. 1-FIG. 3. The experiments presented herein demonstrate that combination of B4Crry and t-PA reduces t-PA associated hemorrhage and extends the window of efficacy of t-PA therapy.

Figure 4B:
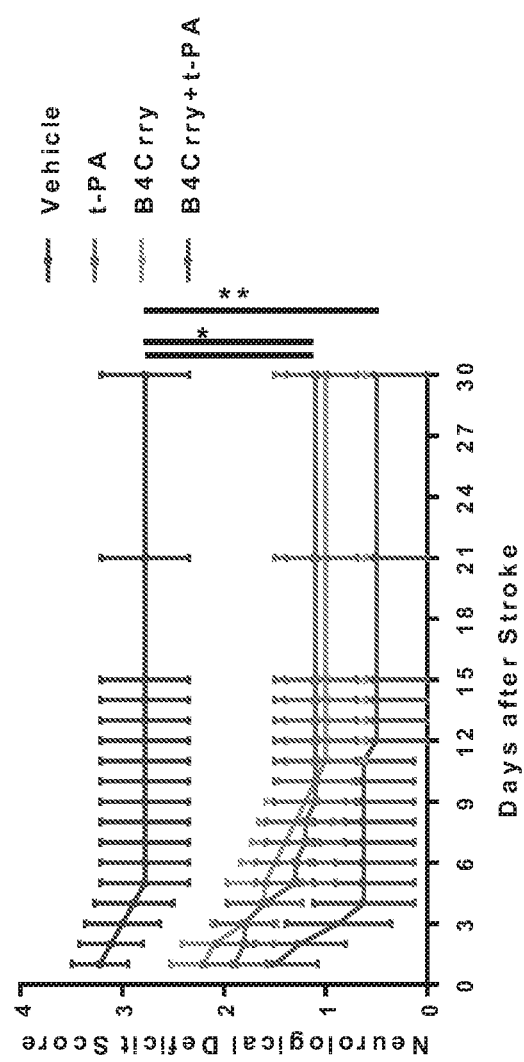
FIG. 4B depicts neurological deficit scores showing that B4Crry, t-PA and more effectively their combination significantly improve recovery of function deficits over 30 days of recovery after microembolic stroke and standard care. Kruskal-Wallis test with Bonferroni's test for multiple comparisons. N=8-12/group. *P<0.05. **P<0.05.
Figure 4C:
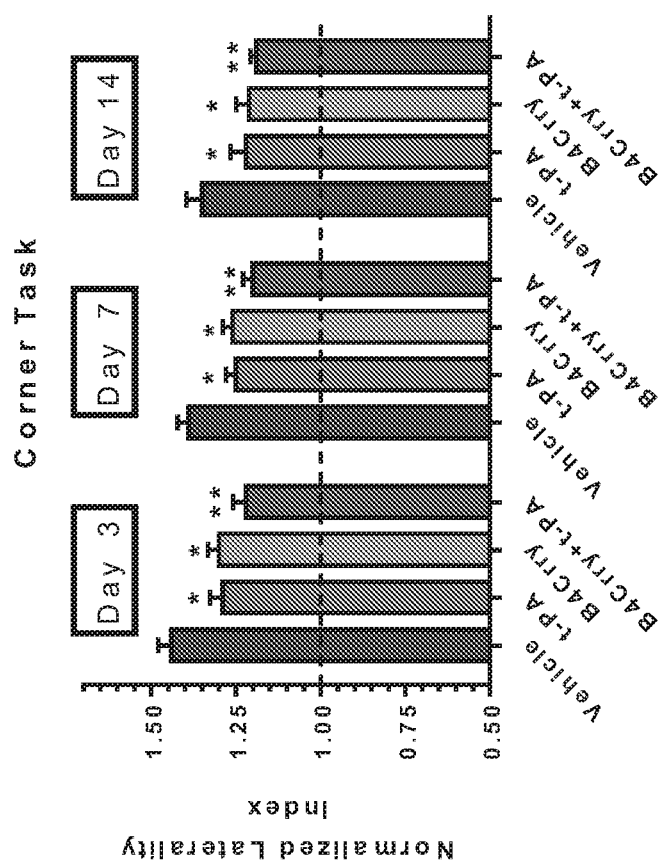
FIG. 4C depicts normalized laterality index on corner task showing a similar improvement in forearm laterality with the different treatments compared to vehicle supporting the findings on neurological deficits. Two-way ANOVA with Bonferroni's test for multiple comparisons. N=8/group. *P<0.05. **P<0.05.
Figure 4D:
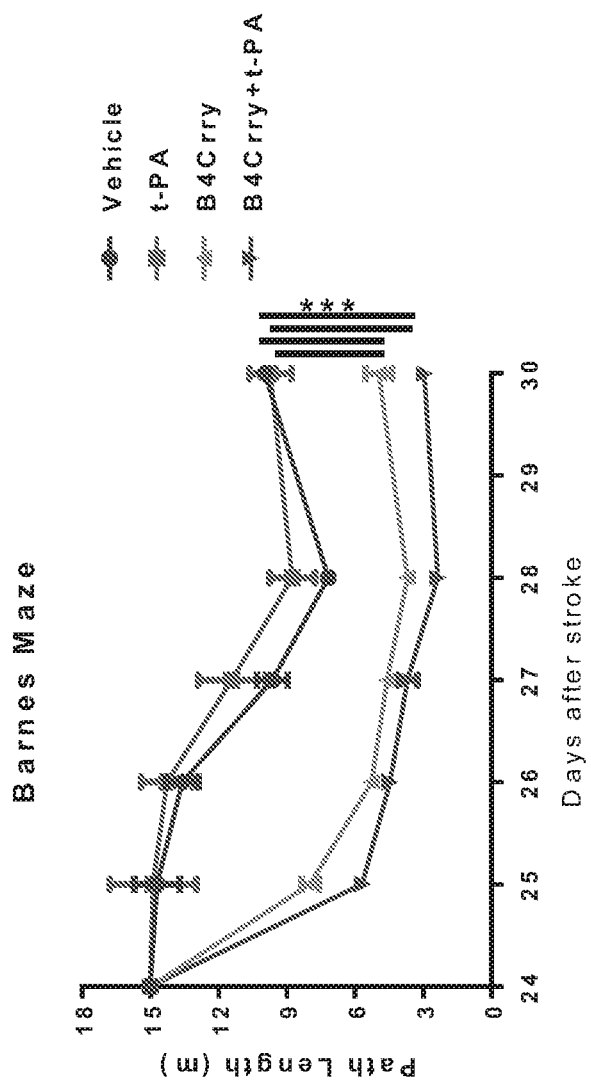
FIG. 4D depicts cognitive performance as assessed by Barnes maze showing significantly faster acquisition and retention of spatial memory in animals treated with B4Crry or B4Crry in combination with t-PA but not t-PA alone. Two-way ANOVA with Bonferroni's test for multiple comparisons. N=8/group. *P<0.05. **P<0.05.
Figure 4E:
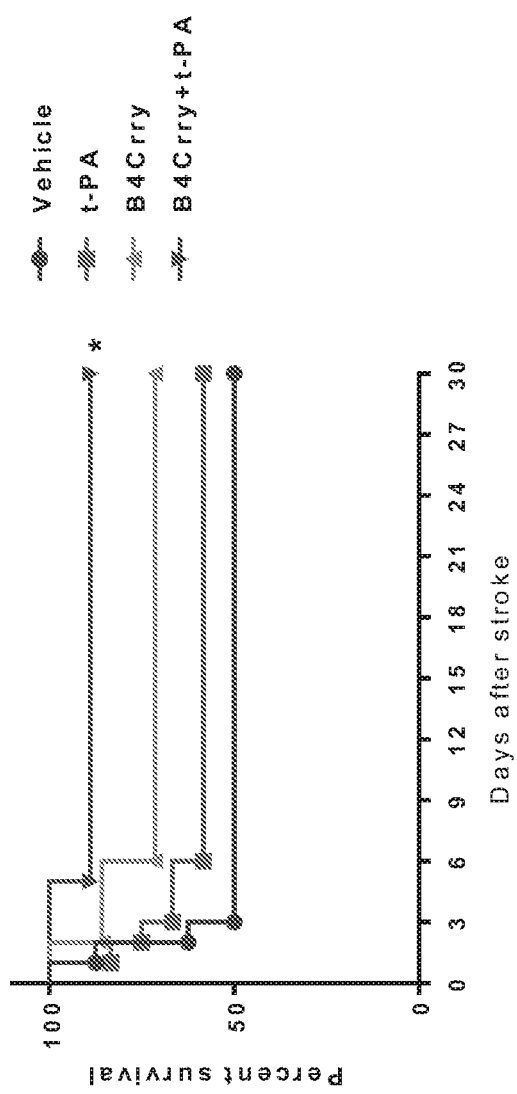
FIG. 4E and FIG. 4F depict results from experiments where animals were subjected to microembolic stroke, treated with t-PA or vehicle at 2 hour, assigned to rehabilitation cages (enriched environment) and assessed over 30 days.

Experiments were also conducted to evaluate motor and cognitive recovery after embolic stroke in subjects treated with t-PA, B4Crry, or the combination of B4Crry and t-PA. Animals were subjected to microembolic stroke, treated with t-PA, B4Crry, the combination of B4Crry and t-PA, or vehicle at 2 hours and assessed over 30 days. FIG. 4A depicts a Kaplan-Meyer survival curve showing that animals treated with B4Crry and t-PA have significantly better 30-day survival compared to vehicle after microembolic stroke and standard care (No rehabilitation). FIG. 4B depicts neurological deficit scores showing that B4Crry, t-PA and more effectively their combination significantly improve recovery of function deficits over 30 days of recovery after microembolic stroke and standard care. FIG. 4C depicts normalized laterality index on corner task showing a similar improvement in forearm laterality with the different treatments compared to vehicle supporting the findings on neurological deficits. FIG. 4D depicts cognitive performance as assessed by Barnes maze showing significantly faster acquisition and retention of spatial memory in animals treated with B4Crry or B4Crry in combination with t-PA but not t-PA alone.

Example 2: The Effect of B4Crry on Acute and Chronic Recovery after Stroke

Experiments were conducted to examine the effects of B4Crry on acute and chronic outcomes after stroke modeled using the middle cerebral artery occlusion model. Motor and cognitive outcomes were assessed over 15 days. Inflammatory and regenerative markers were also investigated using immunostaining of brain sections.

Figure 5A:
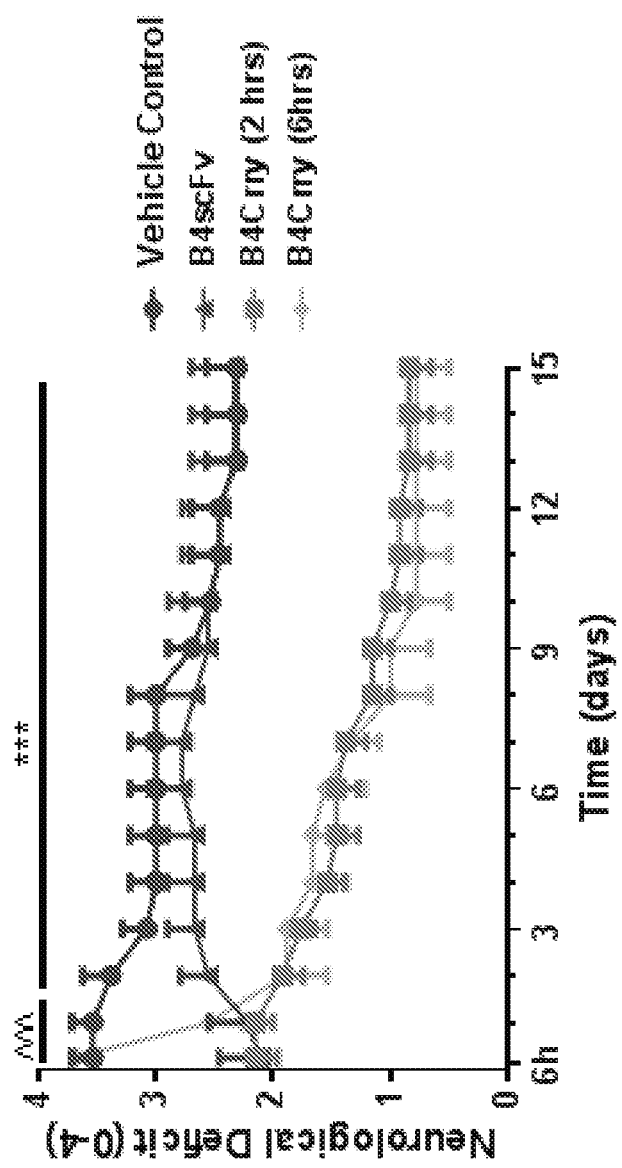
FIG. 5A through FIG. 5M, depicts results illustrating the efficacy of B4Crry in improving chronic outcomes in Middle Cerebral Artery Occlusion model (MCAO) of ischemic stroke with 60 minutes of ischemia.
Figure 5B:
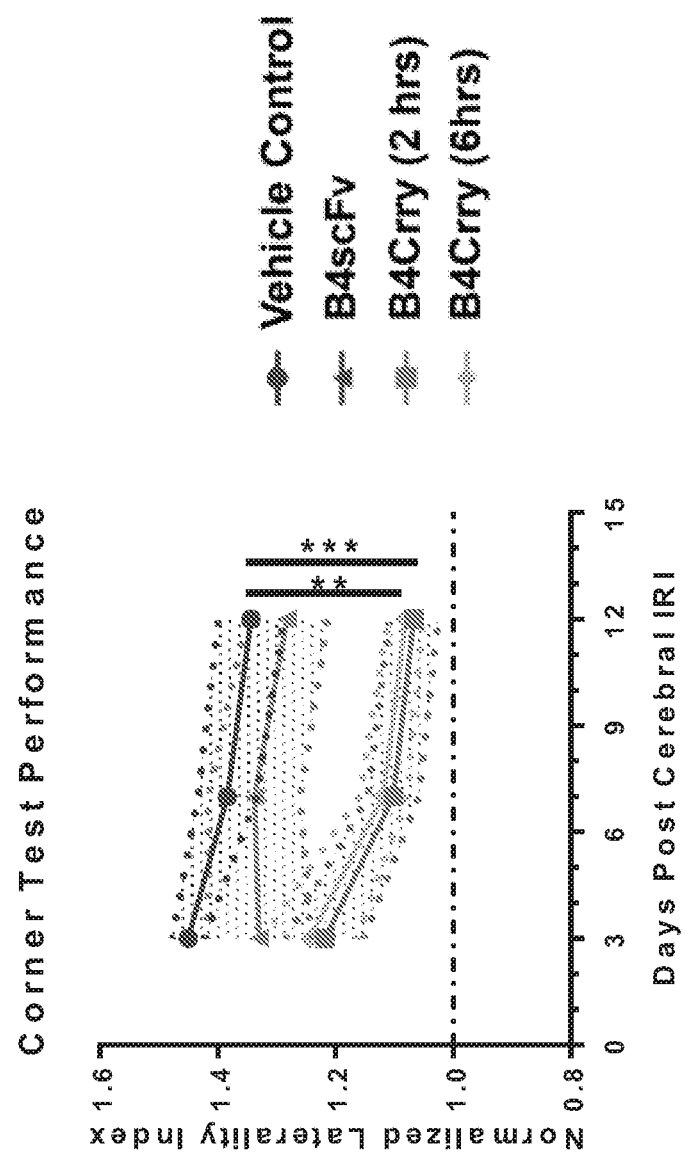
Figure 5C:
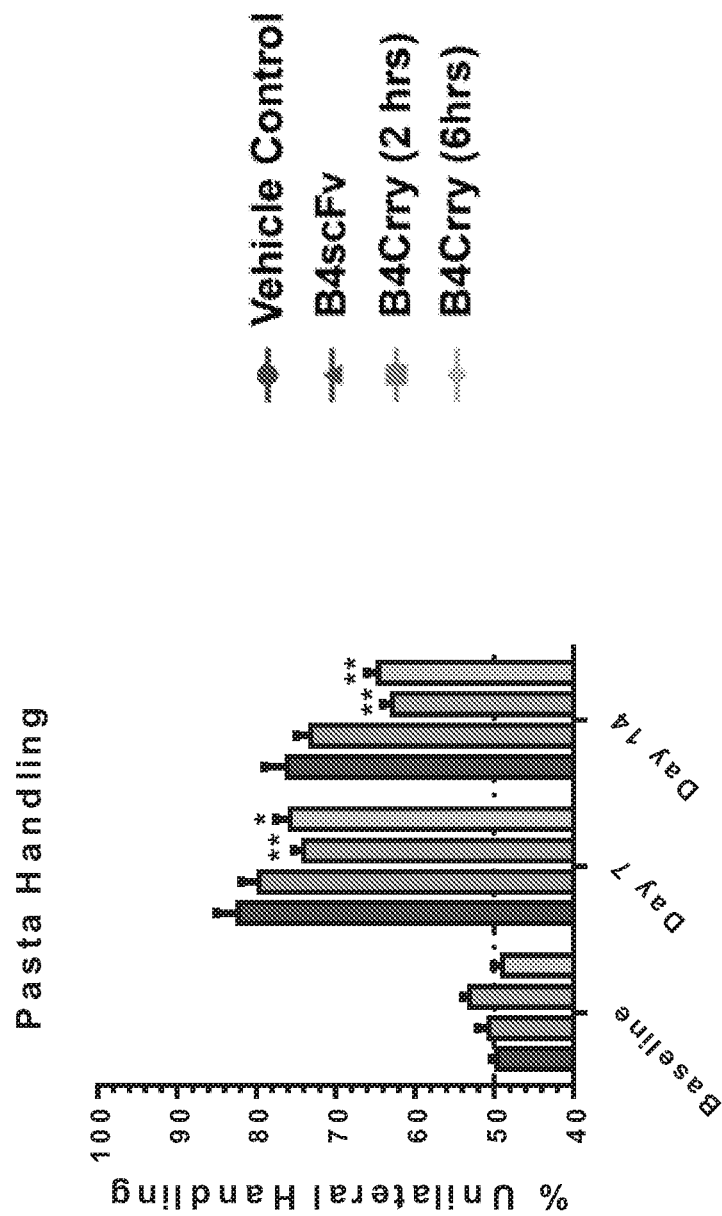
Figure 5D:
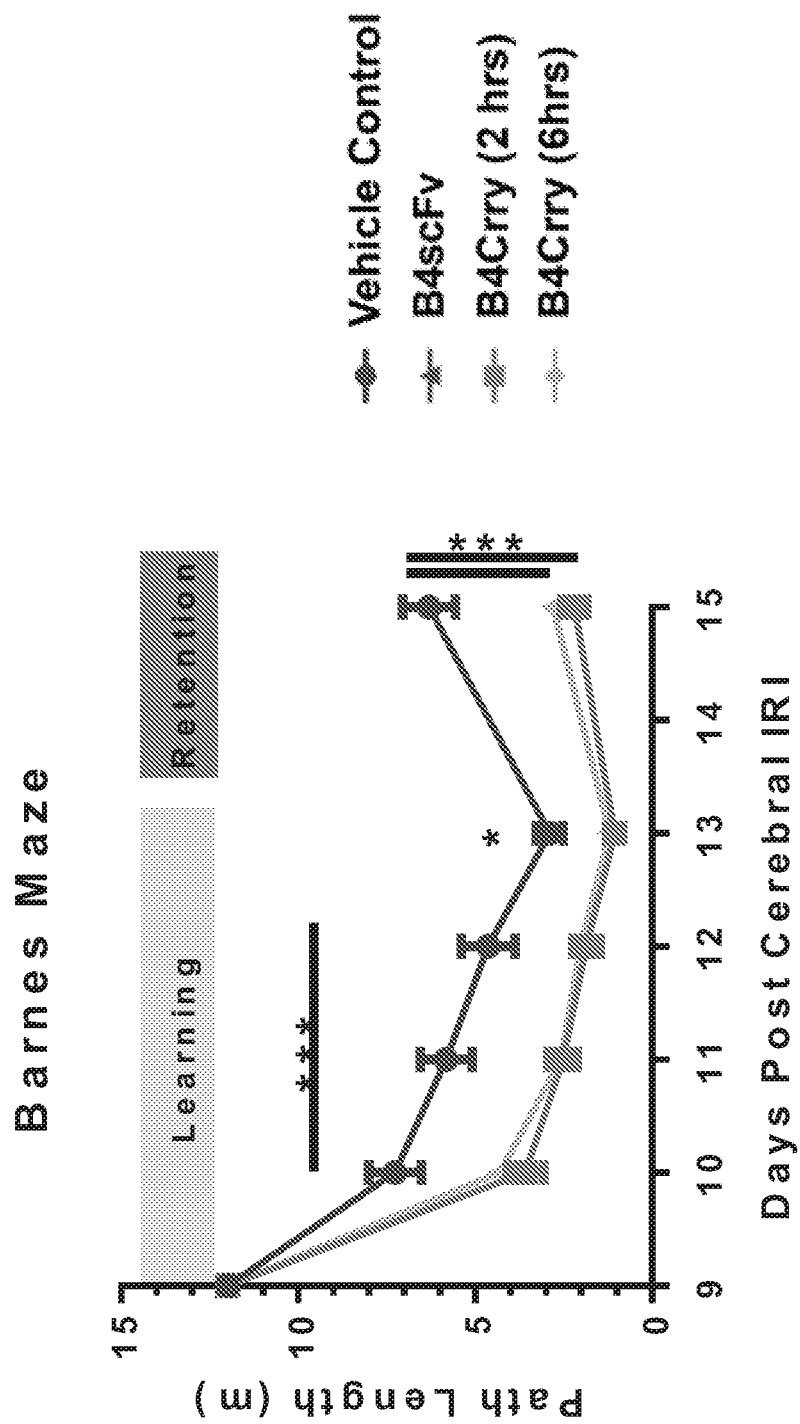
Figure 5E:
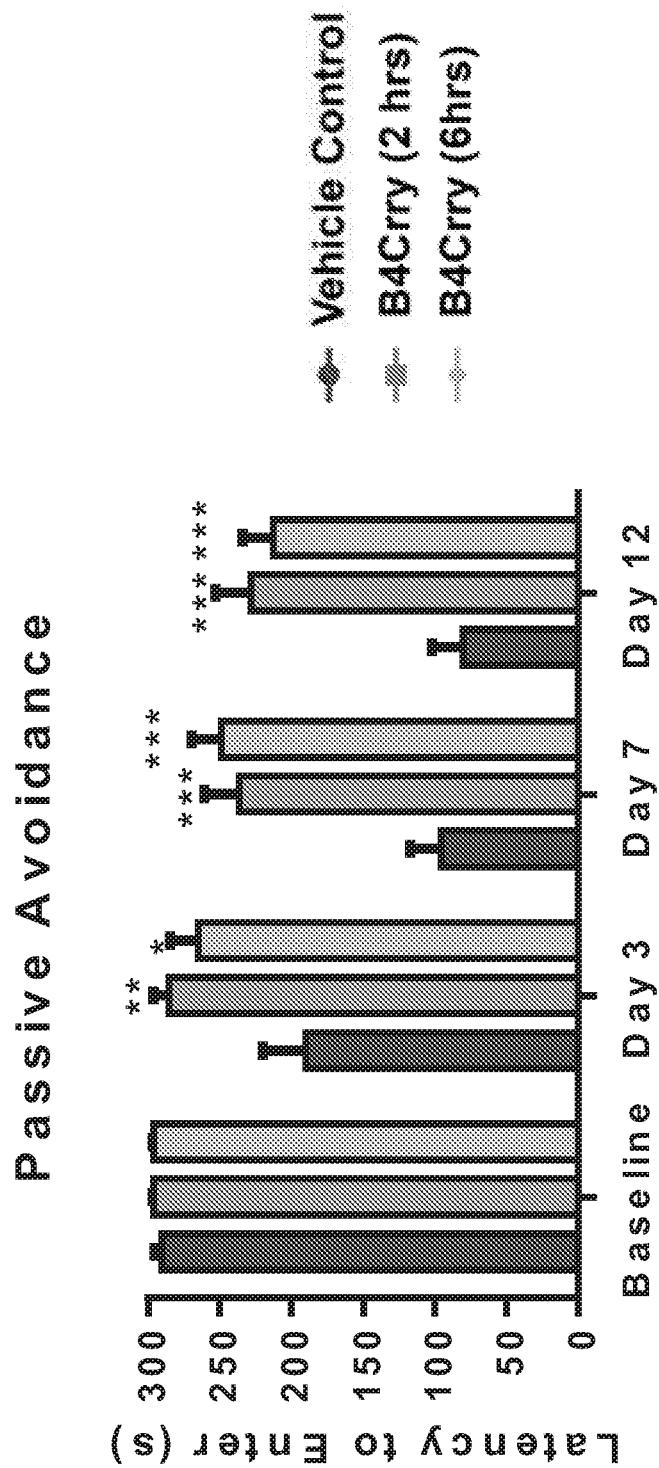
Figure 5F:
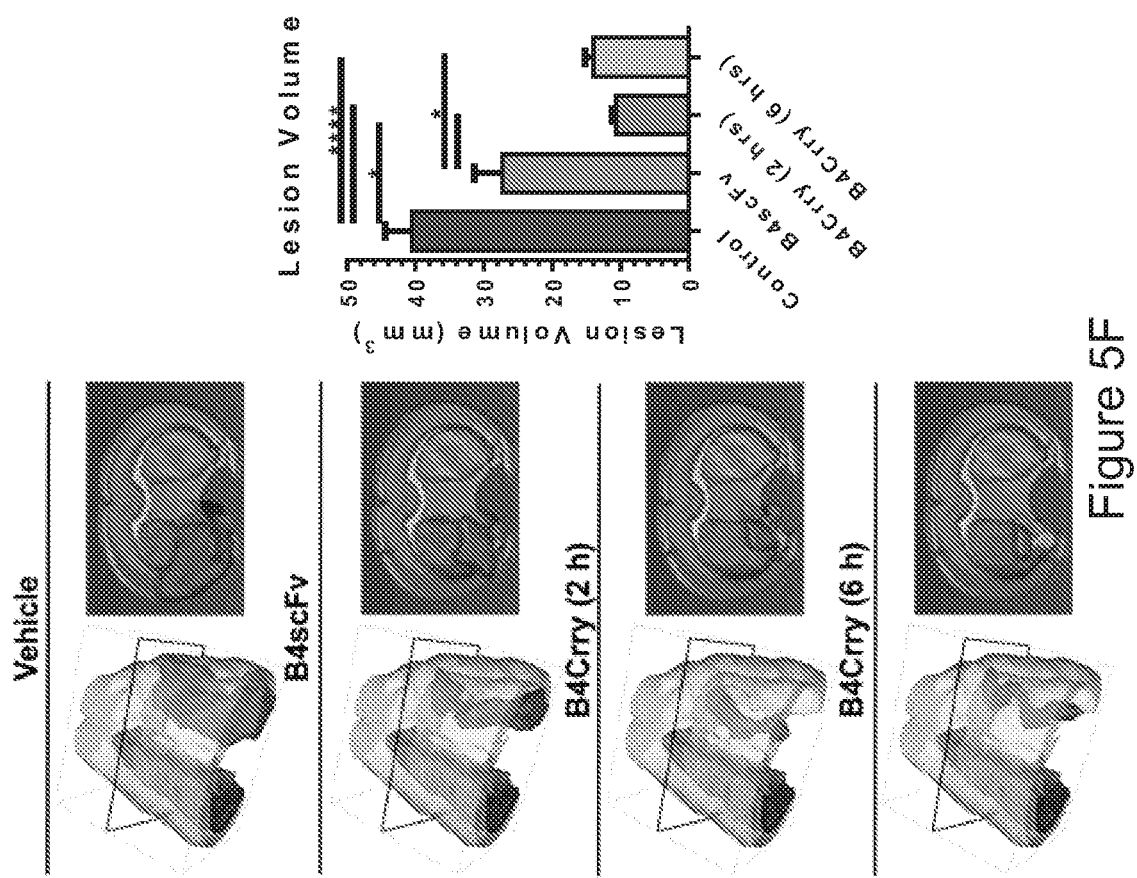
Figure 5G:
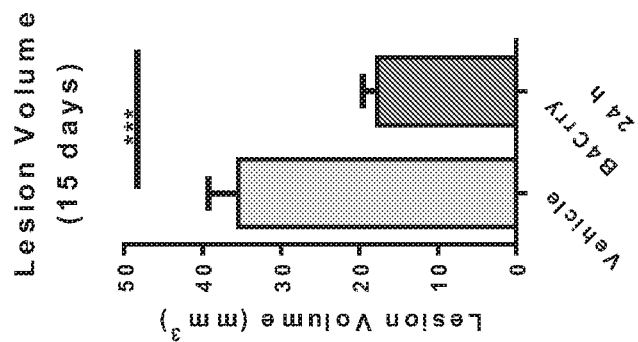
Figure 5H:
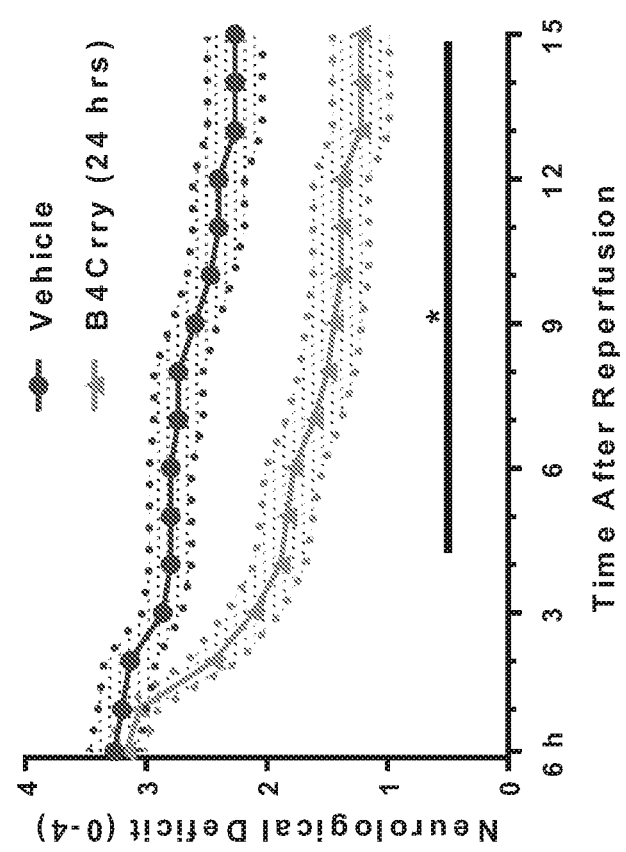
Figure 5I:
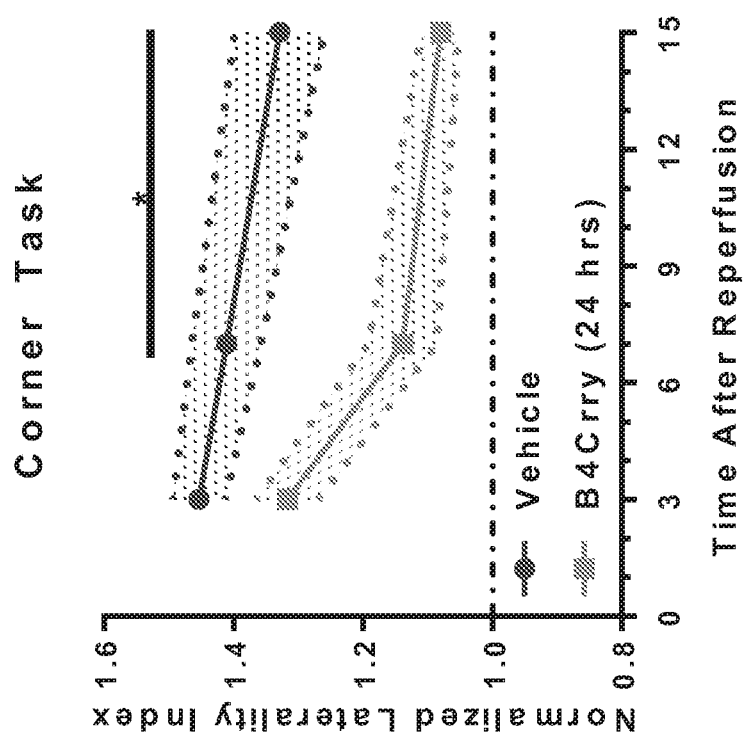
Figure 5J:
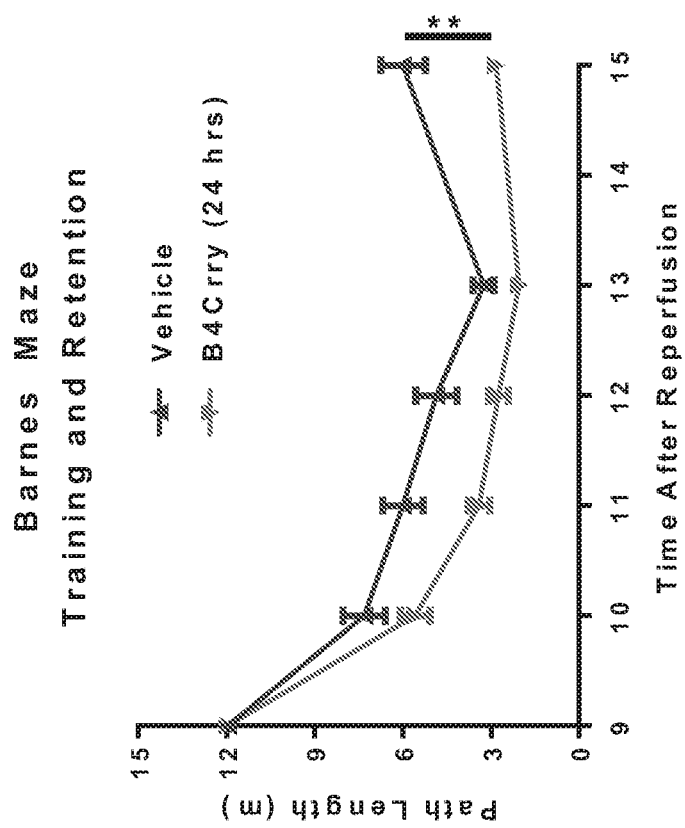
Figure 5K:
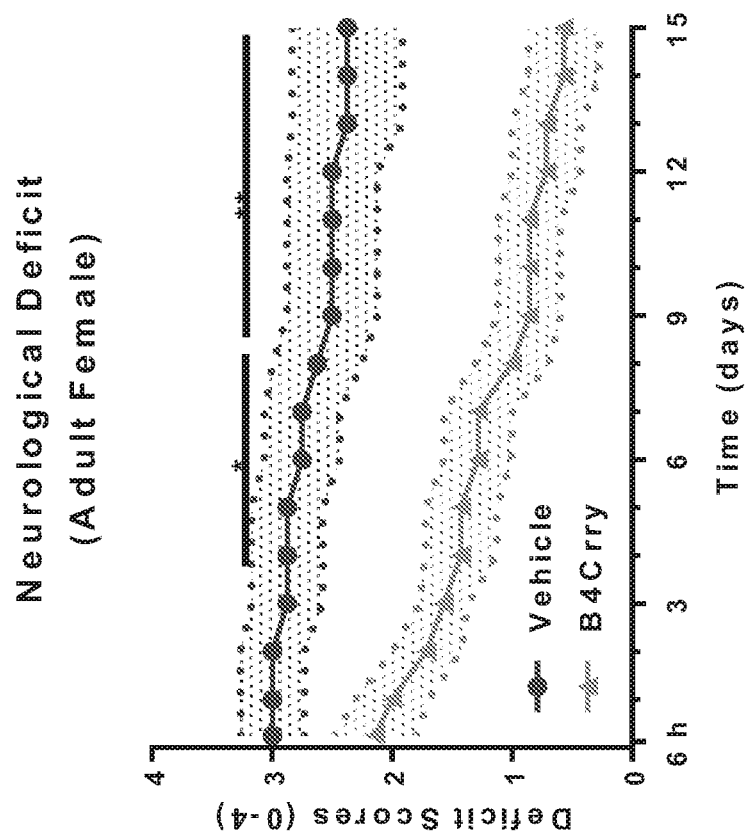
Figure 5L:
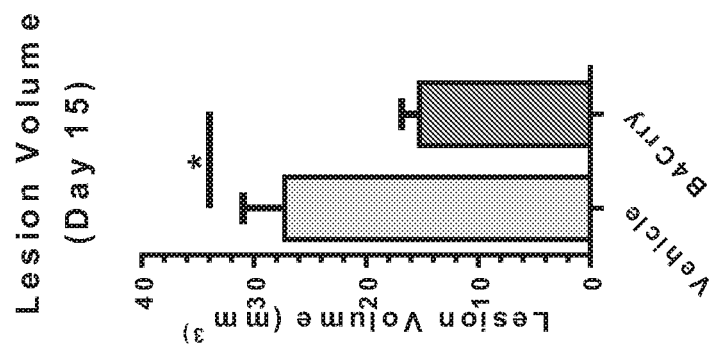
Figure 5M:
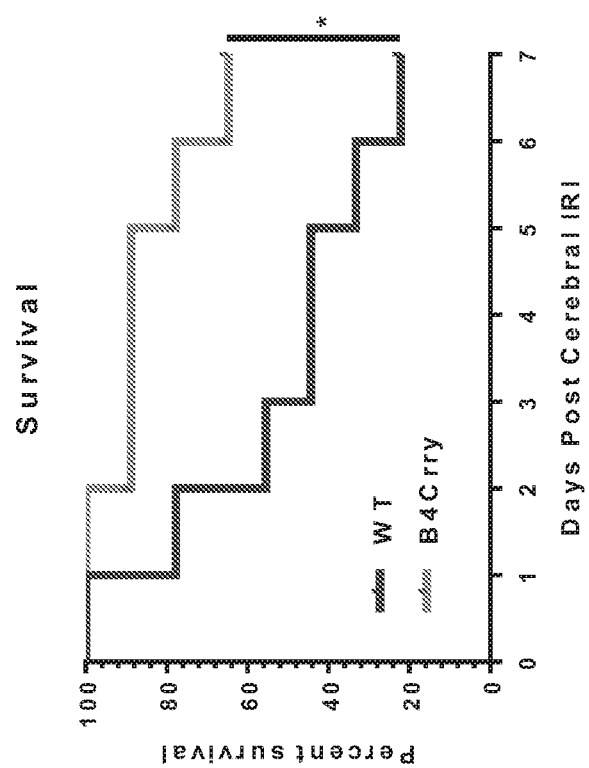

Experiments were conducted to examine the efficacy of B4Crry in improving chronic outcomes in Middle Cerebral Artery Occlusion model (MCAO) of ischemic stroke with 60 minutes of ischemia. FIG. 5A is a graph illustrating daily neurological deficit score, showing that unlike B4scFv, B4Crry treatment at either 2 hours or 6 hours after ischemia resulted in a significant acute reduction in deficit compared to vehicle controls which was sustained throughout 15 days of recovery. FIG. 5B through FIG. 5E demonstrates that animals treated with B4Crry (2 or 6 hours after ischemia) display a significant reduction in forelimb laterality (corner task, FIG. 5B), significant improvement in skilled handling (pasta task, FIG. 5C), significant improvement in spatial learning (Barnes maze, FIG. 5D) and significant improvement in memory retention (passive avoidance, FIG. 5E) with B4Crry treatment at either 2 or 6 hours after ischemia compared to vehicle throughout 15 days of recovery after MCAO. FIG. 5F depicts the effect of B4Crry administered at 2 or 6 hours after stroke showing significant reduction in lesion volume calculated through 3D-reconstruction of lesions from Nissl stained brain sections at 15 days after MCAO. FIG. 5G through FIG. 5J depicts the protective effects of B4Crry administered 24 hours after MCAO on reducing lesion volume (Nissl stain, FIG. 5G), reducing neurological deficits (FIG. 5H) and forelimb laterality (corner test, FIG. 5I), and improving spatial learning and memory (Barnes maze, FIG. 5J) compared to vehicle. FIG. 5K and FIG. 5L depicts the effect of B4Crry (administered 2 hours after MCAO) on neurological deficits (FIG. 5K) and lesion volume (FIG. 5L) in adult female mice. FIG. 5M depicting the effect of B4Crry (administered 2 hours after MCAO) on survival of aged (10 months old) mice after MCAO.

Figure 6A:
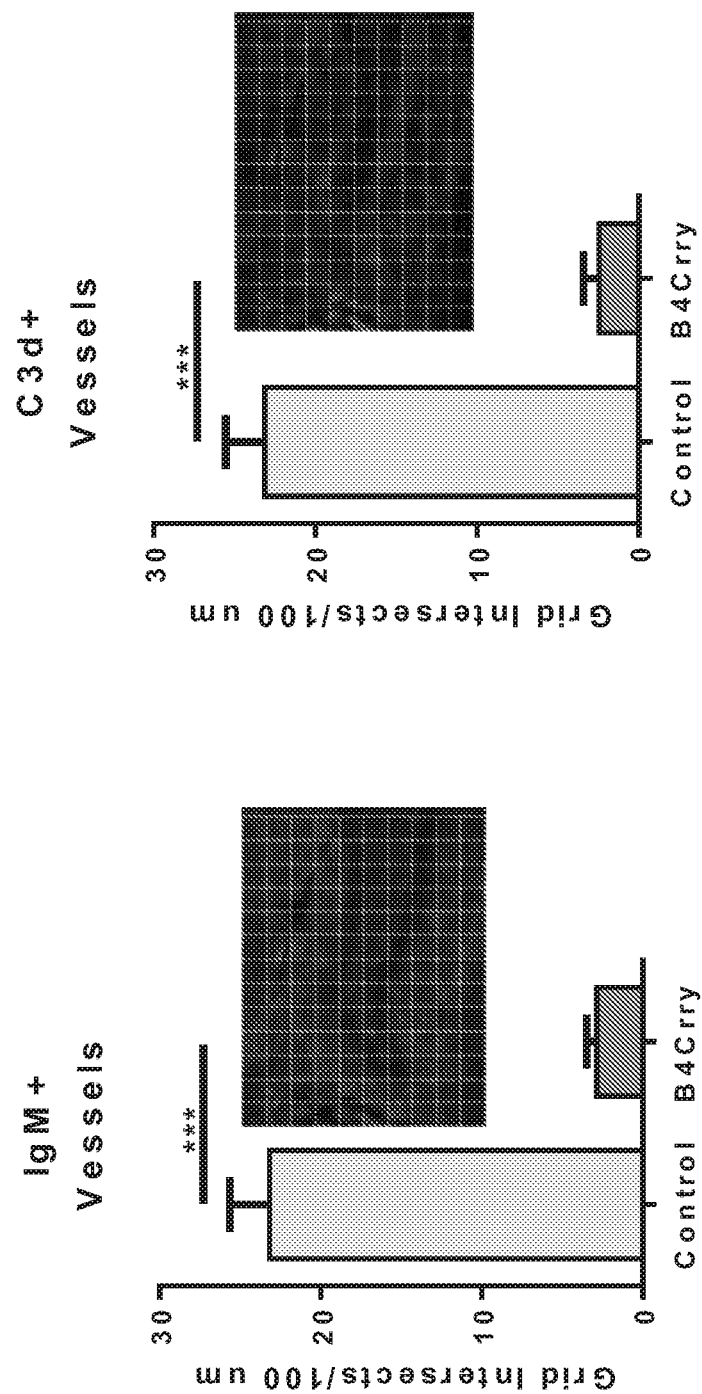
FIG. 6A depicts the quantification, using mean grid intersects, of IgM and complement (C3d) deposition in the brain after MCAO and treatment with vehicle or B4Crry (2 hours after MCAO) using immunofluorescence staining. Student's t-test, N=6 animals (2 fields/animal), ***p<0.001.
Figure 6B:
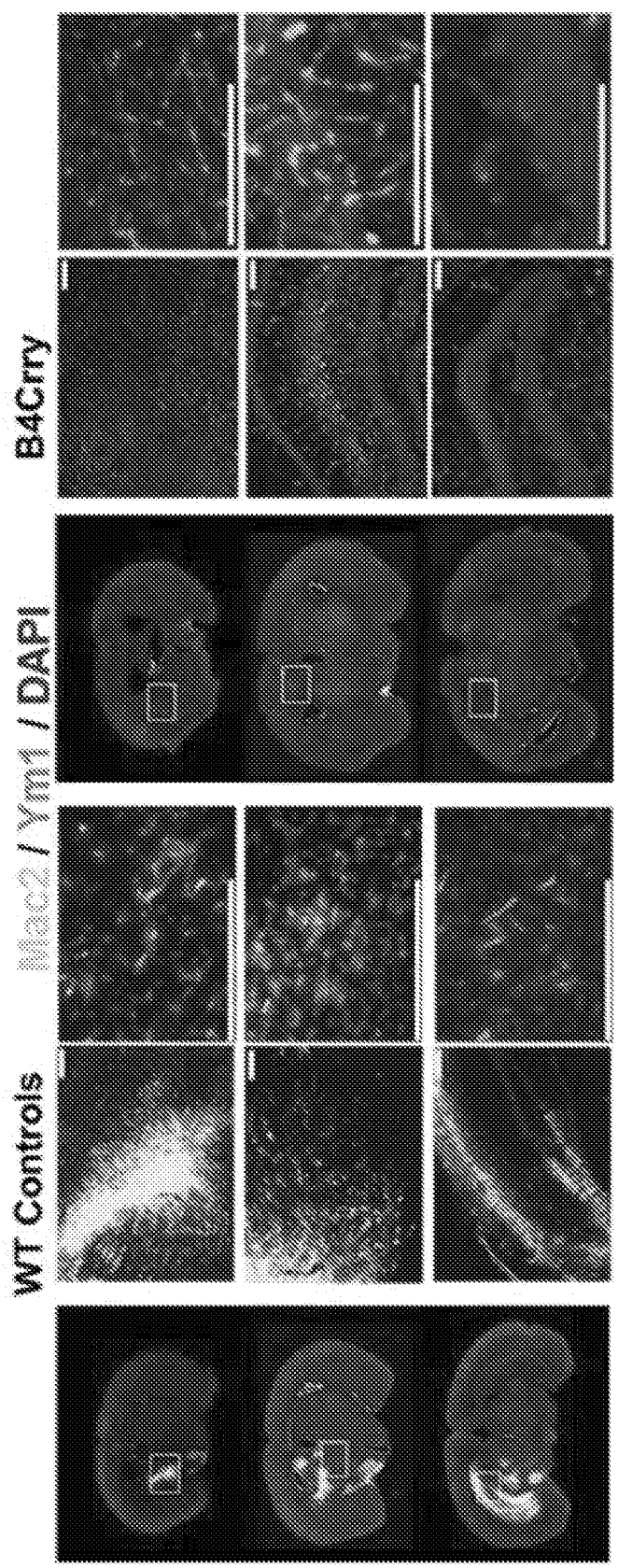
FIG. 6B shows immunofluorescence of inflammatory microglia (using Mac2 as a marker) and anti-inflammatory microglia (using Ym1 as a marker) in the brain 15 days after MCAO showing the B4Crry reduces the activation of inflammatory microglia during chronic recovery.
Figure 6C:
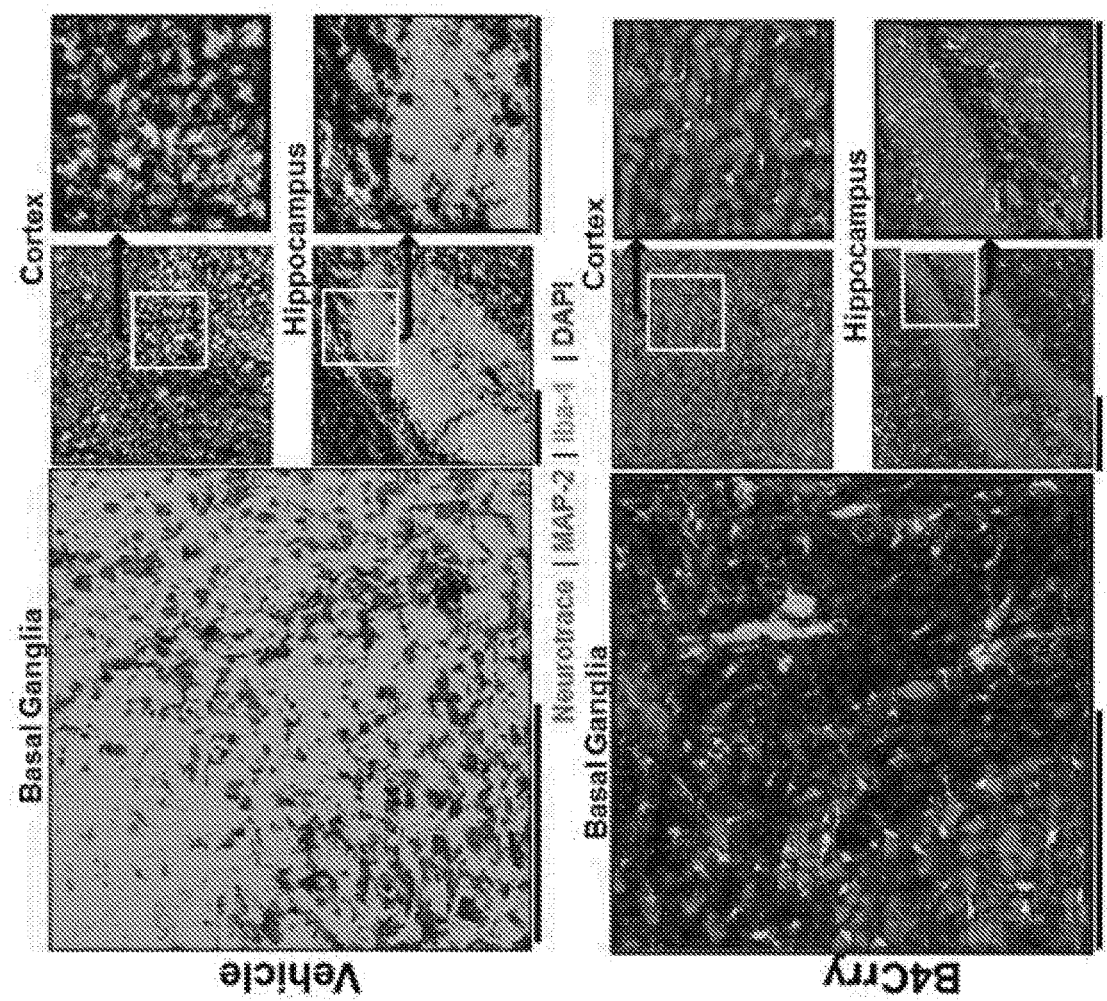
FIG. 6C illustrates immunofluorescence of inflammatory microglia (using Iba1 as a marker), neurons (Neurotrace as a marker), dendrites (MAP-2 as a marker), and DAPI as a nuclear stain. The figure shows extensive microglia proliferation that is associated with loss of neurons and dendrites in the perilesional basal ganglia, hippocampus and cortex at 15 days after MCAO, a process that is interrupted by acute B4Crry treatment.

Experiments were also conducted to examine the effects of B4Crry on markers of inflammation 15 days after MCAO in mice. FIG. 6A depicts the quantification, using mean grid intersects, of IgM and complement (C3d) deposition in the brain after MCAO and treatment with vehicle or B4Crry (2 hours after MCAO) using immunofluorescence staining. Student's t-test, N=6 animals (2 fields/animal), FIG. 6B shows immunofluorescence of inflammatory microglia (using Mac2 as a marker) and anti-inflammatory microglia (using Ym1 as a marker) in the brain 15 days after MCAO showing the B4Crry reduces the activation of inflammatory microglia during chronic recovery. FIG. 6C illustrates immunofluorescence of inflammatory microglia (using Iba1 as a marker), neurons (Neurotrace as a marker), dendrites (MAP-2 as a marker), and DAPI as a nuclear stain. The figure shows extensive microglia proliferation that is associated with loss of neurons and dendrites in the perilesional basal ganglia, hippocampus and cortex at 15 days after MCAO, a process that is interrupted by acute B4Crry treatment.

Example 3: The Effect of C2Crry on Acute and Chronic Recovery after Stroke

Experiments were conducted to examine the effects of C2Crry on acute and chronic outcomes after stroke modeled using the middle cerebral artery occlusion model. C2Crry or vehicle was administered to mice 2 hours after MCAO, and were evaluated for survival, neurological deficit, and memory retention for 14-21 days.

Figure 7A:
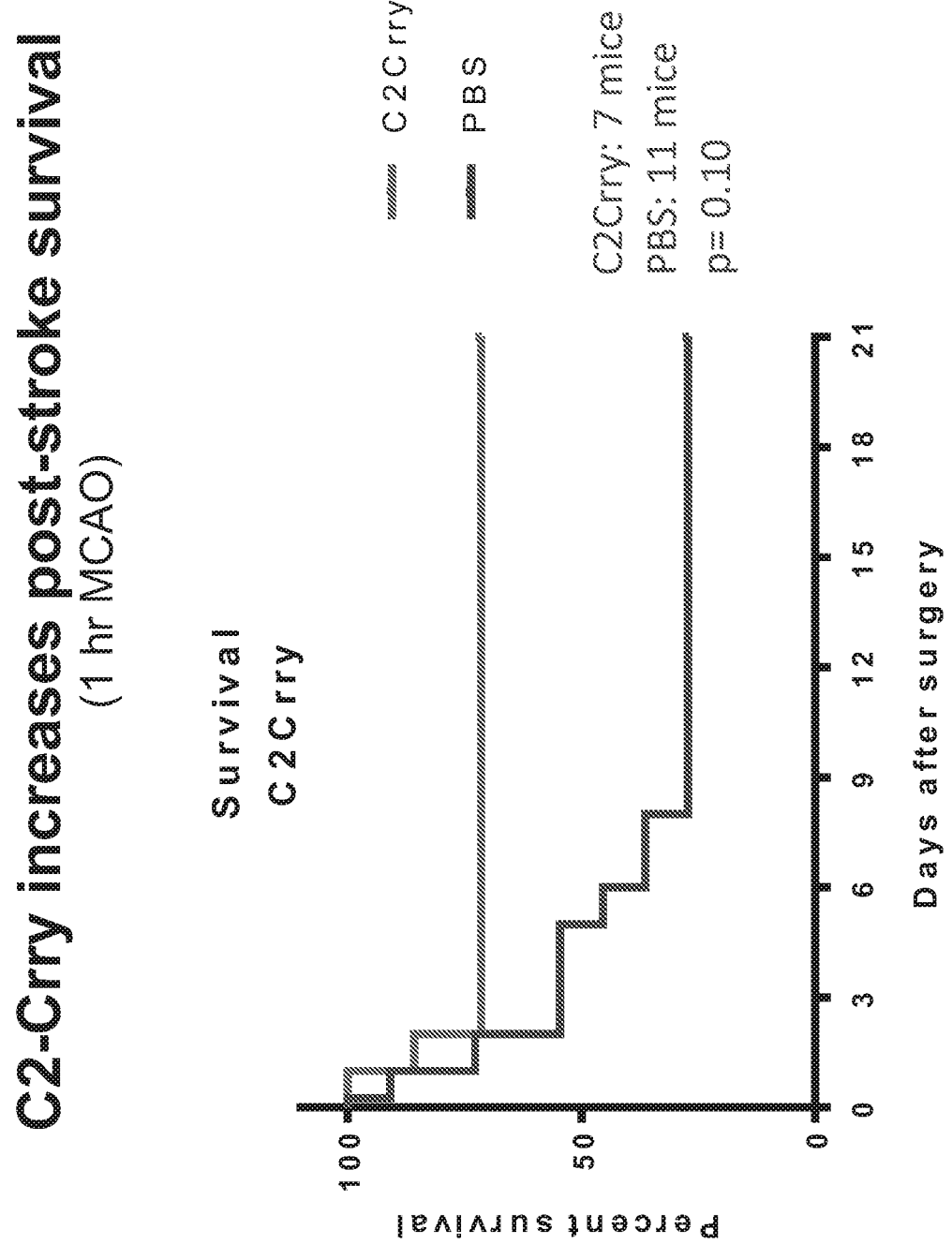
FIG. 7A through FIG. 7C, depicts the results of example experiments demonstrating that the C2-Crry complement inhibitor improves survival and neurological function post-stroke.
Figure 7B:
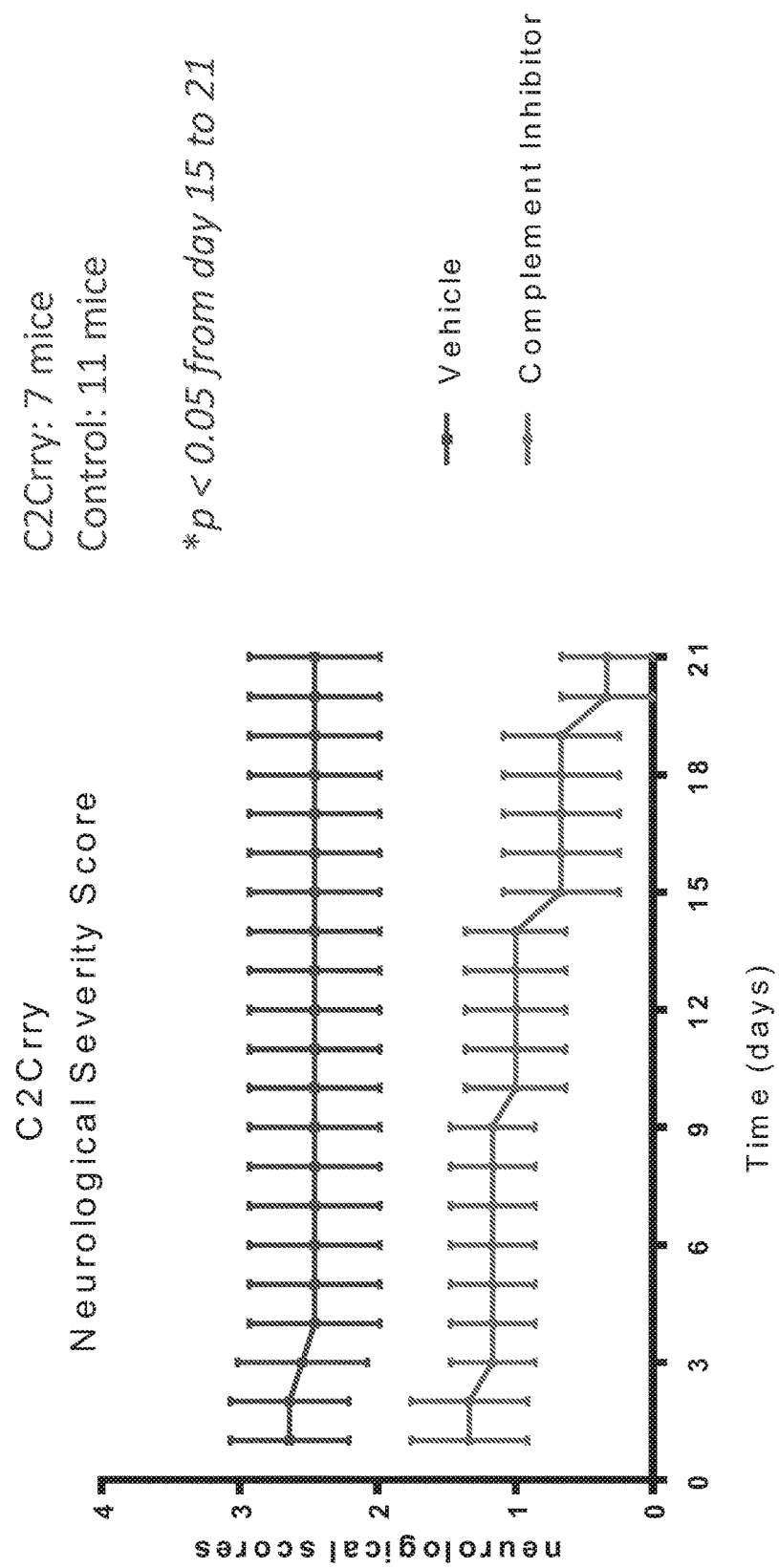
Figure 7C:
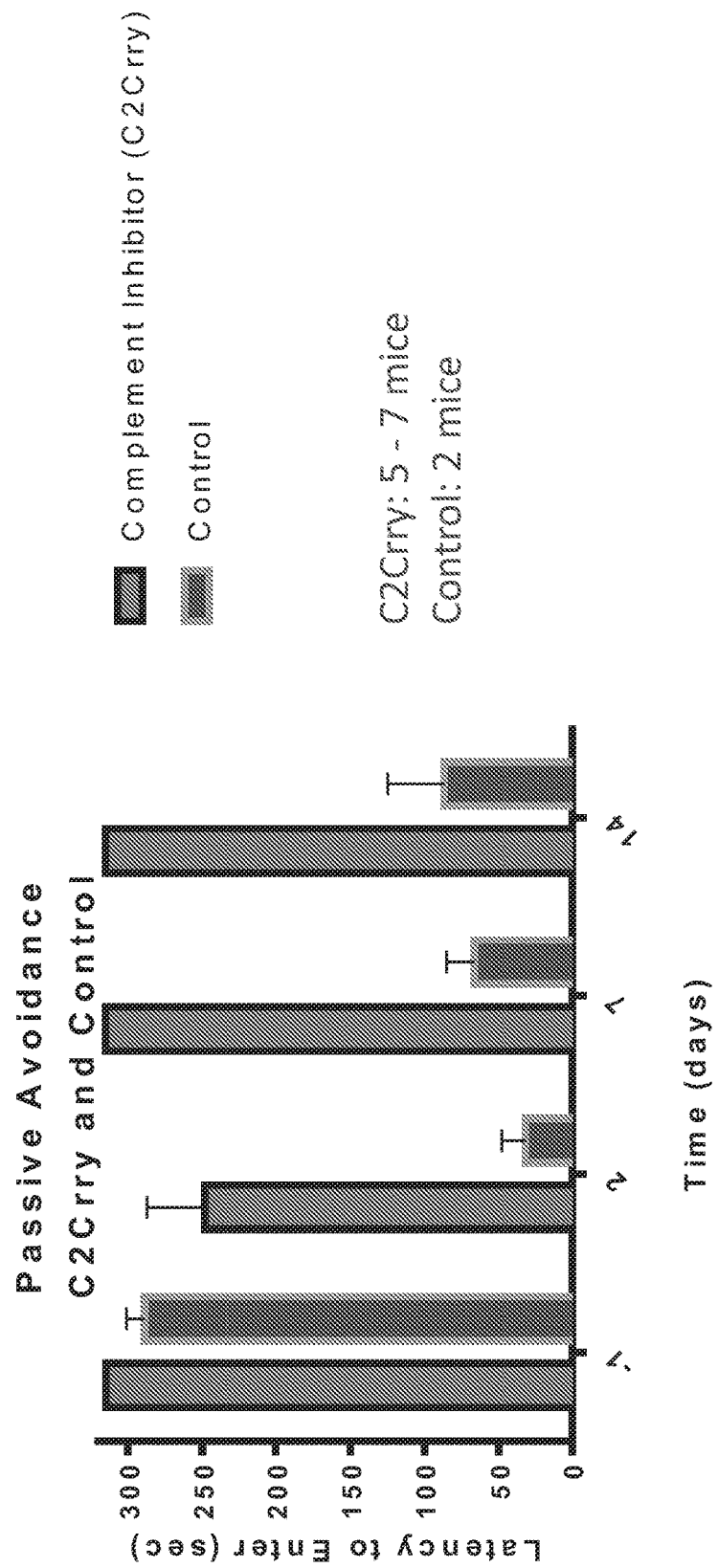

It was observed that mice treated with C2Crry post stroke had increased survival (FIG. 7A). Further, it was observed that mice treated with C2Crry displayed a decrease in neurological deficit after stroke, as compared to vehicle (FIG. 7B). Further, it was observed that mice treated with C2Crry displayed greater memory retention as compared to vehicle treated mice (FIG. 7C).

Example 4: A Synergistic Effect of Complement Modulation and Rehabilitation on Chronic Recovery after Stroke with or without t-PA Administration Experiments were conducted to examine the effect of B4-Crry in the context of the two standards of care for stroke, namely t-PA and rehabilitation therapy. The model used in this example is a microembolic stroke model where microembolic (dose of $1 \times 10^7$ emboli) were injected into the middle cerebral artery followed by administration of vehicle, t-PA (8 mg/kg), B4Crry (16 mg/kg), or combination of t-PA (8 mg/kg) and B4Crry (16 mg/kg) at 2 hours after stroke. Animals were then allocated to a rehabilitation (enriched environment) or to normal housing starting day 2 after stroke until 30 days after srple (FIG. 4A-FIG. 4H). FIG. 4A-FIG. 4D depicts findings of animals in regular housing. FIG. 4E-FIG. 4H depicts animals in rehabilitation environment.

The methods employed in these experiments are described.

B4-Crry Treatment to Evaluate Acute Hemorrhage and Survival after MCAO

The percentage of animals dying due to hemorrhage (of total acute deaths) was measured in B4-Crry treated animals compared to controls. Hemoglobin content in the ipsilateral hemisphere was measured 12 hours after B4-Crry treated MCAO and compared to vehicle. Brain sections were Nissl stained and evaluated for hemorrhagic transformation and intracerebral hemorrhage in B4-Crry treated animals compared to vehicle controls at 24 hours after MCAO. Survival throughout 15 days of recovery after MCAO was evaluated following the combination of B4-Crry and rehabilitation. Survival curve measurements were made to evaluated post-stroke mortality up to 15 days after injury.

B4Crry Treatment+ Rehabilitation after MCAO

Brains of mice that underwent MCAO and were treated with B4-Crry+Rehab were evaluated by T2-weighted MM and immunohistochemistry in order to evaluate infarct exacerbation and scarring. Imaging of brains following MCAO T2-weighted MRI scans were conducted at days 4 and 14 after MCAO in vehicle and rehab animals compared to B4Crry treated animals with or without rehab. Brains were Nissl stained. Lesions were mapped at different stereotactic coordinates (relative to Bregma) to the Paxinos brain atlas to determine the location and size of lesion as well as the frequency of involvement of each brain region across animals. Quantification of lesion volume were used to compare histologically whether B4Crry reduces secondary scarring 15 days after MCAO relative to vehicle or rehab alone.

Cognitive Performance after MCAO with Rehab or B4-Crry

Spatial learning (days 9-11 after MCAO) and retention of learned memory (day 15 post-MCAO) were evaluated in B4-Crry mice compared to vehicle controls as assessed by the total path length or Barnes maze before reaching the target hole or the number of error pokes. Co-treatment with B4-Crry and rehab was also evaluated. Passive avoidance was evaluated in animals treated with B4Crry+/− rehab to evaluate memory retention (longer time to enter the shock chamber) compared to vehicle and rehab alone starting 7 days after MCAO. Principle component analysis of the performance on the different motor and cognitive tasks was also evaluated.

Evaluation of Inflammatory Response after MCAO in B4-Crry-Treated Animals

Sustained neuroinflammatory response was evaluated in terms of C3d and IgM deposition and inflammatory microglial activation 15 days after MCAO following single acute administration of B4-Crry 90 minutes after MCAO.

B4-Crry Impact on Effectiveness of Rehab Therapy

The effect of B4-Crry treatment on the persistence of regenerative mechanisms was evaluated to determine whether maximal effect of rehab therapy was able to be achieved. Dcx immunostaining of perilesional hippocampi was quantified in terms of the number of neuroblasts migrating to the ipsilateral hippocampus 15 days after injury with rehab, B4-Crry or combination therapy. Immunostaining for markers of regeneration and remodeling including dendritic arborization (MAP2), synaptic density (PSD-95) and axonal growth (GAP-43) of full brain slices were also evaluated to determine whether the combination of B4Crry and rehab effect dendritic and axonal growth relative to the perilesional area and synaptic density.

The results of the experiments are now described.

Figure 4F:
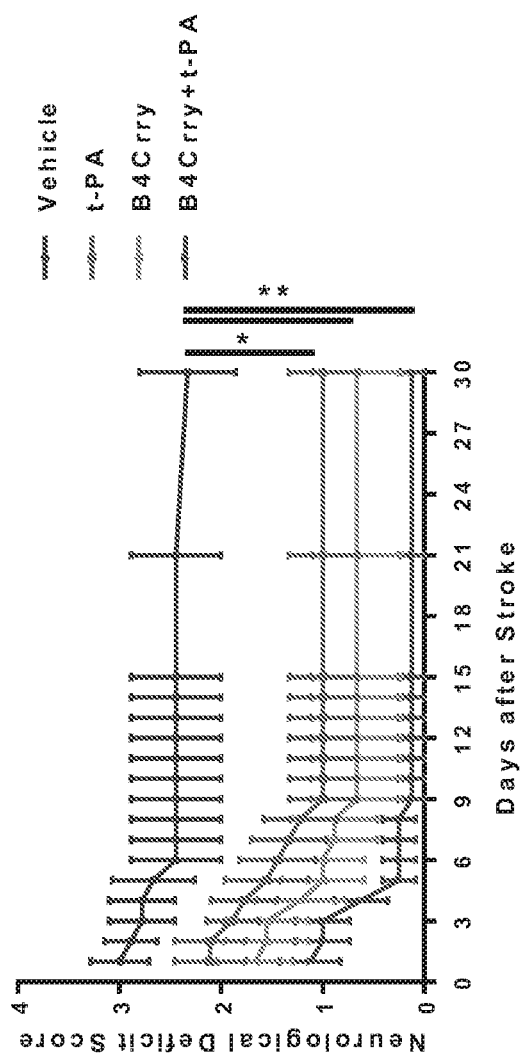
Figure 4G:
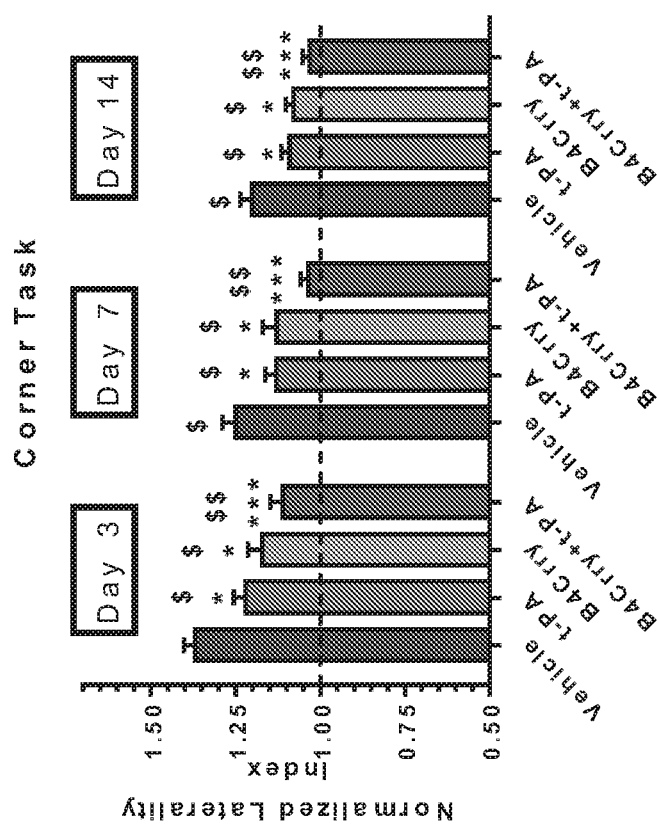
FIG. 4G depicts normalized laterality index on corner task showing a similar improvement in forearm laterality with the different treatments compared to vehicle supporting the findings on neurological deficits. Comparison to standard housing was performed for each treatment group showing a significant reduction in motor deficits in animals treated with rehabilitation compared to standard housing starting day 7 after stroke. Two-way ANOVA with Bonferroni's test for multiple comparisons. N=8/group. *P<0.05. **P<0.05. $P<0.05 $$P<0.01 compared to standard housing for each treatment category.

B4Crry Enhances t-PA and Rehabilitation-Induced Chronic Motor Recovery after Stroke Functional and motor recovery after stroke was assessed by neurological deficit scores and the corner task (measure of forearm laterality). In the absence of rehabilitation, t-PA and B4Crry resulted in equivalent reduction in neurological deficits and forearm laterality over 30 days (FIG. 4B and FIG. 4C), but combination of B4Crry and t-PA resulted in a more robust reduction in neurological deficit and forearm laterality. FIG. 4B depicts the neurological deficit over 30 days after embolic stroke and shows that t-PA, B4Crry, and more effectively their combination, reduce chronic neurological deficits. FIG. 4C depicts forearm laterality index on corner task, and shows that t-PA, B4Crry, and more effectively their combination, reduces chronic forearm laterality. In the context of rehabilitation, a similar effect is seen as in normal housing in terms of a significant reduction in neurological deficit and forearm laterality in animals treated with B4Crry or B4Crry and t-PA compared to vehicle (rehabilitation only) as in FIG. 4F and FIG. 4G. However, compared to no rehabilitation, rehabilitation did not significantly improve motor function (neurological deficit or forearm laterality), but when combined with B4Crry or B4Crry+t-PA, rehabilitation had an additional effect on motor function (FIG. 4F and FIG. 4G compared to FIG. 4B and FIG. 4C). FIG. 4F depicts the neurological deficit over 30 days after embolic stroke in animals subjected to rehabilitation after treatment with vehicle, t-PA, B4Crry or B4Crry+t-PA. FIG. 4G depicts forearm laterality index on corner task in animals subjected to rehabilitation after treatment with vehicle, t-PA, B4Crry or B4Crry+t-PA. Compared to no rehabilitation, animals treated with rehabilitation+B4Crry or rehabilitation+B4Crry+t-PA had significantly lower forearm laterality on corner task compared to animals treated with B4Crry or B4Crry+t-PA in absence of rehabilitation respectively. These results show that B4Crry enhances the effects of both t-PA and rehabilitation on motor recovery after embolic stroke.

Figure 4H:
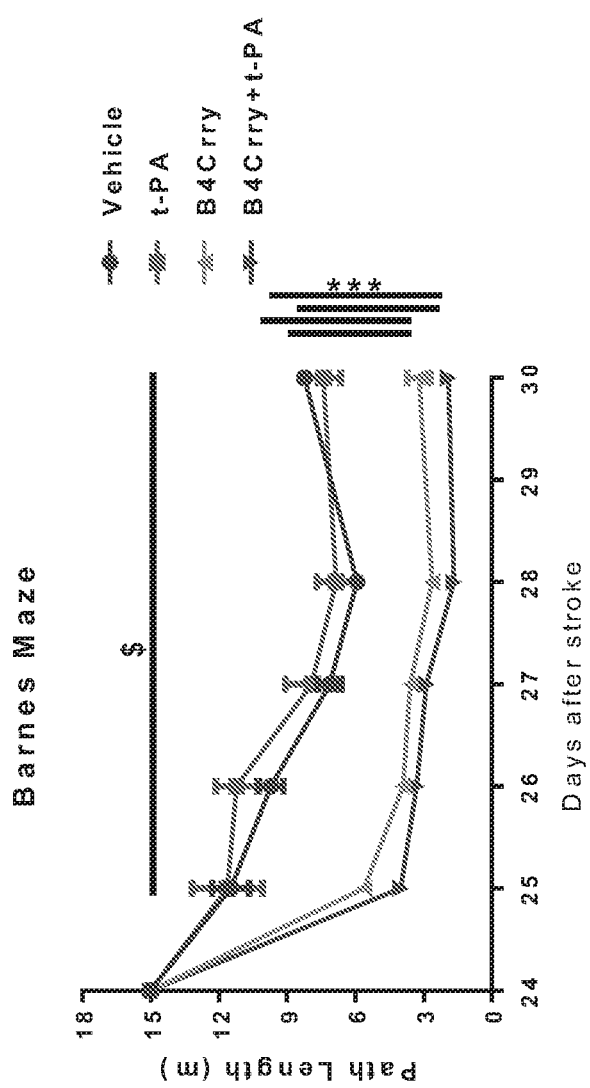
FIG. 4H depicts cognitive performance as assessed by Barnes maze showing significantly faster acquisition and retention of spatial memory in animals treated with B4Crry or B4Crry in combination with t-PA but not t-PA alone. Two-way ANOVA with Bonferroni's test for multiple comparisons. N=8/group. *P<0.05. **P<0.05. Comparison between rehabilitation and standard housing for each treatment group showed a significant improvement in cognitive performance on Barnes maze once rehabilitation is added to either treatment option. Two-way ANOVA with Bonferroni's test for multiple comparisons. N=8/group. $P<0.05.

B4Crry but not t-PA Enhances Rehabilitation-Induced Chronic Cognitive Recovery after Stroke Cognitive recovery after embolic stroke was assessed at 24-30 days after stroke using the Barnes maze task to evaluate the effect of treatment on the ability of mice to learn and retain spatial memory. It is first shown that in the absence or presence of rehabilitation, t-PA alone does not improve spatial learning over 5 days of training on the Barnes maze measured by the total path required for the animals to find the escape hole, and did not improve the retention of learned memory compared to vehicle in either groups (non-rehabilitation: FIG. 4D; or rehabilitation: FIG. 4H). Rehabilitation alone resulted in mild improvement in spatial learning and memory compared to normal housing. B4Crry alone and in combination of t-PA resulted in a significant improvement in the learning and retention of learned memory compared to both vehicle and t-PA in the absence of rehabilitation (FIG. 4D). FIG. 4D depicts the results of the Barnes maze task performed on days 24-30 after stroke and show that animals treated with B4Crry or B4Crry+t-PA had a significantly better spatial learning and retention of learned memory compared to t-PA alone or vehicle in absence of rehabilitation. A similar effect of significant improvement in the learning and retention of learned memory in animals treated with B4Crry or B4Crry+t-PA compared to both vehicle and t-PA was also seen when all groups received rehabilitation therapy (FIG. 4H). Comparing B4Crry+t-PA or B4Crry to B4Crry+t-PA+rehabilitation or B4Crry+rehabilitation respectively showed that rehabilitation exhibits an additive effect in improving learning and memory retention chronically after stroke. FIG. 4H depicts the results of the Barnes maze task performed on days 24-30 after stroke and show that animals treated with B4Crry or B4Crry+t-PA had a significantly better spatial learning and retention of learned memory compared to t-PA alone or vehicle in presence of rehabilitation, and compared to B4Crry or B4Crry-t-PA in absence of rehabilitation.

Example 5: Traumatic Brain Injury

Experiments are conducted to examine the effect of a targeted complement inhibitor (e.g. B4Crry) on the recovery after traumatic brain injury. Two months after TBI, animals received 3 doses of vehicle or targeted complement inhibitor every other day, and then assigned to rehabilitation (enriched environment or regular housing). Recovery is assessed using the Barnes maze to measure learning and retention of learned memory.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating a central nervous system injury in a subject, the method comprising (a) administering to the subject a therapeutically effective amount of a composition comprising a targeted inhibitor molecule comprising a targeting portion and a complement inhibitor, and (b) administering to the subject a composition comprising a thrombolytic agent.

2. The method of claim 1, wherein the injury is ischemic stroke.

3. The method of claim 1, wherein the injury is traumatic brain injury.

4. The method of claim 1, wherein the injury is spinal cord injury.

5. The method of claim 1, wherein the targeting portion comprises an antibody or fragment thereof that binds to Annexin IV or a phospholipid.

6. The method of claim 1, wherein the complement inhibitor is selected from the group consisting of: Factor H, DAF, MCP, CD59, Crry, MAp44, and CR1, or a fragment thereof.

7. The method of claim 1, wherein the thrombolytic agent is at least one of: tissue plasminogen activator (t-PA), urokinase, anistreplase, ancrod, and brinase.

8. The method of claim 1, wherein the method further comprises (c) providing a rehabilitation therapy to the subject.

9. The method of claim 8, wherein the rehabilitation therapy comprises at least one therapy selected from the group consisting of: a cognitive therapy and a motor therapy.

* * * * *